(12) United States Patent
Sands et al.

(10) Patent No.: US 8,728,456 B2
(45) Date of Patent: May 20, 2014

(54) PROGRAMMING OF CELLS FOR TOLEROGENIC THERAPIES

(75) Inventors: Roger Warren Sands, Cambridge, MA (US); Eduardo Alexandra Barros e Silva, Cambridge, MA (US); Toshihisa Kawai, Brookline, MA (US); David J. Mooney, Sudbury, MA (US)

(73) Assignees: President and Fellows of Harvard College, Cambridge, MA (US); Forsyth Dental Infirmary for Children, Cambridge, MA (US)

( * ) Notice: Subject to any disclaimer, the term of this patent is extended or adjusted under 35 U.S.C. 154(b) by 0 days.

(21) Appl. No.: 13/386,950

(22) PCT Filed: Aug. 2, 2010

(86) PCT No.: PCT/US2010/044117
§ 371 (c)(1),
(2), (4) Date: Jan. 25, 2012

(87) PCT Pub. No.: WO2011/014871
PCT Pub. Date: Feb. 3, 2011

(65) Prior Publication Data
US 2012/0121539 A1 May 17, 2012

Related U.S. Application Data

(60) Provisional application No. 61/230,169, filed on Jul. 31, 2009.

(51) Int. Cl.
| A61K 39/35 | (2006.01) |
| A61K 39/00 | (2006.01) |
| A61K 38/20 | (2006.01) |
| A61K 38/19 | (2006.01) |
| A61P 37/04 | (2006.01) |
| A61P 37/06 | (2006.01) |
| A61P 3/10 | (2006.01) |
| A61P 29/00 | (2006.01) |
| A61P 37/08 | (2006.01) |

(52) U.S. Cl.
USPC .... 424/85.2; 424/184.1; 424/85.1; 424/275.1

(58) Field of Classification Search
CPC .......................... A61K 2039/58; A61K 39/39
See application file for complete search history.

(56) References Cited

U.S. PATENT DOCUMENTS

| 5,073,627 | A | 12/1991 | Curtis et al. |
| 5,885,829 | A | 3/1999 | Mooney et al. |
| 6,251,396 | B1 | 6/2001 | Gaur et al. |
| 6,281,256 | B1 | 8/2001 | Harris et al. |
| 6,403,374 | B1 | 6/2002 | Tsien et al. |
| 6,429,199 | B1 | 8/2002 | Krieg et al. |
| 6,511,650 | B1 | 1/2003 | Eiselt et al. |
| 6,541,022 | B1 | 4/2003 | Murphy et al. |
| 6,642,363 | B1 | 11/2003 | Mooney et al. |
| 6,685,963 | B1 | 2/2004 | Taupin et al. |
| 6,748,954 | B2 | 6/2004 | Lee et al. |
| 6,767,928 | B1 | 7/2004 | Murphy et al. |
| 6,783,712 | B2 | 8/2004 | Slivka et al. |
| 6,790,840 | B1 | 9/2004 | Lee et al. |
| 6,797,738 | B2 | 9/2004 | Harris et al. |
| 6,800,733 | B2 | 10/2004 | Tsien et al. |
| 7,157,566 | B2 | 1/2007 | Tsien et al. |
| 7,186,413 | B2 | 3/2007 | Bouhadir et al. |
| 7,427,602 | B1 | 9/2008 | Shea et al. |
| 7,575,759 | B2 | 8/2009 | Murphy et al. |
| 7,790,699 | B2 | 9/2010 | Melvik et al. |
| 8,067,237 | B2 | 11/2011 | Mooney et al. |
| 2002/0131853 | A1 | 9/2002 | Nagasawa |
| 2002/0150604 | A1 | 10/2002 | Yi et al. |
| 2003/0075822 | A1 | 4/2003 | Slivka et al. |
| 2003/0082806 | A1 | 5/2003 | Berenson et al. |
| 2003/0095994 | A1 | 5/2003 | Geistlich et al. |
| 2003/0100527 | A1 | 5/2003 | Krieg et al. |
| 2004/0063206 | A1 | 4/2004 | Rowley et al. |
| 2004/0136968 | A1 | 7/2004 | Zheng et al. |
| 2004/0151764 | A1 | 8/2004 | Zamora |
| 2004/0220111 | A1 | 11/2004 | Kleinman et al. |
| 2004/0242482 | A1 | 12/2004 | Gehring et al. |
| 2005/0002915 | A1 | 1/2005 | Atala et al. |
| 2005/0053667 | A1 | 3/2005 | Irvine et al. |
| 2005/0079159 | A1 | 4/2005 | Shastri et al. |
| 2005/0106211 | A1 | 5/2005 | Nelson et al. |

(Continued)

FOREIGN PATENT DOCUMENTS

| EP | 0562862 A1 | 9/1993 |
| EP | 1452191 A2 | 9/2004 |

(Continued)

OTHER PUBLICATIONS

Bar-Or et al. (Archives of Neurology. Oct. 2007; 64(10):1407-1415).*
Pedersen et al. (Immunology Letters. 2004; 91:63-69).*
"Antigens and Receptors." *Immunology.* Doan et al., eds. Philadelphia: Wolters Kluwer/Lippincott Williams & Wilsons. (2008):11-23.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171. 10(2003):4984-4989.
Akira et al. "Pathogen Recognition and Innate Immunity." *Cell.* 124. 4(2006):783-801.

(Continued)

*Primary Examiner* — Scott Long
(74) *Attorney, Agent, or Firm* — Mintz Levin Cohn Ferris Glovsky and Popeo, P.C.; Ingrid A. Beattie

(57) ABSTRACT

Biomaterial systems, e.g., gel scaffolds, are used in vivo to recruit immune cells and promote their activation towards a non-inflammatory phenotype, thereby leading suppression of inflammation. The compositions and methods are useful to reduce the severity of autoimmunity, chronic inflammation, allergy, and periodontal disease.

3 Claims, 27 Drawing Sheets

(56) References Cited

U.S. PATENT DOCUMENTS

| | | |
|---|---|---|
| 2005/0154376 A1 | 7/2005 | Riviere et al. |
| 2005/0177249 A1 | 8/2005 | Kladakis et al. |
| 2006/0083712 A1 | 4/2006 | Anversa |
| 2006/0264380 A1 | 11/2006 | Hellstrom et al. |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0178159 A1 | 8/2007 | Chen et al. |
| 2007/0190646 A1 | 8/2007 | Engler et al. |
| 2008/0044900 A1* | 2/2008 | Mooney et al. ............... 435/375 |
| 2008/0044990 A1 | 2/2008 | Lee |
| 2008/0138416 A1 | 6/2008 | Rauh et al. |
| 2008/0206308 A1 | 8/2008 | Jabbari et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0190741 A1 | 7/2010 | Cohen et al. |
| 2010/0272171 A1 | 10/2010 | Harlow et al. |
| 2011/0020216 A1 | 1/2011 | Mooney et al. |
| 2011/0117170 A1 | 5/2011 | Cao et al. |
| 2012/0100182 A1 | 4/2012 | Mooney et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0329791 A1 | 12/2012 | Ashwell et al. |
| 2013/0202707 A1 | 8/2013 | Ali et al. |

FOREIGN PATENT DOCUMENTS

| | | |
|---|---|---|
| EP | 1561481 A2 | 8/2005 |
| WO | WO-9812228 A1 | 3/1998 |
| WO | WO-0135932 A2 | 5/2001 |
| WO | WO-0320884 A2 | 3/2003 |
| WO | WO-2004006990 A2 | 1/2004 |
| WO | WO-2004089413 A1 | 10/2004 |
| WO | WO-2005026318 A2 | 3/2005 |
| WO | WO-2005037190 A2 | 4/2005 |
| WO | WO-2005037293 A1 | 4/2005 |
| WO | WO-2005072088 A2 | 8/2005 |
| WO | WO-2007030901 A1 | 3/2007 |
| WO | WO-2007064152 A1 | 6/2007 |
| WO | WO-2007070660 A2 | 6/2007 |
| WO | WO-2007150020 A1 | 12/2007 |
| WO | WO-2008018707 A1 | 2/2008 |
| WO | WO-2009002401 A2 | 12/2008 |
| WO | WO-2009005769 A2 | 1/2009 |
| WO | WO-2009074341 A1 | 6/2009 |
| WO | WO-2009102465 A2 | 8/2009 |
| WO | WO-2009146456 A1 | 12/2009 |
| WO | WO-2009155583 A1 | 12/2009 |
| WO | WO-2010120749 A2 | 10/2010 |
| WO | WO-2011063336 A2 | 5/2011 |
| WO | WO-2011109834 A2 | 9/2011 |
| WO | WO-2011130753 A2 | 10/2011 |
| WO | WO-2011150240 A1 | 12/2011 |
| WO | WO-2011151431 A1 | 12/2011 |
| WO | WO-2011163669 A2 | 12/2011 |
| WO | WO-2012009611 A2 | 1/2012 |
| WO | WO-2012048165 A2 | 4/2012 |
| WO | WO-2012064697 A2 | 5/2012 |
| WO | WO-2012148684 A1 | 11/2012 |
| WO | WO-2012149358 A1 | 11/2012 |
| WO | WO-2012167230 A1 | 12/2012 |
| WO | WO-2013106852 A1 | 7/2013 |

OTHER PUBLICATIONS

Akira et al. "Toll-Like Receptors: Critical Proteins Linking Innate and Acquired Immunity." *Nat. Immunol.* 2.8(2001):675-680.

Aldhous. "Print Me a Heart and a Set of Arteries." *New Scientist.* 2547(2006):19.

Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).

Ali et al. "Converging Cell Therapy with Biomaterials." *Cell Transplantation from Laboratory to Clinic.* Burlington, MA: Elsevier, Inc. (2006):591-609.

Ali et al. "In situ Regulation of DC Subsets and T Cells Mediates Tumor Regression in Mice." *Sci. Transl. Med.* 1.8(2009):8-19.

Ali et al. "Infection-Mimicking Materials to Program Dendritic Cells in situ." *Nat. Mater.* 8.2(2009):151-158.

Ali et al. "Sustained GM-CSF and PEI Condensed pDNA Presentation Increases the Level and Duration of Gene Expression in Dendritic Cells." *J. Control. Release.* 132.3(2008):273-278.

Allen et al. "Regulation of Satellite Cells During Skeletal Muscle Growth and Development." *Proc. Soc. Exp. Biol. Med.* 194.2(1990):81-86.

Allen et al. "Regulation of Skeletal Muscle Satellite Cell Proliferation by Bovine Pituitary Fibroblast Growth Factor." *Exp. Cell Res.* 152.1(1984):154-160.

Almarza et al. "Evaluation of Three Growth Factors in Combination of Two for Temporomandibular Joint Disc Tissue Engineering." *Arch. Oral Biol.* 51.3(2006):215-221.

Alsberg et al. "Cell-Interactive Alginate Hydrogels for Bone Tissue Engineering." *J. Dent. Res.* 80.11(2001):2025-2029.

Alsberg et al. "Engineering Growing Tissues." *PNAS.* 99.18(2002):12025-12030.

Anderson et al. "The NOD Mouse: A Model of Immune Dysregulation." *Annu. Rev. Immunol.* 23(2005):447-485.

Anderson. "A Role for Nitric Oxide in Muscle Repair: Nitric Oxide-Mediated Activation of Muscle Satellite Cells." *Mol. Biol. Cell.* 11(2000):1859-1874.

Arany et al. "At the Edge of Translation—Materials to Program Cells for Directed Differentiation." *Oral Dis.* 17.3(2011):241-251.

Atala et al. "Endoscopic Treatment of Vesicoureteral Reflux with a Chondrocyte-Alginate Suspension." *J. Urol.* 152(1994):641-643.

Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.

Badovinac et al. "Regulation of CD8 T+ Cells Undergoing Primary and Secondary Responses to Infection in the Same Host." *J. Immunol.* 170(2003):4933-4942.

Bakri et al. "Pharmacokinetics of Intravitreal Bevacizumab (Avastin)." *Ophthalmology.* 114.5(2007):855-859.

Banchereau et al. "Dendritic Cells and the Control of Immunity." *Nature.* 392.6673(1998):245-252.

Barbero et al. "Growth Factor Supplemented Matrigel Improves Ectopic Skeletal Muscle Formation—A Cell Therapy Approach." *J. Cell. Physiol.* 186(2001):183-192.

Barrio et al. "A Two-Dimensional Numerical Study of Spatial Pattern Formation in Interacting Turing Systems." *Bull. Math Biol.* 61.3(1999):483-505.

Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.

Bischoff. "Proliferation of Muscle Satellite Cells on Intact Myofibers in Culture." *Dev. Biol.* 115.1(1986):129-139.

Blanes et al. "Induction of Autoimmune Diabetes by Oral Administration of Autoantigen." *Science.* 274.5293(1996):1707-1709.

Bohl et al. "Role of Synthetic Extracellular Matrix in Development of Engineered Dental Pulp." *J. Biomater. Sci. Polym. Ed.* 9.7(1998):749-764.

Bonauer et al. "MicroRNA-92a Controls Angiogenesis and Functional Recovery of Ischemic Tissues in Mice." *Science.* 324.5935(2009):1710-1713.

Boontheekul et al. "Regulating Myoblast Phenotype Through Controlled Gel Stiffness and Degradation." *Tissue Engin.* 13.7(2007):1431-1442.

Borselli et al. "Functional Muscle Regeneration with Combined Delivery of Angiogenesis and Myogenesis Factors." *PNAS.* 107.8(2010):3287-3292.

Bouhadir et al. "Synthesis of Cross-Linked Poly(aldehyde guluronate) Hydrogels." *Polymer.* 40(1999):3575-3584.

(56) References Cited

OTHER PUBLICATIONS

Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.

Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.

Brouwers et al. "Can the Growth Factors PTHrP, Ihh and VEGF, Together Regulate the Development of a Long Bone?" *J. Biomech.* 39.15(2006):2774-2782.

Burdick et al. "Stimulation of Neurite Outgrowth by Neurotrophins Delivered From Degradable Hydrogels." *Biomater.* 27.3(2006):452-459.

Cao et al. "Promoting Angiogenesis via Manipulation of VEGF Responsiveness with Notch Signaling." *Biomater.* 30.25(2009):4085-4093.

Carlson et al. "Notch Signaling Pathway and Tissue Engineering." *Front. Biosci.* 12(2007):5143-5156.

Carmeliet et al. "Angiogenesis in Cancer and Other Diseases." *Nature.* 407.6801(2000):249-257.

Carmeliet. "Mechanisms of Angiogenesis and Arteriogenesis." *Nat. Med.* 6.4(2000):389-395.

Chan et al. "Antifibrotic Effects of Suramin in Injured Skeletal Muscle After Laceration ." *J. Appl. Physiol.* 95(2003):771-780.

Chan et al. "Helix Induction in Antimicrobial Peptides by Alginate in Biofilms." *J. Biol. Chem.* 279.37(2004):38749-38754.

Chen et al. "Integrated Approach to a Designing Growth Factor Delivery Systems." *FASEB J.* 21.14(2007):3896-3903.

Chen et al. "Polymeric Growth Factor Delivery Strategies for Tissue Engineering." *Pharma. Res.* 20.8(2003):1103-1112.

Chen et al. "Skeletal Muscle Stem Cells." *Reprod. Biol. Endocrinol.* 1(2003):101.

Chen et al. "Spatio-Temporal VEGF and PDGF Delivery Patterns Blood Vessel Formation and Maturation." *Pharm. Res.* 24.2(2007):258-264.

Choi. "Replacement Organs, Hot Off the Press." *New Scientist.* 177. 2379(2003):16.

Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.

Clauss et al. "Interstitial Transport of Rabbit and Sheep Antibodies in Normal and Neoplastic Tissues." *Cancer Res.* 50.12(1990):3487-3492.

Cohen et al. "Controlled Delivery Systems for Proteins Based on Poly(Lactic/Glycolic Acid) Microspheres." *Pharm. Res.* 8.6(1991):713-720.

Conboy et al. "The Regulation of Notch Signaling Controls Satellite Cell Activation and Cell Fate Determination in Postnatal Myogenesis." *Dev. Cell.* 3.3(2002):397-409.

Conn et al. "Purification of a Glycoprotein Vascular Endothelial Cell Mitogen from a Rat Glioma-Derived Cell Line." *PNAS.* 87.4(1990):1323-1327.

Cooper et al. "Extended Amplification In Vitro and Replicative Senescence: Key Factors Implicated in the Success of Human Myoblast Transplantation." *Hum. Gene Ther.* 14(2003):1169-1179.

Cornelison et al. "Single-Cell Analysis of Regulatory Gene Expression in Quiescent and Activated Mouse Skeletal Muscle Satellite Cells." *Dev. Biol.* 191.2(1997):270-283.

Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1(2001):79-94.

Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.

Curiel et al. "Tumor Immunotherapy: Inching Toward the Finish Line." *J. Clin. Invest.* 109.3(2002):311-312.

D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.

Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.

De Temmerman et al. "Particulate Vaccines: On the Quest for Optimal Delivery and Immune Response." *Drug Disc. Today.* 16.13/14(2011):569-582.

den Haan et al. "CD8+ by not CD8- Dendritic Cells Cross-Prime Cytotoxic T Cells in Vivo." *J. Exp. Med.* 192.12(2000):1685-1696.

Dennis et al. "Excitability and Contractility of Skeletal Muscle Engineered From Primary Cultures and Cell Lines." *Am. J. Physiol. Cell Physiol.* 280(2001):C288-C295.

Dennis et al. "Excitability and Isometric Contractile Properties of Mammalian Skeletal Muscle Constructs Engineered in vitro." *In Vitro Cell Dev. Biol. Anim.* 36.5(2000):327-335.

Dieu et al. "Selective Recruitment of Immature and Mature Dendritic Cells by Distinct Chemokines Expressed in Different Anatomic Sites." *J. Exp. Med.* 188.2(1988):373-386.

Dor et al. "Making Vascular Networks in the Adult: Branching Morphogenesis Without a Roadmap." *Trends Cell Biol.* 13.3(2003):131-136.

Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.

Dranoff. "Cyotkines in Cancer Pathogenesis and Cancer Therapy." *Nat. Rev. Cancer.* 4.1(2004):11-22.

Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.

Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.

Eiselt et al. "Porous Carriers for Biomedical Applications Based on Alginate Hydrogels." *Biomat.* 21.19(2000):1921-1927.

El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J.* 34.2(2008):52-67.

Eldar et al. "Elucidating Mechanisms Underlying Robustness of Morphogen Gradients." *Curr. Opin. Genet. Dev.* 14.4(2004):435-439.

Eldar et al. "Robustness of the BMP Morphogen Gradient in *Drosophila* Embryonic Patterning." *Nature.* 419.6904(2002):304-308.

Eldar et al. "Self-Enhanced Ligand Degradation Underlies Robustness of Morphogen Gradients." *Dev. Cell.* 5.4(2003):635-646.

Engler et al. "Matrix Elasticity Directs Stem Cell Lingeage Specification." *Cell.* 126.4(2006):677-689.

Ennett et al. "Temporally Regulated Delivery of VEGF in vitro and in vivo." *J. Biomed. Mater. Res. A.* 79.1(2006):176-184.

Faissner et al. "Boundaries and Inhibitory Molecules in Developing Neural Tissues." *Glia.* 13.4(1995):233-254.

Farrar et al. "T Helper Subset Development: Roles of Instruction, Selection, and Transcription." *J. Clin. Invest.* 109.4(2002):431-435.

Ferrara et al. "Angiogenesis as a Therapeutic Target." *Nature.* 438. 7070(2005):967-974.

Ferrara et al. "Discovery and Development of Bevacizumab, an Anti-VEGF Antibody for Treating Cancer." *Nat. Rev. Drug Discov.* 3.5(2004):391-400.

Folkman. "Angiogenesis." *Annu. Rev. Med.* 57(2006):1-18.

Fonseca et al. "Capitalizing on the Immunogenicity of Dying Tumor Cells." *Clin. Cancer Res.* 14.16(2008):1603-1608.

Fontaine et al. "Surgical Treatment of Peripheral Circulation Disorders." *Helv. Chir. Acta*21.56(1954):499-533. (German Original, No English Translation Available).

(56) References Cited

OTHER PUBLICATIONS

Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG46721.1, Jun. 29, 2004.
GenBank Accession No. CBI71013.1, Feb. 2, 2010.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.* 130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol* 39(1995):845-854.
Gussoni et al. "Dystophin Expression and in the *mdx* Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *Pnas.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts Can Give Rise to Functional Satellite Cells as Identified Using the Myf5nlacZl+ Mouse." *Gene Ther.* 8(2001):778-783.

(56) References Cited

OTHER PUBLICATIONS

Hildner et al. "Batf3 Deficiency Reveals a Critical Role for CD8β+ Dendritic Cells in Cytotoxic T Cell Immunity." Science. 322.5904(2008):1097-1100.
Hill et al. "Designing Scaffolds to Enhance Transplanted Myoblast Survival and Migration." Tissue Engin. 12.5(2006):1295-1304.
Hill et al. "Muscle Satellite (Stem) Cell Activation During Local Tissue Injury and Repair." J. Anat. 203.1(2003):89-99.
Hill. "Macroporous Scaffold Architecture, Peptide, HGF/FGF and Myoblast Incorporation Enhance Myogenesis." IADR/AADR/CADR 83rd General Session. (Mar. 9-12, 2005). Poster #2829.
Hirano et al. "Peptide and Protein Presenting Materials for Tissue Engineering." Adv. Mat. 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." PNAS. 95.23(1998):13806-13811.
Hodi et al. "Immunologic and Clinical Effects of Antibody Blockade of Cytotoxic T Lymphocyte- Associated Antigen 4 in Previously Vaccinated Cancer Patients." PNAS. 105.8(2008):3005-3010.
Horsley et al. "IL-4 Acts as a Myoblast Recruitment Factor During Mammalian Muscle Growth." Cell. 113.4(2003):483-494.
Hsiong et al. "Differentiation Stage Alters Matrix Control of Stem Cells." J. Biomed. Mater. Res. Part A. 8(2007):145-456.
Huang et al. "Fabrication and in vitro Testing of Polymeric Delivery Systems for Condensed DNA." J. Biomed. Mater. Res. 67(2003):1384-1392.
Huang et al. "Long-Term In Vivo Gene Expression via Delivery of PEI-DNA Condensates From Porous Polymer Scaffolds." Hum. Gene Ther. 16.5(2005):609-617.
Hubbell et al. "Materials Engineering for Immunomodulation." Nature. 462(2009):449-460.
Hubbell. "Biomaterials in Tissue Engineering." Bio/Tech. 13(1995):565-576.
Huebsch et al. "Harnessing Traction-Mediated Manipulation of the Cell/Matrix Interface to Control Stem-Cell Fate." Nat. Mater. 9.6(2010):518-526.
Ishihara et al. "Roles of Bradykinin in Vascular Permeability and Angiogenesis in Solid Tumor." Int. Immunopharmacol. 2.4(2002):499-509.
Jain. "Molecular Regeneration of Vessel Maturation." Nat. Med. 9.6(2003):685-693.
Jain. "The Manufacturing Techniques of Various Drug Loaded Biodegradable Poly(lactide-co-glycolide) (PLGA) Devices." Biomater. 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." Immunity. 16.3(2002):429-439.
Jego et al. "Plasmacytoid Dendritic Cells Induce Plasma Cell Differenetiation Through Type I Interferon and Interleukin 6." Immunity. 19.2(2003):225-234.
Jiang et al. "Self-Organization of Periodic Patterns by Dissociated Feather Mesenchymal Cells and the Regulation of Size, Number and Spacing of Primorida." Development. 126.22(1999):4997-5009.
Jinushi et al. "Enhancing the Clinical Activity of Granulocyte-Macrophage Colony-Stimulating Factor-Secreting Tumor Cell Vaccines." Immunol. Rev. 222(2008):287-298.
Jinushi et al. "MFG-E8-Mediated Uptake of Apoptotic Cells by APCs Links the Pro- and Antiinflammatory Activities of GM-CSF." J. Clin. Invest. 117.7(2007):1902-1913.
Johnson et al. "Activation of Skeletal Muscle Satellite Cells and the Role of Fibroblast Growth Factor Receptors." Exp. Cell Res. 219.2(1995):449-453.
Kanzler et al. "Therapeutic Targeting of Innate Immunity with Toll-Like Receptor Agaonists and Antagonists." Nat. Med. 13.5(2007):552-559.
Kawai et al. "Innate Immune Recognition of Viral Infection." Nat. Immunol. 7.2(2006):131-137.
Kawashima et al. "Pulmonary Delivery of Insulin with Nebulized DL-Lactide/Glycolide copolymer (PLGA) Nanospheres to Prolong Hypoglycemic Effect." J. Control Release. 62.1-2(1999):279-287.
Kim et al. "An Overview of Cartilage Tissue Engineering." Yonsei Med. J. 41.6(2000):766-773.
Kinoshita et al. "Successive Injections in MDX Mice of Myoblasts Grown with bFGF." Neuromusc. Disord. 6.3(1996):187-193.
Kisak et al. "The Vesosome—A Multicompartment Drug Delivery Vehicle." Curr. Med. Chem. 11.2(2004):199-219.
Klebanoff et al. "CD8+ T-Cell Memory in Tumor Immunology and Immunotherapy." Immunol. Rev. 211(2006):214-224.
Klinman. "Immunotherapeutic Uses of CpG Oligodeoxynucleotides." Nat. Rev. Immunol. 4.4(2004):249-258.
Kondo et al. "A Reaction-Diffusion Wave on the Skin of the Marine Angelfish Pomacanthus." Nature. 376(2002):765-768.
Kong et al. "Controlling Rigidity and Degradation of Alginate Hydrogels via Molecular Weight Distribution." Biomacromolec. 5.5(2004):1720-1727.
Kong et al. "Designing Alginate Hydrogels to Maintain Viability of Immobilized Cells." Biomat. 24.22(2003):4023-4029.
Kong et al. "Non-Viral Gene Delivery Regulated by Stiffness of Cell Adhesion Substrates." Nat. Mater. 4(2005):406-410.
Krieg. "Development of TLR9 Agonists for Cancer Therapy." J. Clin. Invest. 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." Nat. BioTechnol. 20.1(2002):64-69.
Kumar et al. "Toll-Like Receptors and Innate Immunity." Biochem. Biophys. Res. Commun. 388.4(2009):621-625.
Kurts et al. "CD8 T Cell Ignorance or Tolerance to Islet Antigens Depends on Antigen Dose." PNAS. 96.22(1999):12703-12707.
Kwon et al. "In vivo Targeting Dendritic Cells for Activation of Cellular Immunity Using Vaccine Carriers Based on pH-Responsive Microparticles." PNAS. 102.51(2005):18264-18268.
Langer et al. "Tissue Engineering." Science. 260(1993):920-926.
Lanzavecchia et al. "Regulation of T Cell Immunity by Dendritic Cells." Cell. 106.3(2001):263-266.
Leach et al. "Coating of VEGF-Releasing Scaffolds with Bioactive Glass for Angiogenesis and Bone Regeneration." Biomater. 27.17(2006):3249-3255.
Lee et al. "Hydrogel Formation via Vell Crosslinking." Adv. Mat. 15.21(2003):1828-1832.
Lee et al. "Hydrogels for Tissue Engineering." Chem. Rev. 101.7(2001):1869-1879.
Lefaucheur et al. "The Cellular Events of Injured Muscle Regeneration Depend on the Nature of the Injury." Neuromusc. Disorders. 5.6(1995):501-509.
Lensch et al. "Scientific and Clinical Opportunities for Modeling Blood Disorders With Embryonic Stem Cells." Blood. 107.7(2006):2605-2612.
Leshem et al. "Hepatocyte Growth Factor (HGF) Inhibits Skeletal Muscle Cell Differentiation: A Role for the bHLH Protein Twist and the cdk Inhibitor p27." J. Cell. Physiol. 184(2000):101-109.
Li et al. "Effect of Growth Factors and Extracellular Matrix Materials on the Proliferation and Differentiation of Microencapsulated Myoblasts." J. Biomater. Sci. Polym. Ed. 14.6(2003):533-549.
Li et al. "Effects of Three-Dimensional Scaffolds on Cell Organization and Tissue Development." Biotech. Bioprocess Eng. 6.5(2001):311-325.
Li. "TNF-α is a Mitogen is Skeletal Muscle." Am. J. Physiol. Cell Physiol. 285(2003):C370-C376.
Lipton et al. "Developmental Fate of Skeletal Satellite Cells." Science. 205(1979):1292-1294.
Liu. "Dendritic Cell Subsets and Lineages, and Their Functions in Innate and Adaptive Immunity." Cell. 106.3(2001):259-262.

(56) References Cited

OTHER PUBLICATIONS

Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292.5520(2001):1389-1394.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin $\alpha v \beta 3$-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-$\beta$ Superfamily Member." *Nature.* 387(1997):83-90.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor $\beta$ Gene Expression in Respiratory and Peripheral Muscles." *Arch. Bronconeumol.* 38.7(2002):311-316. (Spanish Original and English Abstract).
Partridge et al. "Conversion of mdx Myofibres From Dystrophin-Negative to -Positive by Injection of Normal Myoblasts." *Nature.* 337(1989):176-179.
Pelinkovic et al. "Tissue Engineering and Gene Therapy of the Muscoskeletal System with Muscle Cells." *Z. Orthop. Ihre Grenzgeb.* 138.5(2000):402-406.
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.

(56) References Cited

OTHER PUBLICATIONS

Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.*10(1998):366. (Abstract #153.07).
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci Polym. Ed.* 15.12(2004):1561-1570.
Ridgway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity in vitro and in vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Facilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Salvador et al. "Combination of Immune Stimulating Adjuvants With Poly(lactide-co-glycolide) Microspheres Enhances the Immune Response of Vaccines." *Vaccine.* 30.3(2011):589-596.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell.* 102.6(2000):777-786.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Skokos et al. "CD8- DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Sustained Vascular Endothelial Growth Factor Delivery Enhances Angiogenesis and Perfusion in Ischemic Hind Limb." *Pharm. Res.* 22.7(2005):1110-1116.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.
Tatsumi et al. "HGF/SF is Present in Normal Adult Skeletal Muscle and is Capable of Activating Satellite Cells." *Dev. Biol.* 194.1(1998):114-128.
Thurston et al. "The Delta Paradox: DLL4 Blockade leads to more Tumour Vessels but Less Tumour Growth." *Nat. Rev. Cancer.* 8.5(2007):327-331.
Tidball. "Inflammatory Cell Response to Acute Muscle Injury." *Med. Sci. Sports Exerc.* 27.7(1995):1022-1032.
Turing. "Discussion: Turing's Theory of Morphogenesis—Its Influence on Modelling Biological Pattern and Form." *Bull. Math. Biol.* 52.1-2(1990):119-159.

(56) References Cited

OTHER PUBLICATIONS

Turing. "The Chemical Basis of Morphogenesis." *Philosophical Transactions of the Royal Society of London. Series B*. 237.641(1952):37-72.
Uchida et al. "Immunization by Particle Bombardment of Antigen-Loaded poly-(DL-lactide-co-glycolide) Microspheres in Mice." *Vaccine*. 12(2006):2120-2130.
Urbanek et al. "Stem Cell Niches in the Adult Mouse Heart." *PNAS*. 103.24(2006):9226-9231.
van Duin et al. "Triggering TLR Signaling in Vaccination." *Trends Immunol*. 27.1(2006):49-55.
Vandenburgh et al. "Tissue-Engineered Skeletal Muscle Organoids for Reversible Gene Therapy." *Hum. Gene Ther*. 17(1996):2195-2200.
Vieira et al. "The Bulk of Endogenously Produced IgG2a is Eliminated From the Serum of Adult C57BL/6 Mice With a Half-Life of 6-8 Days." *Eur. J. Immunol*. 16.7(1986):871-874.
Vieira et al. "The Half-Lives of Serum Immunoglobulins in Adult Mice." *Eur. J. Immunol*. 18.2(1988):313-316.
Villadangos et al. "Intrinsic and Cooperative Antigen-Presenting Functions of Dendritic-Cell Subsets in vivo." *Nat. Rev. Immunol*. 7.7(2007):543-555.
Villadangos. "Presentation of Antigens by MHC Class II Molecules: Getting the Most Out of Them." *Molec. Immunol*. 38.5(2001):329-346.
von Dassow et al. "The Segment Polarity Network is a Robust Developmental Module." *Nature*. 406.6792(2000):188-192.
Wakim et al. "Dendritic Cell-Induced Memory T Cell Activation in Nonlymphoid Tissues." *Science*. 319(2008):198-202.
Waldron-Lynch et al. "Advances in Type 1 Diabetes Therapeutics: Immunomodulation and β-Cell Savage." *Endocrinol. Metab. Clin. North Am*. 38.2(2009):303-317.
Wan et al. "Peritoneal Macrophage Uptake, Pharmacokinetics and Biodistribution of Macrophage-Targeted PEG-fMLF (*N*-Formyl-Methionyl-Leucyl-Phenylalanine) Nanocarriers for Improving HIV Drug Delivery." *Pharm. Res*. 24.11(2007):2110-2119.
Wang et al. "Biological Activity of Bevacizumab, a Humanized Anti-VEGF Antibody in vitro." *Angiogenesis*. 7.4(2004):335-345.
Wei et al. "Global Mapping of H3K4me3 and H3K27me3 Reveals Specificity in Plasticity in Lineage Fate Determination of Differentiating CD4+ T Cells." *Immunity*. 30.1(2009):155-167.
Wernig et al. "Function of Skeletal Muscle Tissue Formed After Myoblast Transplantation into Irradiated Mouse Muscles." *J. Physiol*. 522.2(2000):333-345.
White et al. "Leukemia Inhibitory Factor Enhances Regeneration in Skeletal Muscles After Myoblast Transplantation." *Musc. Nerve*. 24.5(2001):695-697.
World Health Organization. "Global Burden of Musculoskeletal Disease Revealed in new WHO Report." *Bull. World Health Organ*. 81.11(2003):853-854.
World Health Organization. "The World Health Report 2004: Changing History." *The World Health Report*. (2004):1-169.
Wright et al. "Muscle-Based Gene Therapy and Tissue Engineering for the Musculoskeletal System." *Drug Disc. Today*. 6.14(2001):728-733.
Yancopoulos et al. "Vascular-Specific Growth Factors and Blood Vessel Formation." *Nature*. 407.6801(2000):242-248.
Yuen et al. "Mimicking Nature by Codelivery of Stimulant and Inhibitor to Create Temporally Stable and Spatially Restricted Angiogenic Zones." *PNAS*. 107.42(2010):17933-17938.
Zammit et al. "Kinetics of Myoblast Proliferation Show That Resident Satellite Cells are Competent to Fully Regenerate Skeletal Muscle Fibers." *Exp. Cell Res*. 281.1(2002):39-49.
Zammit et al. "Muscle Satellite Cells Adopt Divergent Fates: A Mechanism for Self-Renewal?" *J. Cell Biol*. 166.3(2004):347-357.
Zeltinger et al. "Effect of Pore Size and Void Fraction on Cellular Adhesion, Proliferation, and Matrix Deposition." *Tissue Eng*. 7.5(2001):557-572.
Zhang et al. "A Comparative Study of the Antigen-Specific Immune Response Induced by Co-Delivery of CpG OGN and Antigen Using Fusion Molecules or Biodegradable Microparticles." *J. Pharma. Sci*. 98.12(2007):3283-3292.
Zhao et al. "Active Scaffolds for On-Demand Drug and Cell Delivery." *PNAS*. 108.1(2011):67-72.
Zhao et al. "Directed Cell Migration via Chemoattractants Released from Degradable Microspheres." *Biomat*. 26(2005):5048-5063.
Zhou et al. "Microstructure and Mechanical Properties of Poly(L-lactide) Scaffolds Fabricated by Gelatin Particle Leaching Method." *J. Appl. Polymer Sci*. 98(2005):1373-1379.
"Wound Management: Past, Present, and Future." *Clinicians' Pocket Guide to Chronic Wound Repair*. Mulder et al., eds. Springhouse, PA: Springhouse Corporation. (1998):85-90.
Anderson et al. "Biomaterial Microarrays: Rapid, Microscale Screening of Polymer-Cell Interaction." *Biomaterials*. 26.23(2005):4892-4897.
Anderson et al. "Nanoliter-Scale Synthesis of Arrayed Biomaterials and Application to Human Embryonic Stem Cells." *Nat. Biotechnol*. 22.7(2004):863-866.
Bachem et al. "Superior Antigen Cross-Presentation and XCR1 Expression Define Human CD11c+CD141+ Cells as Homologues of Mouse CD8+ Dendritic Cells." *J. Exp. Med*. 207.6(2010):1273-1281.
Balakrishna et al. "Structural Correlates of Antibacterial and Membrane-Permeabilizing Activities in Acylpolyamines." *Antimicrob. Agents Chemother*. 50.3(2006):852-861.
Bar-Cohen et al. "Electroactive Polymer Actuators and Sensors." *MRS Bullet*. 33.3(2008):173-181.
Bates. "Improved Muscle Regeneration by Combining VEGF With IGF1." *Regen. Med*. 5.6(2010):853-854.
Beaucage et al. "The Functionalization of Oligonucleotides Via Phosphoramidite Derivatives." *Tetrahedron*. 49.10(1993):1925-1963.
Beebe et al. "Functional Hydrogel Structures for Autonomous Flow Control Inside Microfluidic Channels." *Nature*. 404(2000):588-590.
Bekiari et al. "Study of Poly(N,N-dimethylacrylamide)/CdS Nanocomposite Organic/Inorganic Gels." *Langmuir*. 20.19(2004):7972-7975.
Blumenthal et al. "Polyurethane Scaffolds Seeded with Genetically Engineered Skeletal Myoblasts: A Promising Tool to Regenerate Myocardial Function." *Artificial Organs*. 34.2(2010):E46-E54.
Brinkmann et al. "Neutrophil Extracellular Traps Kill Bacteria." *Science*. 303.5663(2004):1532-1535.
Calvert. "Electroactive Polymer Gels." *Electroactive Polymer (EAP) Acutators as Artificial Muscle: Reality, Potential, and Challenges*. Bar-Cohen, ed. Bellingham, WA: Spie Press. (2004):151-170.
Calvert. "Gel Sensors and Actuators." *MRS Bullet*. 33.3(2008):207-212.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res*. 89A.2(2009):304-316.
Coulson et al. "Flow of Fluids through Granular Beds and Packed Columns." *Chemical Engineering*. New York: Pergamon Press. 2(1978):125-171.
Crameri et al. "Improved Green Fluorescent Protein by Molecular Evolution Using DNA Shuffling." *Nat. Biotechnol*. 14.3(1996):315-319.
Doan et al. "Subcellular Localization of a Sporulation Membrane Protein is Achieved Through a Network of Interactions Along and Across the Septum." *Mol. Microbiol*. 55.6(2005):1767-1781.
Egholm et al. "Peptide Nucleic Acids (PNA). Oligonucleotide Analogues with an Achiral Peptide Backbone." *J. Am. Chem. Soc*. 114. 5(1992):1895-1897.
Egholm et al. "PNA Hybridizes to Complementary Oligonucleotides Obeying the Watson-Crick Hydrogen-Bonding Rules," *Nature*. 365. 6446(1993):566-568.
Falsey et al. "Peptide and Small Molecule Microarray for High Throughput Cell Adhesion and Functional Assays." *Bioconjug. Chem*. 12.3(2001):346-353.
Fischer et al. "A Brilliant Monomeric Red Fluorescent Protein to Visualize Cytoskeleton Dynamics in Dictyostelium." *FEBS Lett*. 577.1-2(2004):227-232.

(56) References Cited

OTHER PUBLICATIONS

Fischer et al. "Visualizing Cytoskeleton Dynamics in Mammalian Cells Using a Humanized Variant of Monomeric Red Fluorescent Protein." *FEBS Lett.* 580.10(2006):2495-2502.

Fox. "Management of Worsening Multiple Sclerosis with Mitoxantrone: A Review." *Clin. Ther.* 28.4(2006):461-474.

GenBank Accession No. AAI44040, Mar. 18, 2009.

GenBank Accession No. CAG29322.1, Oct. 16, 2008.

GenBank Accession No. CAG33149.1, Oct. 21, 2008.

GenBank Accession No. EF064765.1, Nov. 13, 2006.

Glasbey et al. "Image Analysis and Three-Dimensional Modelling of Pores in Soil Aggregates." *Eur. J. Soil Sci.* 42.2(1991):479-486.

Gupta et al. "Magnetically Controlled Targeted Micro-Carrier Systems." *Life Sci.* 44.3(1989):175-186.

Heath. "Cells for Tissue Engineering." *Trends Biotechnol.* 18.1(2006):17-19.

Iwamoto et al. "Preparation of an Ionic Polymer Gel Microactuator and Measurement of its Periodic Motions." *Nippon Kagaku Kaishi.* 9(1997):609-614. (Japanese Original and English Abstract).

Juntanon et al. "Electrically Controlled Release of Sulfosalicylic Acid from Crosslinked Poly(Vinyl Alcohol) Hydrogel." *Int. J. Pharm.* 356(2008):1-11.

Khownium et al. "Novel Endotoxin-Compounds with Terephthalaldehyde-bis-guanyllhydrazone Scaffolds." *Bioorg. Med. Chem. Lett.* 16(2006):1305-1308.

Kim et al. "The Effect of VEGF on the Myogenic Differentiation of Adipose Tissue Derived Stem Cells Within Thermosensitive Hydrogel Matrices." *Biomaterials.* 31.6(2010):1213-1218.

Kwon et al. "Electrically Erodible Polymer Gel for Controlled Release of Drugs." *Nature.* 354(1991):291-293.

Lao et al. "Magnetic and Hydrogel Composite Materials for Hyperthermia Applications." *J. Mater. Sci. Mater. Med.* 15.10(2004):1061-1064.

Lauterbach et al. "Mouse CD8α+ DCs and Human BDCA3+ DCs are Major Producers of IFN-λ in Response to Poly IC." *J. Exp. Med.* 207.12(2010):2703-2717.

Letsinger et al. "Phosphoramidate Analogs of Oligonucleotides." *J. Org. Chem.* 35.11(1970):3800-3803.

Liu et al. "Nanostructured Materials Designed for Cell Binding and Transduction." *Biomacromolecules.* 2.2(2001):362-368.

López et al. "Magnetic Applications of Polymer Gels." *Macromol. Symp.* 166.1(2001):173-178.

Meier et al. "Peptide Nucleic Acids (PNAs)—Unusual Properties of Noionic Oligonucleotide Analogues." *Angew. Chem. Int. Ed.* 31.8(1992):1008-1010.

Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).

Miller et al. "Lipopolysaccharide Sequestrants: Structural Correlates of Activity and Toxicity in Novel Acylhomospermines." *J. Med. Chem.* 48(2005):2589-2599.

Miyata et al. "Biomolecule-Sensitive Hydrogels." *Adv. Drug Deliv. Rev.* 54.1(2002):79-98.

Murdan. "Electro-Responsive Drug Delivery from Hydrogels." *J. Control. Release.* 92(2003):1-17.

Nagai et al. "A Variant of Yellow Fluorescent Protein with Fast and Efficient Maturation for Cell-Biological Applications." *Nat. Biotechnol.* 20.1(2002):87-90.

NCBI Accession No. NM_004119, Apr. 14, 2013.

NCBI Accession No. NM_006274.2, Mar. 31, 2013.

Niamlang et al. "Electrically Controlled Release of Salicylic Acid from poly(p-phenylene vinylene) Polyacrylamide Hydrogels." *Int. J. Pharm.* 371(2009):126-133.

Orner et al. "Arrays for the Combinatorial Exploration of Cell Adhesion." *J. Am. Chem. Soc.* 126.35(2004):10808-10809.

Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.

Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.

Porter et al. "Separation of Natural Populations of Coliform Bacteria from Freshwater and Sewage by Magnetic-Bead Cell Sorting." *J. Microbiol. Meth.* 33.3(1998):221-226.

Qui et al. "Environment-Sensitive Hydrogels for Drug Delivery." *Adv. Drug Deliv. Rev.* 53.3(2001):321-339.

Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.

Rizzo et al. "An Improved Cyan Fluorescent Protein Variant Useful for FRET." *Nat. Biotechnol.* 22.4(2004):445-449.

Salvay et al. "Inductive Tissue Engineering with Protein and DNA-Releasing Scaffolds." *Mol. Biosyst.* 2.1(2006):36-48.

Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.

Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.

Takahashi et al. "Induction of Pluripotent Stem Cells from Adult Human Fibroblasts by Defined Factors." *Cell.* 131.5(2007):861-872.

Tanaka et al. "Collapse of Gels in an Electric Field." *Science.* 218(1982):467-469.

ten Dijke et al. "Growth Factors for Wound Healing." *Nat. Biotechnol.* 7(1989):793-798.

Tomer et al. "Electrically Controlled Release of Macromolecules from Cross-Linked Hyaluronic Acid Hydrogels." *J. Control. Release.* 33.3(1995):405-413.

Tourniaire et al. "Polymer Microarrays for Cellular Adhesion." *Chem. Commun.* 20(2006):2118-2120.

Tsien. "The Green Fluorescent Protein." *Annu. Rev. Biochem.* 67(1998):509-544.

Wang et al. "Evolution of New Nonantibody Proteins via Iterative Somatic Hypermutation." *PNAS.* 101.48(2004):16745-16749.

Xie et al. "Preparation and Application of Surface-Coated Superparamagnetic Nanobeads in the Isolation of Genomic DNA." *J. Magn. Magnetic Mater.* 277.1(2004):16-23.

Yu et al. "Induced Pluripotent Stem Cell Lines Derived from Human Somatic Cells." *Science.* 318.5858(2007):1917-1920.

Yuk et al. "Electric Current-Sensitive Drug Delivery System Using Sodium Alginate/Polyacrylic Acid Composites." *Pharm. Res.* 9.7(1992):955-957.

Abrahams et al. "Expression and Secretion of Antiviral Factors by Trophoblast Cells following Stimulation by the TLR-3 Agonist, Poly (I:C)" *Human Reproduction* 21(9):2432-2439 (2006).

Schaefer et al. Innate Immunity in the Human Female Reproductive Tract: Antiviral Response of Uterine Epithelial Cells to TLR3 Agonist Poly(I:C). *J. Immunol.* 174:992-1002 (2005).

* cited by examiner

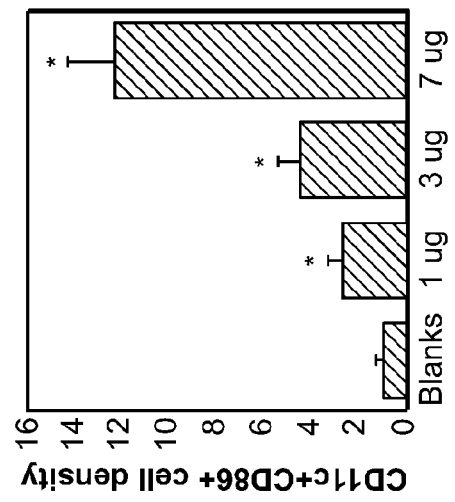
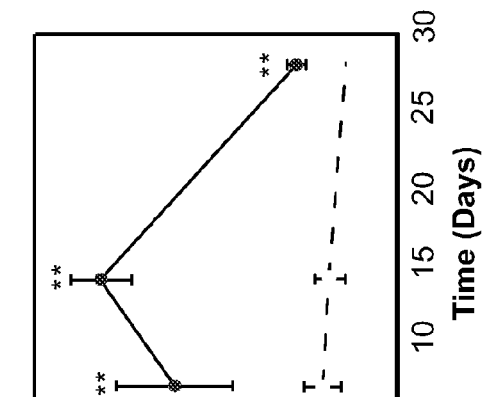
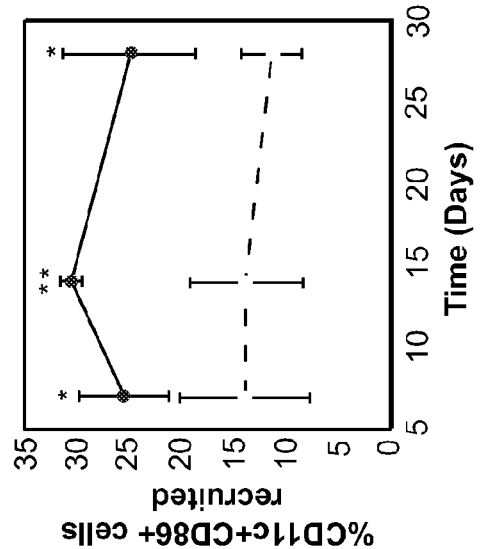
FIG. 4D
FIG. 4E
FIG. 4F

Table 1

Proportionality and phenotypes of CD11+ DC induced *in vitro* from bone marrow cells

| % in all MNC | Control | GM-CSF alone | GM-CSF + TSLP | GM-CSF + VIP | GM-CSF + TGF-b |
|---|---|---|---|---|---|
| CD11c+/Class-II+ | 5.9 | 15.0 | 13.7 | 14.1 | 7.9 |
| CD11c+/CD86+ | 6.4 | 14.7 | 14.6 | 14.6 | 10.5 |
| CD11c+/CD103+ | 1.9 | 2.7 | 3.1 | 3.7 | 6.7 |
| CD11c+/CD209+ | 8.4 | 12.1 | 15.2 | 21.5 | 17.7 |

1) Vertical bone loss of human patient with PD
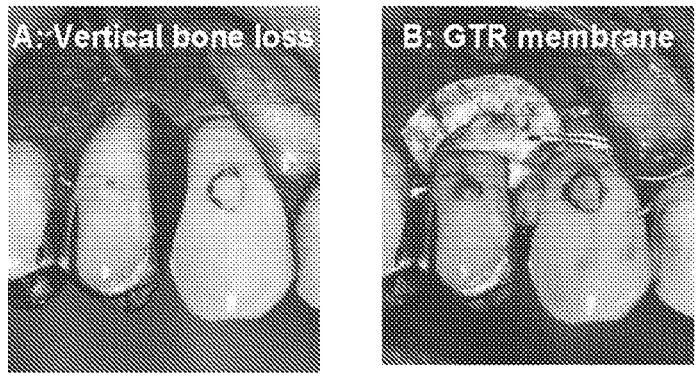
2) Vertical bone loss of mouse model of PD
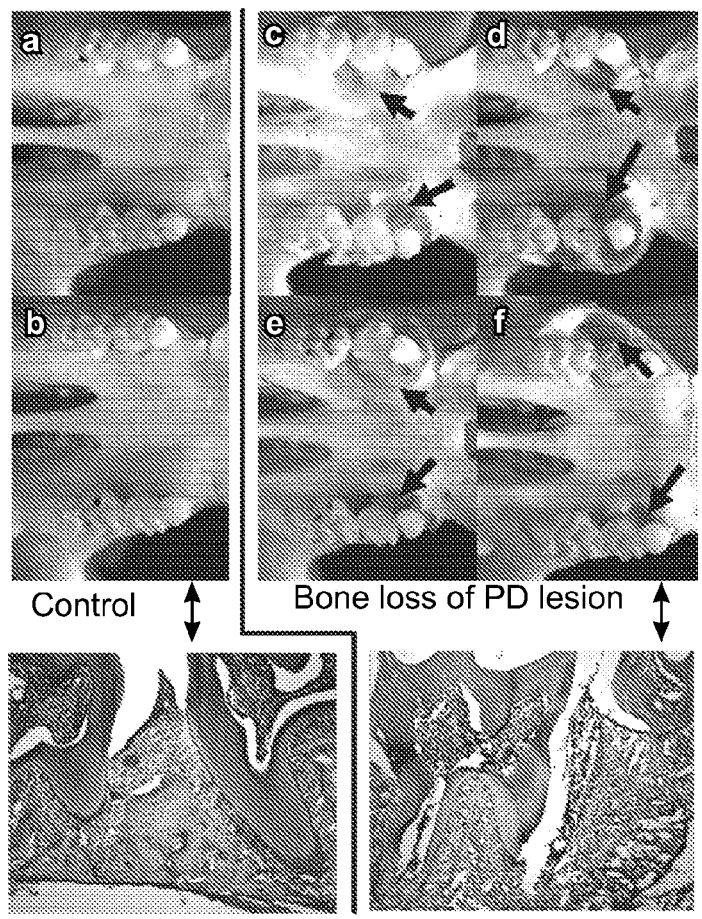
FIG. 7

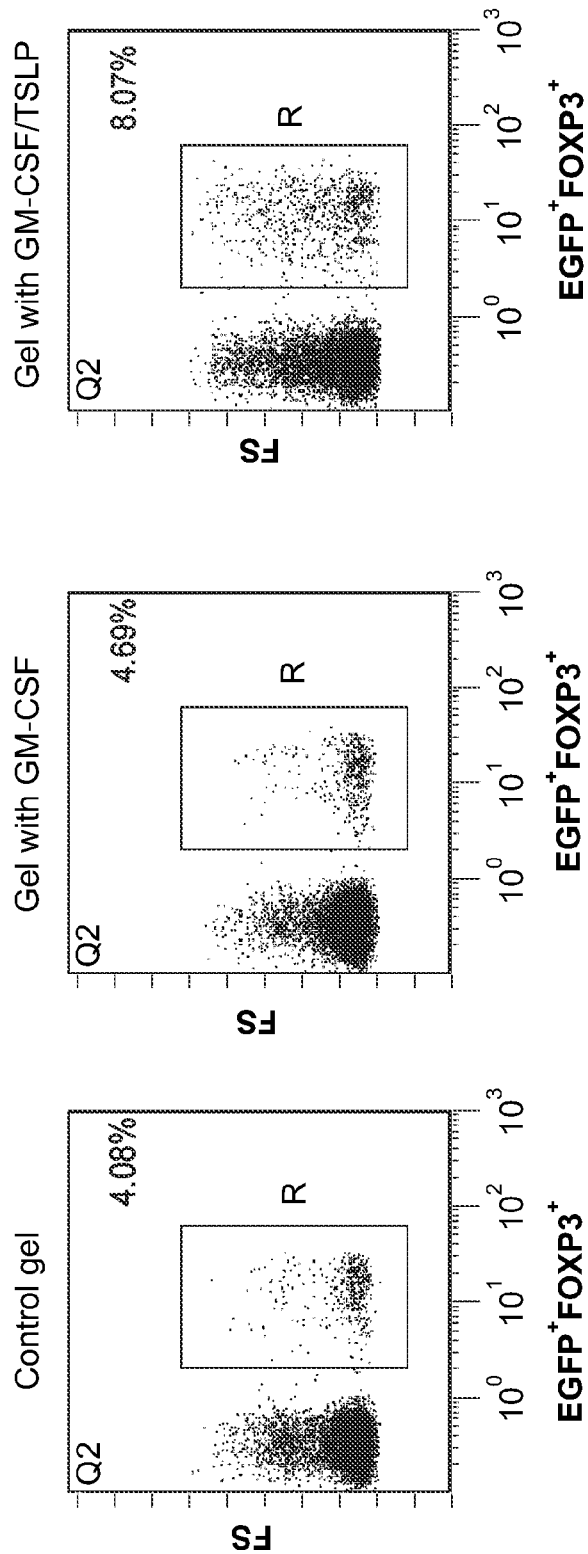

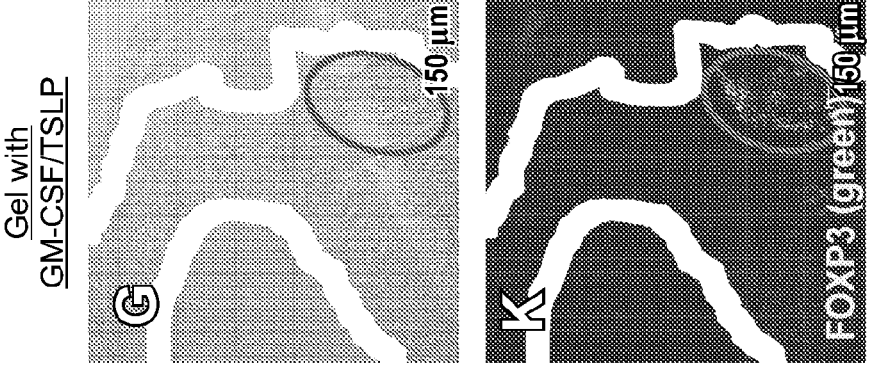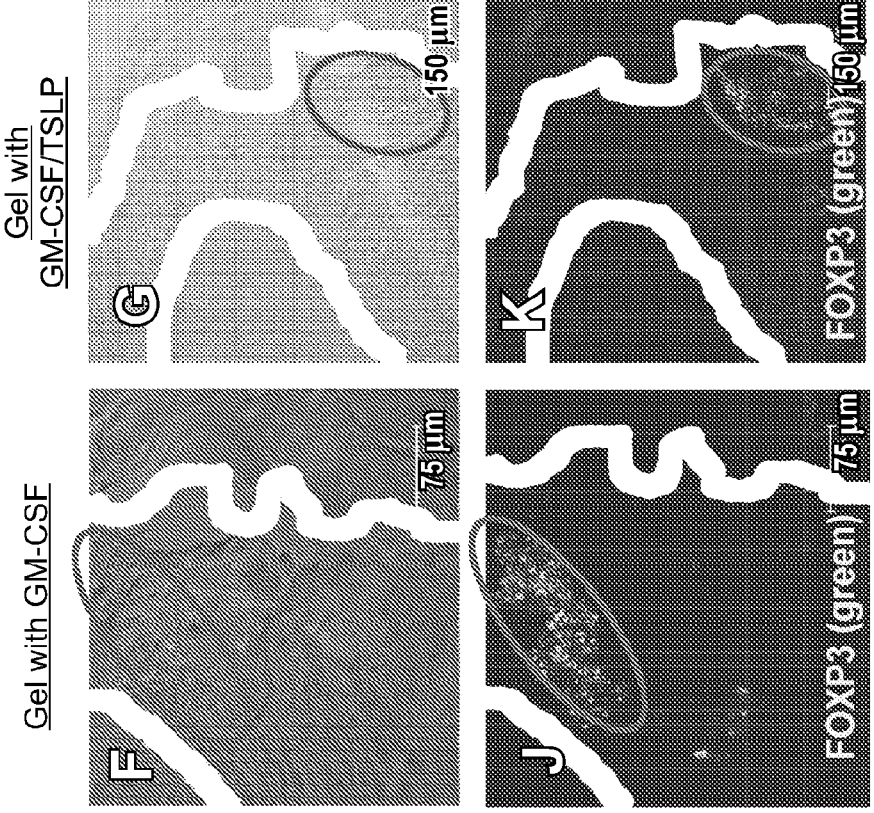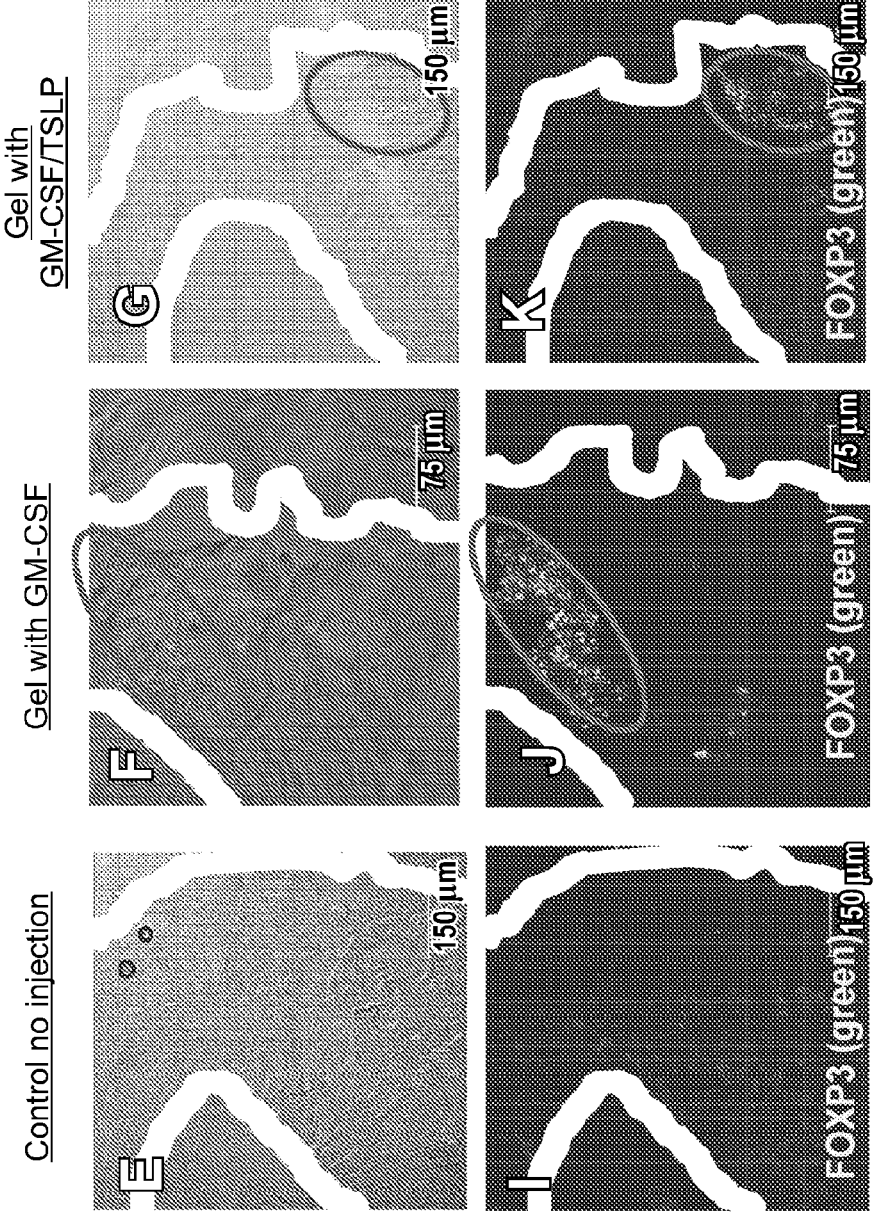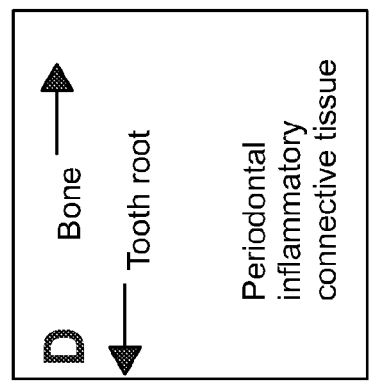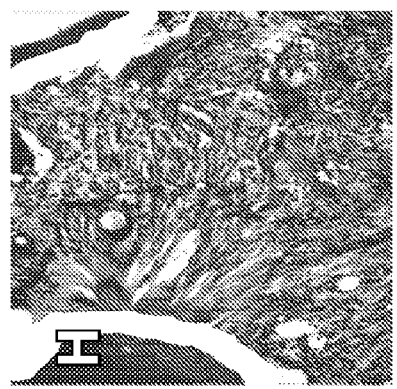

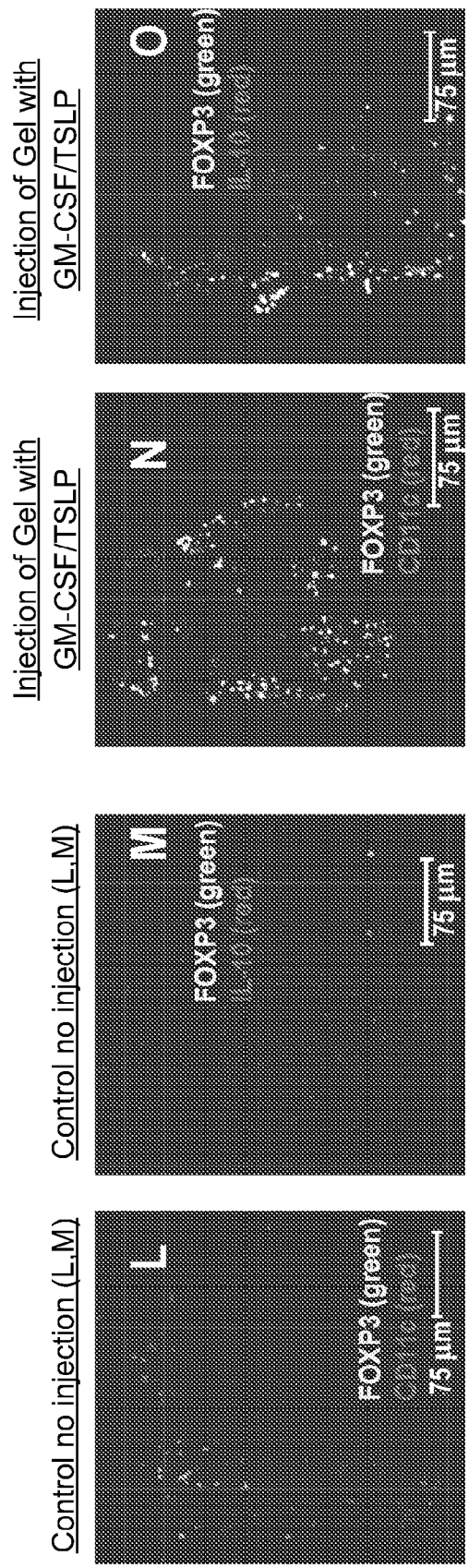

FIG. 10A
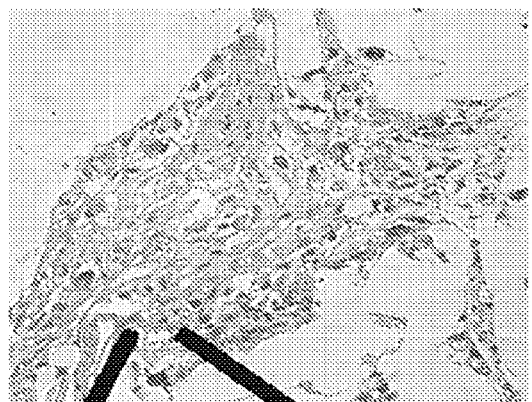
FIG. 10B
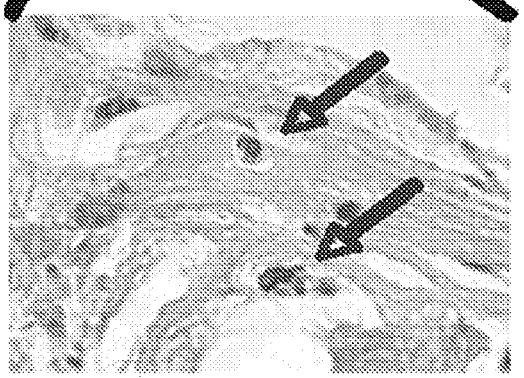
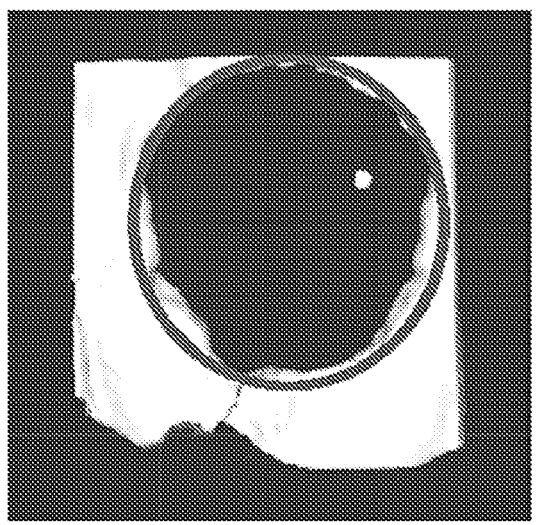
Blank Scaffold
FIG. 10C
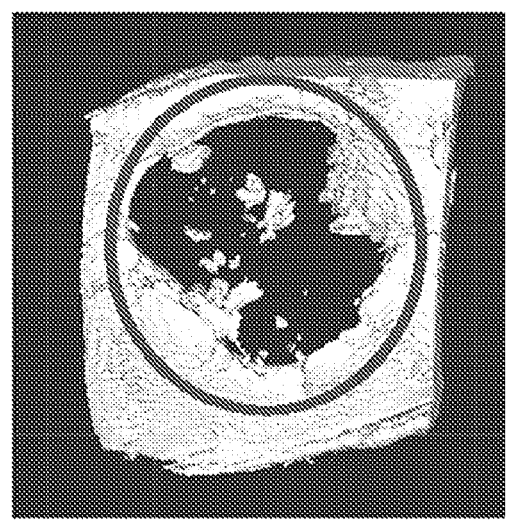
Condensed DNA
FIG. 10D

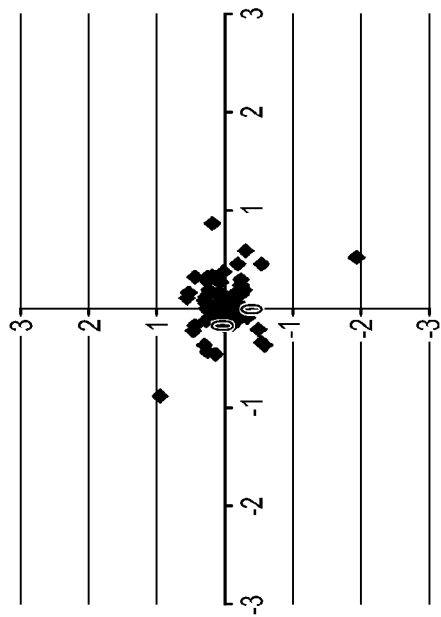
FIG. 14B
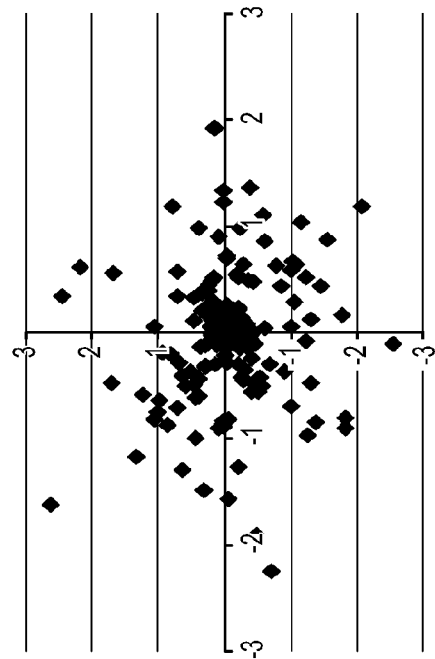
FIG. 14D
Speed:
Control: 1.1 um/min
GM-CSF: 2.1 um/min
p < 0.01
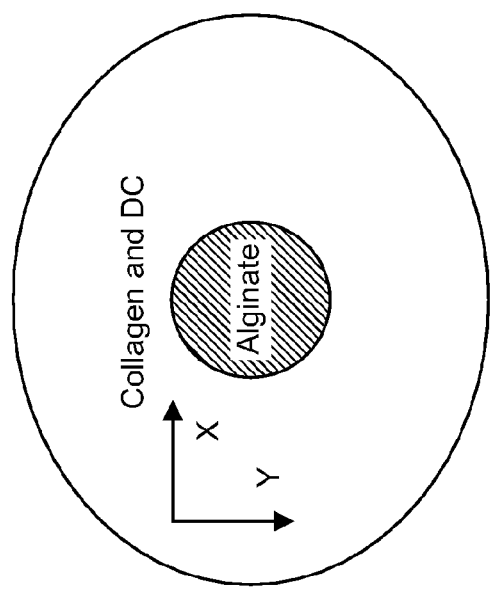
FIG. 14A
FIG. 14C

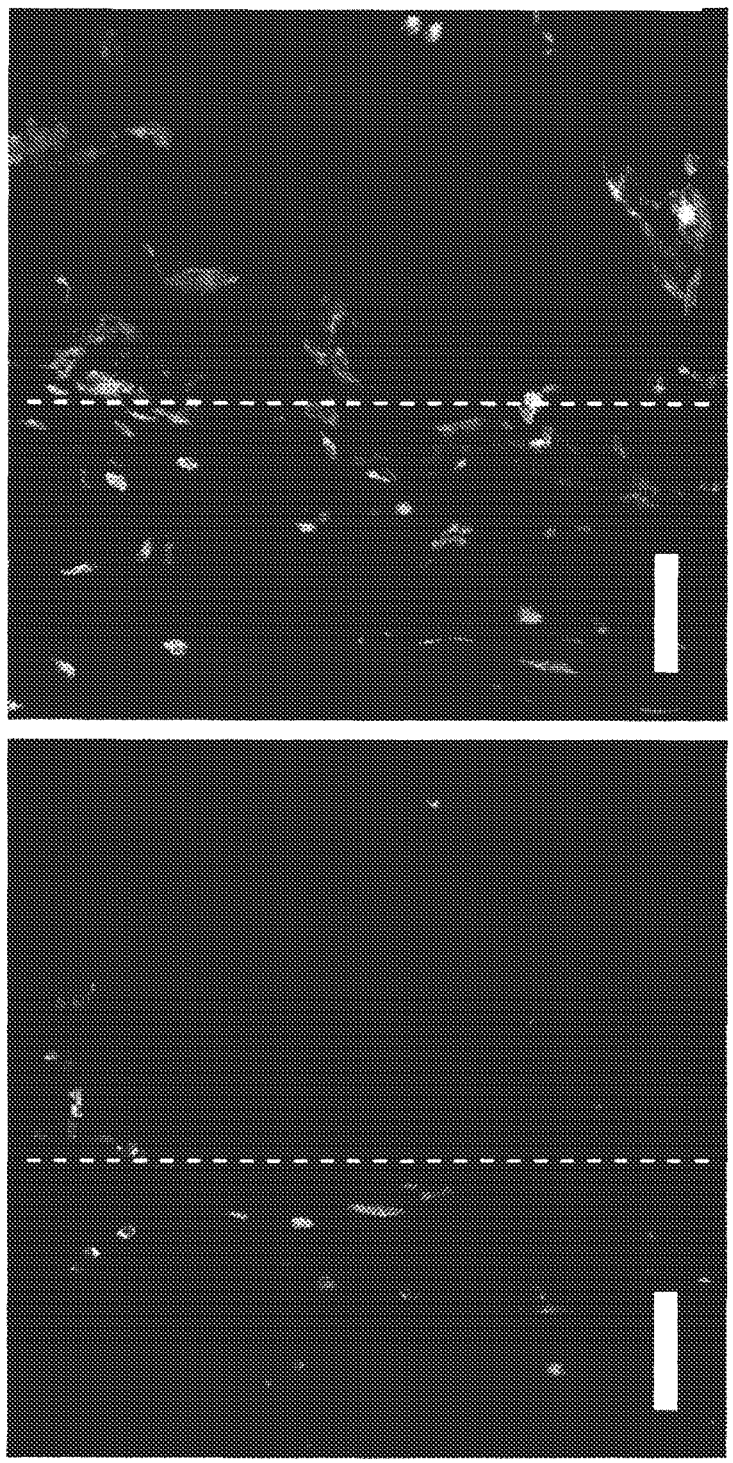

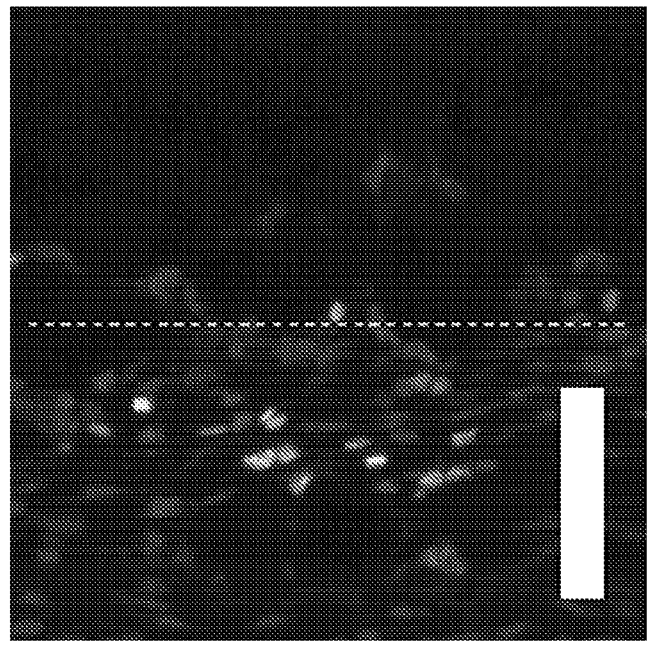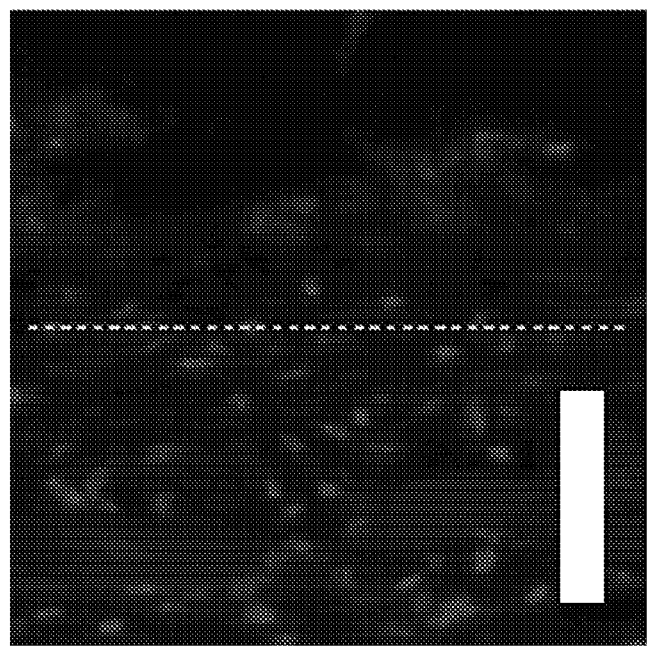
FIG. 17

PROGRAMMING OF CELLS FOR TOLEROGENIC THERAPIES

RELATED APPLICATIONS

This application is a national stage application, filed under 35 U.S.C. §371, of International Application No. PCT/US2010/044117 filed Aug. 2, 2010, which claims priority to U.S. Ser. No. 61/230,169 filed Jul. 31, 2009, the contents of which are hereby incorporated by reference in their entirety.

STATEMENT AS TO FEDERALLY SPONSORED RESEARCH

This invention was funded in part by the U.S. Government under grant number 5R01DE019917-02 awarded by the National Institutes of Health. The Government has certain rights in the invention.

FIELD OF THE INVENTION

The present invention relates to immune tolerance.

BACKGROUND

Aberrant or misregulated immune responses are underlying mechanisms of numerous pathological conditions. Such conditions include autoimmune disorders and conditions characterized by chronic inflammation.

Autoimmunity is a condition where the immune system mistakenly recognizes host tissue or cells as foreign. Autoimmune diseases affect millions of individuals worldwide. Common autoimmune disorders include type 1 diabetes mellitus, Crohn's disease, rheumatoid arthritis, and multiple sclerosis.

Chronic inflammation has been implicated in cancer, diabetes, depression, heart disease, stroke, Alzheimer's Disease, periodontitis, and many other pathologies. Aberrant or misregulated immune responses are also implicated in asthma and allergy, e.g., asthma is a prevalent disease with many allergen triggers.

SUMMARY

The invention provides a solution to the long standing clinical problems of autoimmunity, allergy/asthma, and chronic or inappropriate inflammation in the body, e.g, inflammation that leads to tissue/organ damage and destruction. The compositions and methods direct the immune response of an individual away from a pathological or life-threatening response and toward a productive or non-damaging response. Dendritic cells (DCs) play a major role in protecting against autoimmune disease. Regulatory T cells (Treg) also play an important part in inhibiting harmful immunopathological responses directed against self or foreign antigens. These cell types represent targets to manipulate for the purpose of redirecting the immune response to provide a non-inflammatory and non-destructive state.

Accordingly, the invention features a scaffold composition comprising an antigen, a recruitment composition, and a tolerogen. This scaffold composition is useful for reduction of autoimmunity. The antigen is a purified composition (e.g., protein) or is a prepared cell lysate from cells to which an undesired immune response is directed. Exemplary recruitment compositions include granulocyte-macrophage colony stimulating factor (GM-CSF; AAA52578), FMS-like tyrosine kinase 3 ligand (AAA17999.1), N-formyl peptides, fractalkine (P78423), or monocyte chemotactic protein-1 (P13500.1). Exemplary tolerogens (i.e., agents that induce immune tolerance or a reduction in an immune response) include thymic stromal lymphopoietin (TSLP; Q969D9.1)), dexamethasone, vitamin D, retinoic acid, rapamycin, aspirin, transforming growth factor beta (P01137), interleukin-10 (P01137), vasoactive intestinal peptide (CAI21764), or vascular endothelial growth factor (AAL27435). The scaffold optionally further comprises a Th1 promoting agent such as a toll-like receptor (TLR) agonist, e.g., a polynucleotide such as CpG. Th1 promoting agents are often characterized by pathogen-associated molecular patterns (PAMPs) or microbe-associated molecular patterns (MAMPs) or alarmins PAMPs or MAMPs are molecules associated with groups of pathogens, that are recognized by cells of the innate immune system via TLRs. For example, bacterial Lipopolysaccharide (LPS), an endotoxin found on the gram negative bacterial cell membrane of a bacterium, is recognized by TLR 4. Other PAMPs include bacterial flagellin, lipoteichoic acid from Gram positive bacteria, peptidoglycan, and nucleic acid variants normally associated with viruses, such as double-stranded RNA (dsRNA) or unmethylated CpG motifs. Thus, additional exemplary Th1 promoting agents comprise a TLR 3, 4, or 7 agonist such as poly (I:C), LPS/MPLA (monophosphate lipid A), or imiquimod, respectively. Exemplary TLR ligands include the following compounds: TLR7Ligands (human & mouse TLR7)—CL264 (Adenine analog), Gardiquimod™ (imidazoquinoline compound), Imiquimod (imidazoquinoline compound), and Loxoribine (guanosine analogue); TLR8Ligands (human TLR8 & mouse TLR7)—Single-stranded RNAs; E. coli RNA; TLR7/8 Ligands—(human, mouse TLR7 & human TLR8)—CL075 (thiazoloquinoline compound), CL097 (water-soluble R848), imidazoquinoline compound, Poly(dT) (thymidine homopolymer phosphorothioate oligonucleotide (ODN)), and R848 (Imidazoquinoline compound).

The scaffolds mediate sustained release of the factors loaded therein in a controlled spatio-temporal manner. For example, the factors are released over a period of days (e.g., 1, 2, 3, 4, 5, 7, 10, 12, 14 days or more) compared to bolus delivery of factors or antigens. Bolus delivery often leads to little or no effect due to short-term presentation in the body, adverse effects, or an undesirable immune response if very high doses are provided, whereas scaffold delivery avoids such events. Preferably, the scaffold is made from a non-inflammatory polymeric composition such as alginate, poly (ethylene glycol), hyaluronic acid, collagen, gelatin, poly (vinyl alcohol), fibrin, poly (glutamic acid), peptide amphiphiles, silk, fibronectin, chitin, poly(methyl methacrylate), poly(ethylene terephthalate), poly(dimethylsiloxane), poly(tetrafluoroethylene), polyethylene, polyurethane, poly (glycolic acid), poly(lactic acid), poly(caprolactone), poly (lactide-co-glycolide), polydioxanone, polyglyconate, BAK; poly(ortho ester I), poly(ortho ester) II, poly(ortho ester) III, poly(ortho ester) IV, polypropylene fumarate, poly[(carboxy phenoxy)propane-sebacic acid], poly[pyromellitylimidoalanine-co-1,6-bis(p-carboxy phenoxy)hexane], polyphosphazene, starch, cellulose, albumin, polyhydroxyalkanoates, or others known in the art (Polymers as Biomaterials for Tissue Engineering and Controlled Drug Delivery. Lakshmi S, Nair & Cato T. Laurencin, Adv Biochem Engin/Biotechnol (2006) 102: 47-90 DOI 10.1007/b137240). Alternatively, a polymeric composition that provides a low level of inflammation may also be useful, as it may aid in recruitment and/or activation of dendritic cells, particularly biasing the cells towards a Th1 response. Poly(lactide), poly(glycolide), their copolymers, and various other medical polymers may also be useful in this regard. Ceramic or metallic materials may also be utilized to present these factors in a controllable manner. For example, calcium phosphate materials are useful. In the context of bone, silica or other ceramics are also be useful.

In some examples, composite materials may be utilized. For example, immune activating factors (e.g., antigen, tolerogen, or Th1 promoting agent) are encapsulated in microspheres such as poly (lactide-co-glycolide) (PLG) microspheres, which are then dispersed in a hydrogel such as an alginate gel. Cells, e.g., DCs and/or Tregs, are recruited to or near the surface, or into the scaffold, where they may reside for some period of time as they, are exposed to antigens and other factors described above, and then migrate away to bodily tissues such as lymph nodes, where they function to induce immune tolerance. Alternatively, the scaffold with cells may create a mimic of a secondary lymphoid organ. Following contact with the loaded scaffolds, such cells become activated to redirect the immune response from a Th1/Th2/Th17 response (autoimmunity and chronic inflammation) to a Treg response or from a pathogenic Th2 state toward a Th1 state (in the case of allergy/asthma). Directing the immune response away from a Th2 response and toward a Treg response leads to a clinical benefit in allergy, asthma. For autoimmunity, the therapeutic method is carried out by identifying a subject suffering from or at risk of developing an autoimmune disease and administering to the subject the loaded scaffolds (antigen (autoantigen)+recruitment composition+tolerogen), leading to an alteration in the immune response from a Th1/Th17 to T regulatory biased immune response. For allergy/asthma, the therapeutic method is carried out by identifying a subject suffering from or at risk of developing an allergic response or asthma and administering to the subject the loaded scaffolds (antigen (allergen)+recruitment composition+adjuvant (Th1-promoting adjuvant)), thereby leading to an alteration in the immune response from a Th2 response to a Th1 biased immune response (allergy/asthma).

A method of preferentially directing a Th1-mediated antigen-specific immune response is therefore carried out by administering to a subject a scaffold comprising an antigen, a recruitment composition and an adjuvant. A dendritic cell is recruited to the scaffold, exposed to antigen, and then migrates away from the scaffold into a tissue of the subject, having been educated/activated to preferentially generate a Th1 immune response compared to a pathogenic Th2 immune response based on the exposure. As a result, the immune response is effectively skewed or biased toward the Th1 pathway versus the Th2 pathway. Such a bias is detected by measuring the amount and level of cytokines locally or in a bodily fluid such as blood or serum from the subject. For example, a Th1 response is characterized by an increase in interferon-γ (IFN-gamma). As discussed above, the scaffold optionally also comprises a Th1 promoting agent.

The compositions and methods are suitable for treatment of human subjects; however, the compositions and methods are also applicable to companion animals such as dogs and cats as well as livestock such as cows, horses, sheep, goats, pigs.

The scaffolds are useful to manipulate the immune system of an individual to treat a number of pathological conditions that are characterized by an aberrant, misdirected, or otherwise inappropriate immune response, e.g., one that causes tissue damage or destruction. Such conditions include autoimmune diseases. For example, a method of reducing the severity of an autoimmune disorder is carried out by identifying a subject suffering from an autoimmune disorder and administering to the subject a scaffold composition comprising an antigen (e.g., a purified antigen or a processed cell lysate), a recruitment composition, and a tolerogen. Preferably, the antigen is derived from or associated with a cell to which a pathologic autoimmune response is directed. In one example, the autoimmune disorder is type 1 diabetes and the antigen comprises a pancreatic cell-associated peptide or protein antigen, e.g., insulin, proinsulin, glutamic acid decarboxylase-65 (GAD65), insulinoma-associated protein 2, heat shock protein 60, ZnT8, and islet-specific glucose-6-phosphatase catalytic subunit related protein or others as described in Anderson et al., Annual Review of Immunology, 2005. 23: p. 447-485; or Waldron-Lynch et al., Endocrinology and Metabolism Clinics of North America, 2009. 38(2): p. 303).

In another example, the autoimmune disorder is multiple sclerosis and the peptide or protein antigen comprises myelin basic protein, myelin proteolipid protein, myelin-associated oligodendrocyte basic protein, and/or myelin oligodendrocyte glycoprotein. Additional examples of autoimmune diseases/conditions include Crohn's disease, rheumatoid arthritis, Systemic lupus erythematosus, Scleroderma, Alopecia greata, Antiphospholipid antibody syndrome, Autoimmune hepatitis, Celiac disease, Graves' disease, Guillain-Barre syndrome, Hashimoto's disease, Hemolytic anemia, Idiopathic thrombocytopenic purpura, inflammatory bowel disease, ulcerative colitis, inflammatory myopathies, Polymyositis, Myasthenia gravis, Primary biliary cirrhosis, Psoriasis, Sjögren's syndrome, Vitiligo, gout, celiac disease, atopic dermatitis, acne vulgaris, autoimmune hepatitis, and autoimmune pancreatitis.

The scaffolds are also useful to treat or reduce the severity of other immune disorders such as a chronic inflammatory disorder or allergy/asthma. In this context, the method includes the steps of identifying a subject suffering from chronic inflammation or allergy/asthma and administering to the subject a scaffold composition comprising an antigen associated with that disorder, a recruitment composition, and an adjuvant. The vaccine is useful to reduce acute asthmic exacerbations or attacks by reducing/eliminating the pathogenic response to the allergies. In the case of allergy and asthma, the antigen comprises an allergen that provokes allergic symptoms, e.g., histamine release or anaphylaxis, in the subject or triggers an acute asthmatic attack. For example, the allergen comprises (Amb a 1 (ragweed allergen), Der p2 (Dermatophagoides pteronyssinus allergen, the main species of house dust mite and a major inducer of asthma), Betv 1 (major White Birch (*Betula verrucosa*) pollen antigen), Aln g I from *Alnus glutinosa* (alder), Api G I from *Apium graveolens* (celery), Car b I from *Carpinus betulus* (European hornbeam), Cor a I from *Corylus avellana* (European hazel), Mal d I from *Malus domestica* (apple), phospholipase A2 (bee venom), hyaluronidase (bee venom), allergen C (bee venom), Api m 6 (bee venom), Fel d 1 (cat), Fel d 4 (cat), Gal d 1 (egg), ovotransferrin (egg), lysozyme (egg), ovalbumin (egg), casein (milk) and whey proteins (alpha-lactalbumin and beta-lactaglobulin, milk), and Ara h 1 through Ara h 8 (peanut). The compositions and methods are useful to reduce the severity of and treat numerous allergic conditions, e.g., latex allergy; allergy to ragweed, grass, tree pollen, and house dust mite; food allergy such as allergies to milk, eggs, peanuts, tree nuts (e.g., walnuts, almonds, cashews, pistachios, pecans), wheat, soy, fish, and shellfish; hay fever; as well as allergies to companion animals, insects, e.g., bee venom/bee sting or mosquito sting. Preferably, the antigen is not a tumor antigen or tumor lysate.

Also within the invention are vaccines comprising the loaded scaffold(s) described above and a pharmaceutically-acceptable excipient for injection or implantation into a subject for the to elicit antigen specific immune tolerance to reduce the severity of disease. Other routes of administration include topically affixing a skin patch comprising the scaffold or delivering scaffold compositions by aerosol into the lungs or nasal passages of an individual.

In addition to the conditions described above, the scaffolds and systems are useful for treatment of periodontitis. One example of a biomaterial system for use in vivo that recruits dendritic cells and promotes their activation towards a non-inflammatory phenotype comprises a biomaterial matrix or scaffold, e.g., a hydrogel such as alginate, and a bioactive factor such as GM-CSF or thymic stromal lymphopoietin (TSLP) for use in dental or periodontal conditions such as periodontitis. Periodontitis is a destructive disease that affects the supporting structures of the teeth including the periodontal ligament, cementum, and alveolar bone. Periodontitis represents a chronic, mixed infection by gram-negative bacteria, such as *Porphyromonas gingivalis, Prevotella intermedia, Bacteroides forsythus, Actinobacillus actinomycetemcomitans*, and gram positive organisms, such as *Peptostreptococcus micros* and *Streptococcus* intermedius.

The methods address regulatory T-cell modulation of inflammation in periodontal disease. DCs can elicit anergy and apoptosis in effector cells in addition to inducing regulatory T cells. Other mechanisms include altering the balance between Th1, Th2, Th17 and T regs. For example, TSLP is known to enhance Th2 immunity and in addition to increasing T reg numbers could increase the Th2 response. The materials recruit and program large numbers of tolerogenic DCs to promote regulatory T-cell differentiation and mediate inflammation in rodent models of periodontitis. More specifically, the recruitment, appropriate activation, and migration to the lymph nodes of appropriately activated DCs leads to the formation of high numbers of regulatory T-cells, and decreased effector T-cells, reducing periodontal inflammation.

Another aspect of the present invention addresses the mediation of inflammation in concert with promotion of regeneration. In particular, plasmid DNA (pDNA) encoding BMP-2, delivered from the material system that suppresses inflammation, reduces inflammation via DC targeting and enhances the effectiveness of inductive approaches to regenerate alveolar bone in rodent models of periodontitis. For example, significant alveolar bone regeneration results from a material that first reduces inflammation, and then actively directs bone regeneration via induction of local BMP-2 expression.

The invention provides materials that function to modulate the inflammation-driven progression of periodontal disease, and then actively promote regeneration after successful suppression of inflammation. Moreover, the compositions and methods described herein can be translated readily into new materials for guided tissue regeneration (GTR). Unlike current GTR membranes that simply provide a physical barrier to cell movement, the new materials actively regulates local immune and tissue rebuilding cell populations in situ. More broadly, inflammation is a component of many other clinical challenges in dentistry and medicine, including Sjogren's and other autoimmune diseases, and some forms of temporomandibular joint disorders. The present invention has wide utility in treating many of these diseases characterized by inflammation-mediated tissue destruction. Further, the material systems also provide novel and useful tools for basic studies probing DC trafficking, activation, T-cell differentiation, and the relation between the immune system and inflammation. In addition to the conditions and diseases described above, the compositions and methods are also useful in wound healing, e.g., to treat smoldering wounds, thereby altering the immune system toward healing and resolution of the wound.

Polypeptides and other compositions used to load the scaffolds are purified or otherwise processed/altered from the state in which they naturally occur. For example, a substantially pure polypeptide, factor, or variant thereof is preferably obtained by expression of a recombinant nucleic acid encoding the polypeptide or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight. Purity is measured by any appropriate method, e.g., column chromatography, polyacrylamide gel electrophoresis, or HPLC analysis. Accordingly, substantially pure polypeptides include recombinant polypeptides derived from a eucaryote but produced in *E. coli* or another procaryote, or in a eucaryote other than that from which the polypeptide was originally derived.

In some situations, dendritic cells or other cells, e.g., immune cells such as macrophages, B cells, T cells, used in the methods are purified or isolated. With regard to cells, the term "isolated" means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS). In other situations, cells are processed, e.g., disrupted/lysed and the lysate fractionated for use as an antigen in the scaffold.

These and other capabilities of the invention, along with the invention itself, will be more fully understood after a review of the following figures, detailed description, and claims. All references cited herein are hereby incorporated by reference. Sequences are publically available online using Entrez protein data base at www.ncbi.nlm.nih.gov/genbank/ using the sequence identifiers provided herein.

DESCRIPTION OF THE DRAWINGS

FIG. 7 shows vertical bone loss induced in a mouse model of PD. 7A is an image of a human clinical case of vertical periodontal bone loss (picture taken at the flap operation). 7B shows GTR-membrane applied onto the vertical bone loss. 7a-7f are anatomical demonstration of vertical bone loss induced in the mouse model of periodontitis. Thirty days following PPAIR-induction in the mice harboring oral Pp by systemic immunization (s.c.) with fixed Aa, animals were sacrificed and defleshed. 7a and 7b: control mice which did not receive immunization with fixed Aa; 7c-7e: mice developed vertical periodontal bone loss around the maxillary molars by systemic immunization with fixed Aa; 7g: histochemical (HE-staining) image of decalcified tissue section of control periodontally healthy mouse; 7h: histochemical (HE-staining) image of mouse which developed PD accompanied by vertical periodontal bone loss (higher magnification image clearly demonstrates extensive neutrophil infiltration).

FIG. 9 shows expansion of FOXP3+ T cells in mouse gingival tissue and local lymph nodes (LN) by GM-CSF/TSLP delivery polymer. FOXP3-EGFP-KI mice which previously developed periodontal bone-resorption-socket (maxillary molars) by PPAIR-mediated PD induction received a gingival injection of a total 1.5 µl of (1) control empty polymer, (2) polymer with GM-CSF (1 µg), and (3) polymer with GM-CSF (1 µg)+TSLP (1 µg). The local cervical lymph nodes (CLN) and maxillary jaws were removed from the sacrificed animals at Day-7 after the injection of polymer. EGFP+ cells (=FOXP3+ Treg cells) in the CLN were monitored by flow cytometry (9A, 9B and 9C). The presence of FOXP3+ Treg cells in the mouse periodontal bone loss lesion was evaluated using a fluorescent confocal microscope (9D-9K). (9D): illustration indicating the anatomical objects (tooth root, alveolar bone and inflammatory connective tissue), (9H): histochemical image (HE-staining) of periodontal bone loss lesion, (9E-9G): bright field images, (9I-9K): fluorescent images. (9E, 9H and 9I): adjacent section of a mouse which did not receive polymer injection, (9F, 9J): a mouse receiving polymer injection with GM-CSF, (9G, 9K): a mouse receiving polymer injection with GM-CSF+TSLP. Mouse gingival tissue in the bone loss lesion that received GM-CSF/TSLP delivery polymer showed CD11c+ cells and IL-10 around the FOXP3+ T cells infiltrating in the foci (9N, 9O), whereas the control bone loss lesion did not receive polymer injection showed little or no CD11C+ cells or IL-10 in the tissue where the infiltrate of FOXP3 cells was also low (9L, 9M).

FIG. 10 demonstrates that polymeric delivery of PEI-condensed pDNA encoding BMP leads to bone regeneration. Implantation of scaffolds led to (10A) long-term (15 week) expression of human BMP-4 in mice (immunohistochemistry; arrows indicate positive cells), and (10B) significant regeneration of bone in critical size cranial defects, as compared to blank polymers. Circles denote original area of bone defect, bone within the circle represents newly regenerated bone tissue. Statistically significant increases in the defect area filled with osteoid (10C) and mineralized tissue (10D), were found with condensed pDNA delivery, as compared to blank polymers, or polymers loaded with an equivalent quantity of non-condensed pDNA. All data at 15 weeks, and values represent mean and standard deviation. The data demonstrate control over the timing of pDNA release from alginate gels via control over gel degradation rate.

FIG. 14A is a diagram showing an overhead view of a petri dish, light shading represents the collagen and DCs while the darker shading (inner circle) represents the alginate gel).

FIGS. 14B-C are dot plots showing bone marrow-derived dendritic cell chemokinesis in vitro to alginate containing hydrogels with or without GM-CSF. FIG. 14B (no GM-CSF); FIG. 14C (GM-CSF mixed in with alginate).

FIG. 14D is a list of average migration speed of dendritic cells in the presence of GM-CSF and in the absence of GM-CSF (control).

FIGS. 16A-B are a series of photomicrographs showing recruitment of DCs to GM-CSF loaded alginate gels in vivo. FIG. 16A shows alginate gels without GM-CSF, and FIG. 16B shows alginate gels containing GM-CSF.

FIG. 17 is a series of photomicrographs showing expression of Forkhead box P3 (FoxP3) in cells adjacent to alginate gels releasing GM-CSF and Thymic stromal lymphopoietin (TSLP) in vivo. Gels containing 3 µg of GM-CSF and 0 µg (A, left panel) or 1 µg (B, right panel) of TSLP were explanted 7 days after injection. White dotted lines indicate the border between the dermal tissue (left) and the alginate gels (right). Scale bars are 50 µm.

DETAILED DESCRIPTION

Figure 1:
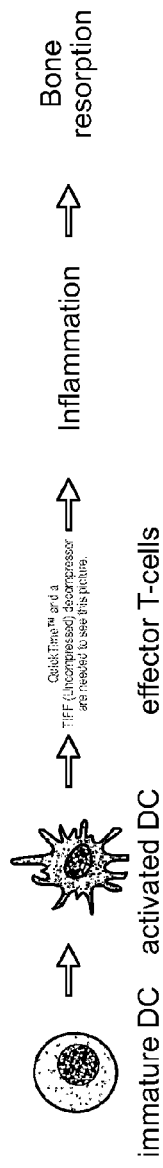
FIG. 1 is a schematic of the immune response role in periodontal disease (PD). The infection of PD typically leads to the formation of activated dendritic cells, which lead to generation of effector T-cells, and chronic inflammation in the tissue that over time results in bone resorption.

The scaffolds and systems described herein mediate spatiotemporal presentation of cues that locally control DC activation and bias the immune response towards a non-pathogenic state. The scaffolds and methods are used to treat subjects that have been identified as suffering from or at risk of developing diseases or disorders characterized by inappropriate immune activation. The biomaterial systems (loaded scaffolds) recruit DCs and promote their activation towards a tolerogenic or non-inflammatory phenotype (autoimmunity/inflammation) or an activated state (allergy/asthma) that corrects an aberrant or misregulated immune response that occurs in a pathologic condition.

For autoimmune disease, the scaffolds comprise an antigen (autoantigen), a recruitment composition, and a tolerogen. For allergy or asthma, the scaffolds comprise and antigen (allergen), a recruitment composition, and an adjuvant (e.g, a Th1 promoting adjuvant such as CpG). Generation of Treg cells leads to clinical benefit by directing the immune response away from pathogenic T effectors and toward other immune effectors such as Treg, Th1, Th17 arms of the immune system.

The vaccines attenuate diseases of pathogenic immunity by re-directing the immune system from a Th1/Th17 to T regulatory biased immune response (autoimmunity) and a Th2 response to a Th1 biased immune response (allergy/asthma).

Scaffolds

Exemplary scaffolds were produced using PLG (for allergy or asthma) or alginate (for autoimmune diseases such as diabetes of for periodontitis). PLG was compressed, gas foamed, and leached (porogens (that were later leached) 250 µm to 400 µm made up 90% of the compressed powder) to create a porous material. Gels are typically 1-20% polymer, e.g., 1-5% or 1-2% alginate. Methods of making scaffolds are known in the art, e.g., U.S. Ser. No. 11/638,796 or PCT/US2009/000914. The polymers are preferably crosslinked. For example, 1-2% alginate was crosslinked ionically in the presence of a divalent cation (e.g., calcium). Alternatively, to modify the spatiotemporal presentation of molecules and control degradation, the alginate is crosslinked covalently by derivatizing the alginate chains with molecules by oxidation with sodium periodate and crosslinking with adipic dihydrazide.

Vaccines that Attenuate Diseases of Pathogenic Immunity by Re-Directing the Immune System from a Th1/Th17 to T Regulatory Biased Immune Response GM-CSF enhanced chemokinesis of bone marrow dendritic cells in vitro. Alginate gels with or without GM-CSF (~1 µg/gel) were placed in a petri dish and surrounded with collagen containing bone marrow derived murine dendritic cells (FIG. 14A). The cells were followed for 8 hours using time-lapse imaging. The velocity of the cells was calculated from initial and final position values and is plotted in FIGS. 14B and C in µm/min Chemotaxis toward the alginate is given as the positive x coordinate (positive x is directed radially inward). Each dot reflects the velocity of 1 cell, and each plot is representative of three experiments. The average migration speed of cells in the presence of GM-CSF was 3.1 µm/min compared to 1.1 µm/min in the absence of GM-CSF. The speed of control and alginate gels is shown in FIG. 14D and was found to be significantly different at p<0.01. These data indicate that GM-CSF increases the speed of movement of dendritic cells and thus promotes dendritic cell migration.

Figure 15:
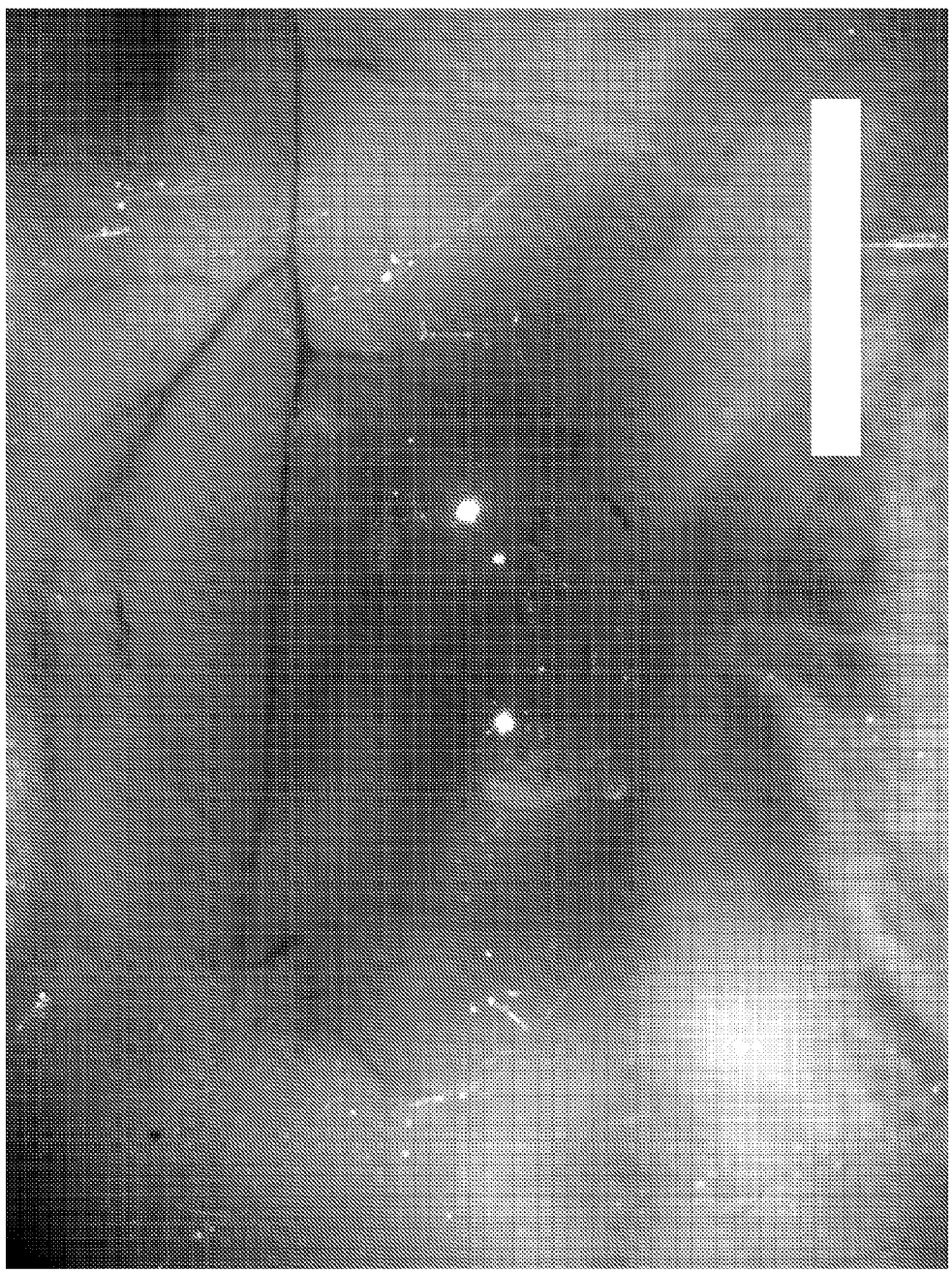
FIG. 15 is a photograph of alginate gel scaffold material under the skin of a mouse. Scale bar is 5 mm.

To observe the biomaterial scaffold in vivo, alginate gels were injected intradermally (FIG. 15). A 60 µL alginate gel was injected intradermally into the skin of a mouse. A photographic image was taken from the dermal side of the skin after euthanasia of the animal. Blue dye was incorporated into alginate gels before crosslinking for visualization.

Recruitment of DCs to GM-CSF Loaded Alginate Gels in Vivo

Figure 16C:
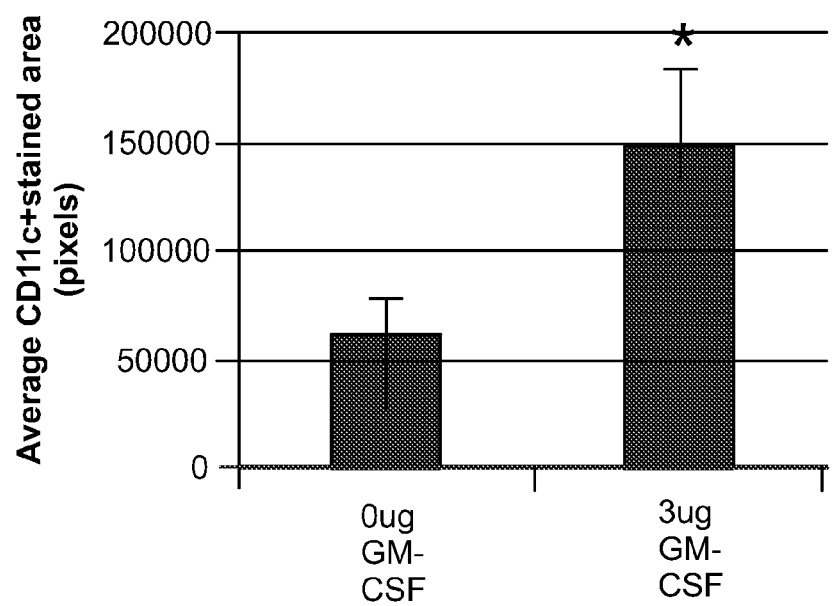
FIG. 16C is a bar graph showing a quantification of cells in blank (alginate without GM-CSF) and GM-CSF loaded alginate gels.

FIGS. 16A-B show the results of immunofluorescent staining of sectioned skin containing alginate gels, showing nuclei, MHC class II, and CD11c. Gels containing 0 µg (A) or 3 µg (B) of GM-CSF were explanted 7 days after injection. White dotted lines indicate the border between the dermal tissue (left) and the alginate gels (right). Scale bars are 50 µm. The area in tissue sections comprised of CD11c+ cells in blank gels vs. gels loaded with 3 µg of GM-CSF was quantified after 7 days. Image analysis of stained sections was done using ImageJ (n=3 animals/condition). *P<0.02. The data demonstrate that dendritic cells were recruited to GM-CSF loaded gels in vivo.

T Regulatory (Treg) Cells are Recruited to GM-CSF/TSLP Loaded Gels

Treg cells were detected adjacent to alginate gels releasing GM-CSF and TSLP in vivo. TSLP promotes immune tolerance mediated by Treg cells and plays a direct and indirect role in regulating suppressive activities of such cells. The main influence of TSLP peripherally is on the DCs; however, T cells have receptors for TSLP and are also affected. Although Tregs are instrumental as being the mode of therapeutic benefit for periodontal disease, switch to a Th2 response (Th1→Treg/Th2) is also involved. For other diseases, a predominantly Treg response is desired; in the latter case, factors such as TGF-beta and IL-10 are utilized.

Cells were identified in FIG. 7 by detecting expression of FoxP3, a transcription factor specifically expressed in CD4+ CD25+ Treg cells. Panels A and B of FIG. 17 show the results of immunofluorescent staining of sectioned skin containing alginate gels, showing nuclei (grey dots) and FoxP3 (bright dots). All gels contained 3 µg of GM-CSF. The gel in panel (A) did not contain TSLP (0 µg), whereas the gel in panel (B) contained 1 µg of TSLP. The gels were explanted 7 days after injection and analyzed. White dotted lines indicate the border between the dermal tissue (left) and the alginate gels (right). Scale bars are 50 µm. Numerous bright dots (FoxP3-positive Treg cells) were detected using gels containing both GM-CSF and TSLP. These data indicate that in increased number of Treg cells are recruited to gels containing both GM-CSF and TSLP compared to GM-CSF alone or alginate alone.

Dendritic Cell Immunotherapy for Type 1 Diabetes

The gel scaffolds described herein were evaluated in an art-recognized autoimmune model for type 1 diabetes mellitus (T1DM). The model utilizes a transgenic animal that expresses ovalbumin (OVA) under the control of the rat insulin promoter (RIP) in the pancreas (RIP-OVA model). (see, e.g., Proc Natl Acad Sci USA. 1999 Oct. 26; 96(22): 12703-12707; or Blanas et al., 1996. Science 274(5293):1707-9). OVA-specific CD8-positive (cytotoxic T) cells are adoptively transferred intravenously to induce and establish autoimmune diabetes. More specifically, the adoptively transferred T cells recognize the ovalbumin presented on the pancreatic beta cells and attack these cells resulting in dampened insulin secretion and diabetes.

Figure 18:
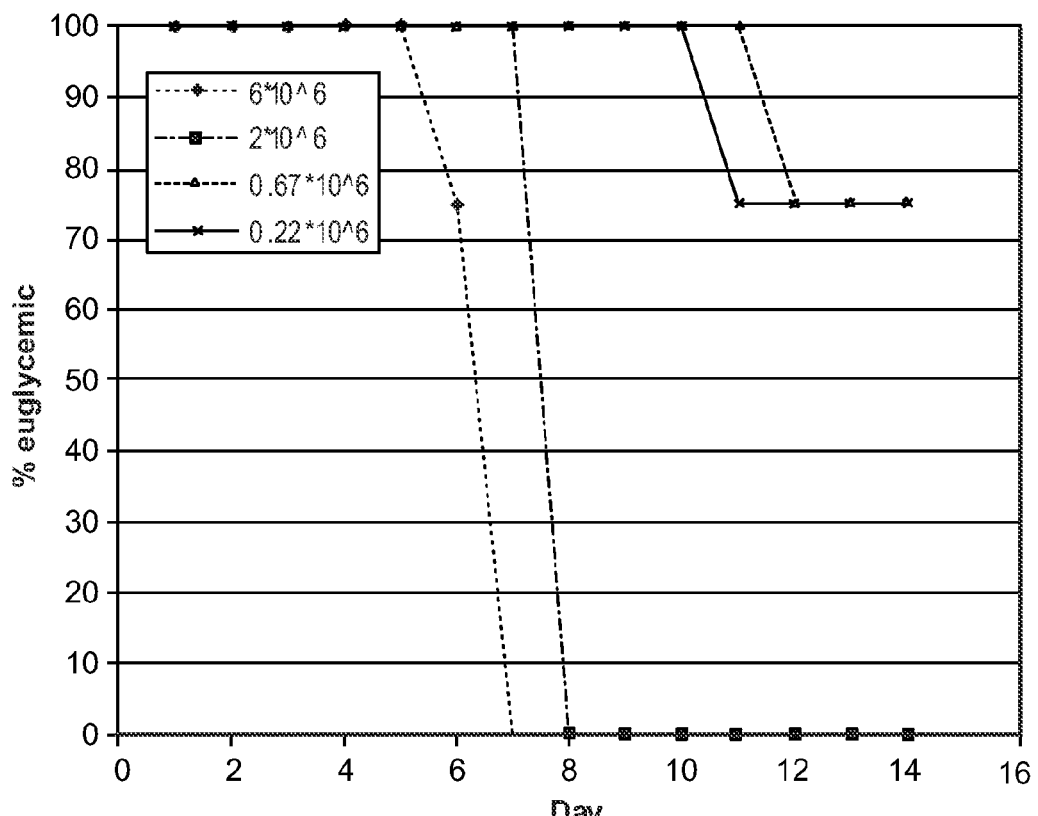
FIG. 18 is a line graph showing establishment of a murine type 1 diabetes model.

FIG. 18 shows percentages of euglycemic RIP-OVA mice over time following injection with various doses of OT-I splenocytes. 4 mice per group were injected with $6 \times 10^6$, $2 \times 10^6$, $0.67 \times 10^6$, or $0.22 \times 10^6$ activated CD8+Va2+ OT-I splenocytes administered i.v. Adoptive transfer of approximately $2 \times 10^6$ cells leads to diabetes in one week. Hyperglycemia was defined as 3 consecutive days with a blood glucose reading above 300 mg/dL. Between $0.67 \times 10^6$ and $2 \times 10^6$ T cells is a critical threshold for inducing disease. If cells are adminstered at this level concomitantly with therapies that influence T cell fate as described herein, the number the number of animals that eventually become diabetic and the speed at which they become diabetic is substantially altered in comparison to control animals with the adoptive transfer of cells alone without therapy.

Figure 19:
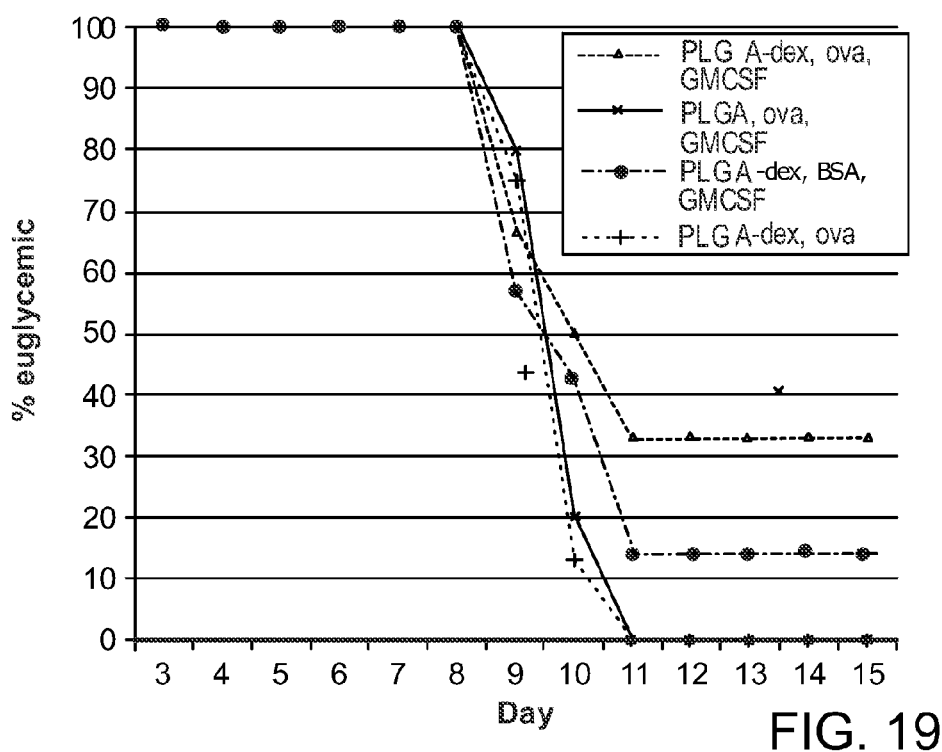
FIG. 19 is a line graph showing quantification of euglycemic cells following administration of scaffolds containing PLGA-dex, ova, and GM-CSF; PLGA, ova, and GM-CSF, PLGA-dex, BSA and GM-CSF; and PLGA-dex and ova.

Using the same model system, alginate gel scaffolds were implanted intradermally. The percentage of euglycemic mice was then determined over time following injection with $2 \times 10^6$ OT-I splenocytes 10 days after alginate intradermal implantation (FIG. 19). All animals received an injection of alginate. Like TSLP, Dexamethasone (dex) is a composition that induces immune tolerance. In this experiment, dexamethasone was encapsulated in poly (lactide-co-glycolide) (PLG) microspheres prior to loading into alginate gels to delay release of the dexamethasone. The composition of the alginate gels was as follows: PLG: blank poly (lactide-co-glycolide) microspheres, PLGA-dex: dexamethasone (100 ng) encapsulated in poly (lactide-co-glycolide) microspheres, ova: ovalbumin (25 ug), GMCSF: granulocyte macrophage colony stimulating factor (6 ug), BSA: bovine serum albumin (25 ug). Hyperglycemia was defined as 3 consecutive days with a blood glucose reading above 300 mg/dL. Six or more mice were included in each group. Although dexamethasone blocks the action of insulin, a controlled spatio-temporal presentation of antigen+tolerogen led to an improvement in diabetes (greater percentage of euglycemic and slower onset of disease) in the PLGA-dex+Ova+GM-CSF group compared to the other groups, demonstrating that the combination of tolerogen, antigen, and recruiting agent in the context of a scaffold led to a reduction in a diabetes-associated autoimmune response specifically against pancreatic cells in vivo.

Vaccines for Attenuation of Allergic Conditions

Immunoglobulin E (IgE) is a type of antibody that is normally present in small amounts in the body but plays a major role in allergic diseases. The surfaces of mast cells contain receptors for binding IgE. When IgE binds to mast cells, a cascade of allergic reaction can begin. IgE antibodies bind to allergens (antigens) and trigger degranulation and the release of substances, e.g., histamine, from mast cells leading to inflammation. Allergens induce T cells to activate B cells (Th2 response), which develop into plasma cells that produce and release more antibodies, thereby perpetuating an allergic reaction.

Scaffold-based vaccines were made to attenuate allergy, asthma, and other conditions characterized by aberrant immune activation by redirecting the immune system from a Th2 to a Th1 biased response. The scaffold-based vaccines reduced the production of IgE that leads to allergic symptoms caused by histamine (and other pro-inflammatory molecules) release due to mast cell degranulation.

Figure 20:
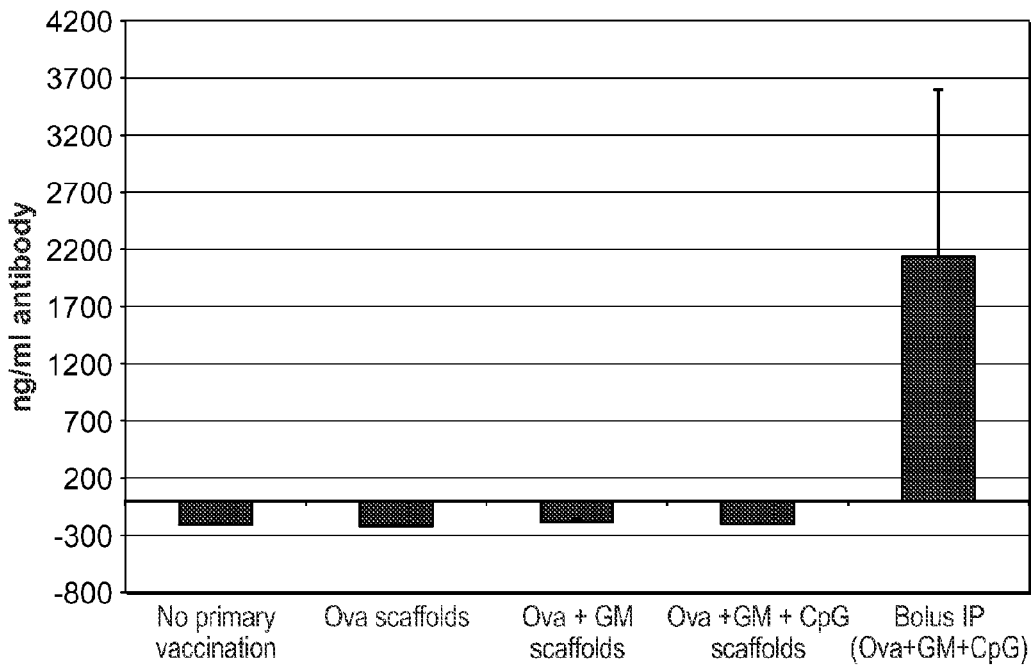
FIG. 20 is a bar graph showing ovalbumin-specific IgE in serum following vaccination. The following vaccination groups were tested: no primary vaccination; Ova scaffolds; Ova+GM-CSF scaffolds; Ova+GM-CSF+CpG scaffolds; and Bolus intraperitoneal (IP) injection of Ova+GM-CSF+CpG)/no scaffold. These data show that vaccination does not elicit pathogenic IgE antibodies.
Figure 21:
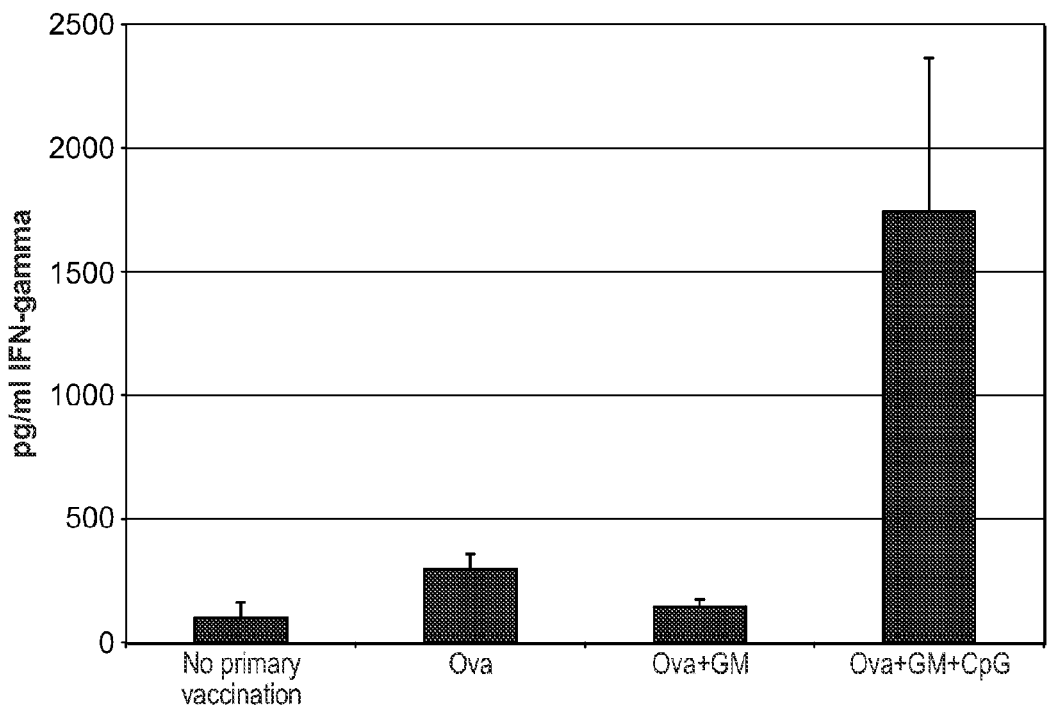
FIG. 21A is a bar graph showing splenocyte interferon-γ (IFN-gamma) elaboration following ovalbumin administration.

Antibody production in response to the vaccinations was first evaluated. Balb/c mice were left untreated (No primary vaccination control). Other mice were administered 10 μg of ovalbumin incorporated into a scaffold (Ova scaffolds), 10 μg of ovalbumin with 3 μg GM-CSF incorporated into a scaffold (Ova+GM scaffolds), 10 μg of ovalbumin with 3 μg GM-CSF and 100 μg CpG incorporated into a scaffold (Ova+GM+CpG scaffolds), or 10 μg of ovalbumin with 3 μg GM-CSF and 100 μg CpG injected intraperitoneally (Bolus IP (Ova, GM, CpG). Poly lactide-co-glycolide (PLG) scaffolds were made by a gas foaming, particle leaching technique. 13 days later, the serum was collected from the animals and assayed by ELISA for ova-specific IgE antibody titres. The scaffold vaccines were administered subcutaneously into the flank. Bolus IP injection led to an IgE antibody response. However, scaffold mediated delivery of factors using scaffolds (i.e., using controlled release in a spatio-temporal manner) did not lead to an antibody response (FIG. 20). Therefore, the scaffold delivery strategy does not promote production of an allergic response mediated by IgE/mast cell degranulation.

On day 14, all of the mice were vaccinated with ovalbumin adsorbed to alum (adjuvant). 13 days later, serum ovalbumin-specific IgE was quantitated (day 27). N=5-10 animals. The mice were given Ova antigen+alum (adjuvant) to provoke a Th2-mediated allergic response. The data indicate that vaccination with scaffolds containing antigen+recruiting agent (GM-CSF)+Th1 promoting/stimulatory factor (CpG) reduces the Th2-mediated allergic response and preferentially increases the Th1-mediated response leading to reduction in allergy mediators.

The immune response elicited by the vaccines was further characterized. Balb/c mice were left untreated (No primary vaccination). Other mice were administered 10 μg of ovalbumin incorporated into a scaffold (Ova scaffolds), 10 μg of ovalbumin with 3 μg GM-CSF incorporated into a scaffold (Ova+GM scaffolds), or 10 μg of ovalbumin with 3 μg GM-CSF and 100 μg CpG incorporated into a scaffold (Ova+GM+CpG scaffolds). 14 days later all of the mice were vaccinated with ovalbumin adsorbed to alum and 14 days later (day 28) the splenocytes from the animals were cultured with ovalbumin. Media was collected from the cell culture supernatants and IFN-gamma production or IL-4 production was assayed using an ELISA. N=5-10 animals. The results indicated that vaccination with all 3 factors in a scaffold (Ova+GM+CpG scaffolds) led to an increased level of IFN-gamma, thereby demonstrating a shift toward a Th1 immune response (and away from a Th2 allergy response).

Bolus administration of CpG has sometimes been associated with splenomegaly. Experiments were therefore carried out to evaluate spleen enlargement following vaccine administration. The results indicated that bolus administration led to splenomegaly; however, delivery of factors (e.g., antigen/recruiting agent/Th1 stimulatory agent; Ova/GM-CSF/CpG) in a scaffold did not lead to splenomegaly. Thus, an advantage of the controlled spatio-temporal release of the factors from the scaffold is avoidance of the adverse side effect of spleen enlargement. The scaffolds and methods of using them have many other advantages compared to other strategies that have been developed to take advantage of the dendritic cell's central role in the immune system including antibody targetting of DC and ex vivo DC adoptive transfers. The former technique lacks specificity and unlike the scaffold poorly controls the microenvironment where antigen is detected. Adoptive transfer is costly, ephemeral, and many of the cells die or function poorly following administration. The scaffold system described here is less costly, directs cells through the lifetime of the implant (continuous vs. batch processing), and does not require ex vivo cell processing which leads to poor cell viability and hypofunctioning.

Figure 22:
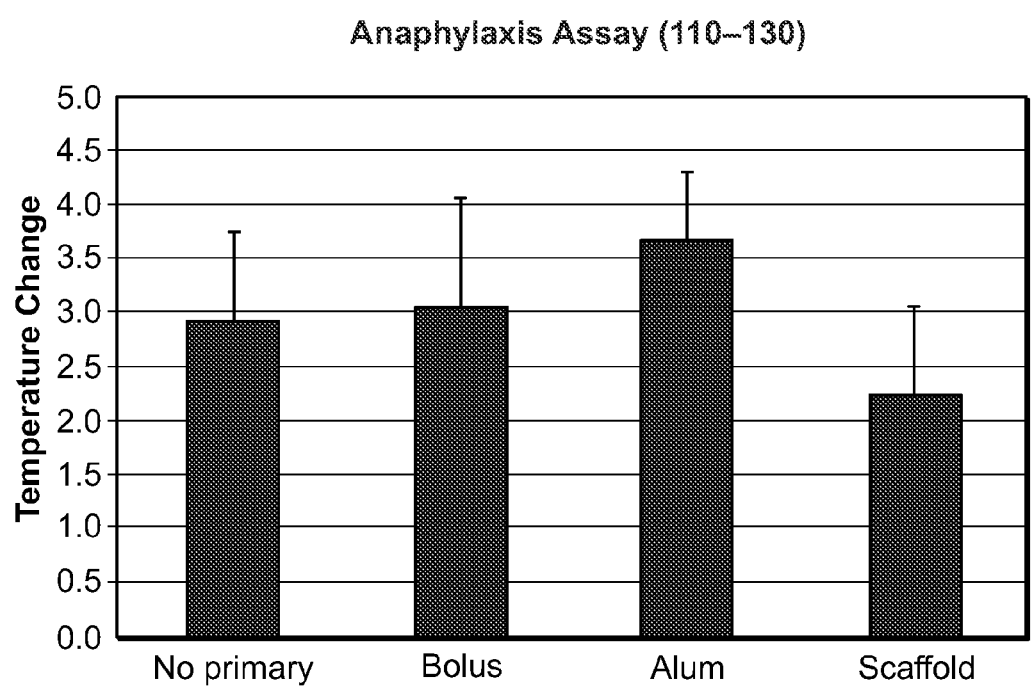
FIG. 22 is a bar graph showing attenuation of anaphylactic shock following vaccination with scaffolds containing CpG, GM-CSF, and ovalbumin. Temperature of test animals was measured following vaccination and subsequent intraperitoneal challenge with ovalbumin.

Vaccination was evaluated in an allergy animal model of anaphylactic shock caused by and antigen trigger. Histamine release leads to a change in temperature (decrease in temperature of the subject), which was used as a measure of the severity of allergic response. Balb/c mice were administered 10 μg of ovalbumin in alum (alum); 10 μg of ovalbumin with 3 μg GM-CSF, and 100 μg CpG subcutaneously (bolus); 10 g of ovalbumin with 3 μg GM-CSF, and 100 μg CpG in a scaffold subcutaneously (scaffold); or no primary treatment (no primary) on day 0. On week 2, 5, and 8 the animals were vaccinated with ovalbumin adsorbed to alum and on week 11 the animals were administered 1 mg of ovalbumin intraperitoneally. n=7 or 8, error bars SEM. The results shown in FIG. 22 indicate that vaccination using a scaffold loaded with antigen+recruitment composition+adjuvant leads to a reduction in symptoms of allergy.

Gel Scaffold Material Based Vaccines for Treatment of Periodontitis and Other Inflammatory Dental or Periodontal Conditions Chronic inflammation is a major component of many of dentistry's most pressing diseases, including periodontitis, which is characterized by chronic inflammation that can lead to progressive loss of alveolar bone and tooth loss. Several tissue engineering and regeneration strategies have been identified that may be able to reverse the destructive effects of periodontitis, including the delivery of various morphogens and cell populations, but their utility is likely compromised by the hostile microenvironment characteristic of the chronic inflammatory state. The inflammation in periodontitis relates to both the bacterial infection and to the overaggressive immune response to the microorganisms, and this has led to efforts seeking to modulate inflammation via interference with the immune response. Therefore, there is an urgent need to devise novel therapeutic approaches for periodontitis treatment.

Chronic inflammation is characterized by continuous tissue destruction, and is component of many oral and craniofacial diseases, including periodontitis, pulpitis, Sjogren's, and certain temperomandibular joint disorders. Periodontal disease (PD), in particular, is characterized by inflammation, soft tissue destruction and bone resorption around the teeth, resulting in tooth loss. About 30% of the adult U.S. population has moderate periodontitis, with 5% of the adult population experiencing severe periodontitis. Also, because PD tends to exacerbate the pathogenicity of various systemic diseases, such as cardiovascular disease and low birth weight, PD can contribute to morbidity and mortality, especially in individuals exhibiting a compromised host defense. Guided tissue regeneration (GTR) membranes are commonly used to enhance periodontal regeneration, and these membranes provide a physical barrier to prevent epithelial cells from the overlying gingiva from invading the defect site and interfering with alveolar bone regeneration and reattachment to the tooth. GTR membranes can enhance regeneration, although typically not in a highly predictable manner, likely due to their passive approach to regeneration. Therefore, there is an urgent need to devise novel therapeutic approaches for PD treatment.

One of the major complications of periodontal diseases is the irreversible bone resorption that results in the loss of affected teeth. PD is treated currently by mechanical removal of the bacteria colonizing the teeth, and/or systemic or local antibiotic treatment. Although these approaches reduce the bacterial load can, when combined with appropriate oral hygiene, retard disease progression, they do not directly address the chronic inflammation driving tissue destruction nor promote regeneration of the lost tissue structures. Pathogenic bone loss in PD is induced by lymphocytes that produce osteoclast differentiation factor RANKL. One approach to preventing the progression of PD leading to bone loss is to modulate T- and B-cell responses to the bacterial infection in periodontal tissue. Using both rat and mouse models of PD, such an approach was indeed efficient in inhibiting immune-RANKL-mediated bone resorption. The methods and compositions described herein the chronic inflammatory response must be resolved to block further tissue destruction, and regeneration of the lost tissue must be promoted actively through inclusion of appropriate biologically active agents.

The reduce periodontal inflammation and regenerate bone previously lost to PD. For example, the pathogenic process of bone resorption and inflammation elicited by lymphocytes (FIG. 1) is suppressed by FOXP3(+) T regulatory (Treg) cells via locally activated tolerogenic dendritic cells (tDCs). After the remission of inflammatory immune response by DC that promote the formation of regulatory T-cells (Tregs), the lost bone in the lesion is remodeled by localized delivery of a plasmid vector which encodes bone morphogenic protein (BMP). The material is administered using a minimally invasive delivery (i.e., gingival injection) and provides a temporally controlled release of functionally different bioactive compounds. The device promotes (a) initial DC programming to quench inflammation via recruitment and expansion of Tregs, and (b) subsequent release of a BMP-2 encoding plasmid vector to induce bone regeneration.

T-cells and B-cells play major role in bone resorption in PD in human and animal models. An active periodontal lesion is characterized by the prominent infiltration of B-cells and T cells. Specifically, plasma cells constitute 50%-60% of total cellular infiltrates, which makes PD distinct from other chronic infectious diseases. The osteoclast differentiation factor, Receptor Activator of NF-kB ligand (RANKL), is distinctively expressed by activated T-cells and B-cells in gingival tissues with PD, but not by these cells in healthy gingival tissues. The RANKL that was expressed on the T- and B-cells in patients' gingival tissues was sufficiently potent to induce in vitro osteoclastogenesis in a RANKL-dependent manner. The finding that RANKL is implicated as a trigger of osteoclast differentiation and activation in almost all inflammatory bone resorptive diseases emphasizes the importance of addressing this target.

Mouse models are recognized as the art for the study the roles of DCs and Tregs in bone regeneration processes in PD, in which inflammatory periodontal bone resorption is induced by the immune responses to live bacterial infection (FIG. 1). Adoptive transfer of antigen-specific T-cells or B-cells that express RANKL can induce bone loss in rat periodontal tissue that received local injection of the T-cell antigen *A. actinomycetemcomitans* (Aa) Omp29 or whole Aa bacteria as the B-cell antigen. The involvement of T-cells in the bone resorption processes was demonstrated by two inhibitors: (1) CTLA4-Ig (binding inhibitor for T cell CD28 binding to B7 co-stimulatory molecule expressed by APC); and (2) Kaliotoxin (blocker for T cell-specific potassium channel Kv1.3). Specifically, Kaliotoxin inhibits RANKL production by activated rat T cells. Adoptive transfer of an Au-specific human T-cell line isolated from patients with aggressive (juvenile) periodontal disease could induce significant periodontal bone loss in NOD/SCID mice that were orally inoculated with Aa every three days.

Immune responses induced to Aa-immunized mice and rats do display Periodontal Pathogenic Adaptive Immune Response (PPAIR). Previous studies of rat models replicate most of the patho-physiological conditions of localized aggressive periodontitis (LAP) patients infected with Aa as well as some features of adult periodontitis. This model, relies on artificial bacterial antigen injection into gingival tissue rather than live bacterial infection. Furthermore, the lack of a variety of gene knockout rat strains hinders elucidation of the host genetic linkage to bacterial infection-mediated PD. A mouse model of PD replicates many of the critical features of human PD, and the pathogenic outcomes of adaptive immune reaction in mice, including those associated with RANKL induction, and is useful in terms of bone resorption induced in the periodontal tissue.

Tregs suppress overreaction of adaptive T effector cells and quench inflammation. Tregs were discovered originally as a subset of T-cells that showed suppression function in several experimental autoimmune diseases in animals. Tregs produce antigen-non-specific suppressive factors, such as IL-10 and TGF-13. In addition, they constitutively express cytotoxic T-lymphocyte antigen 4 (CTLA-4), which down-regulates DC activation and is a potent negative regulator of T-cell immune responses.

Figure 2:
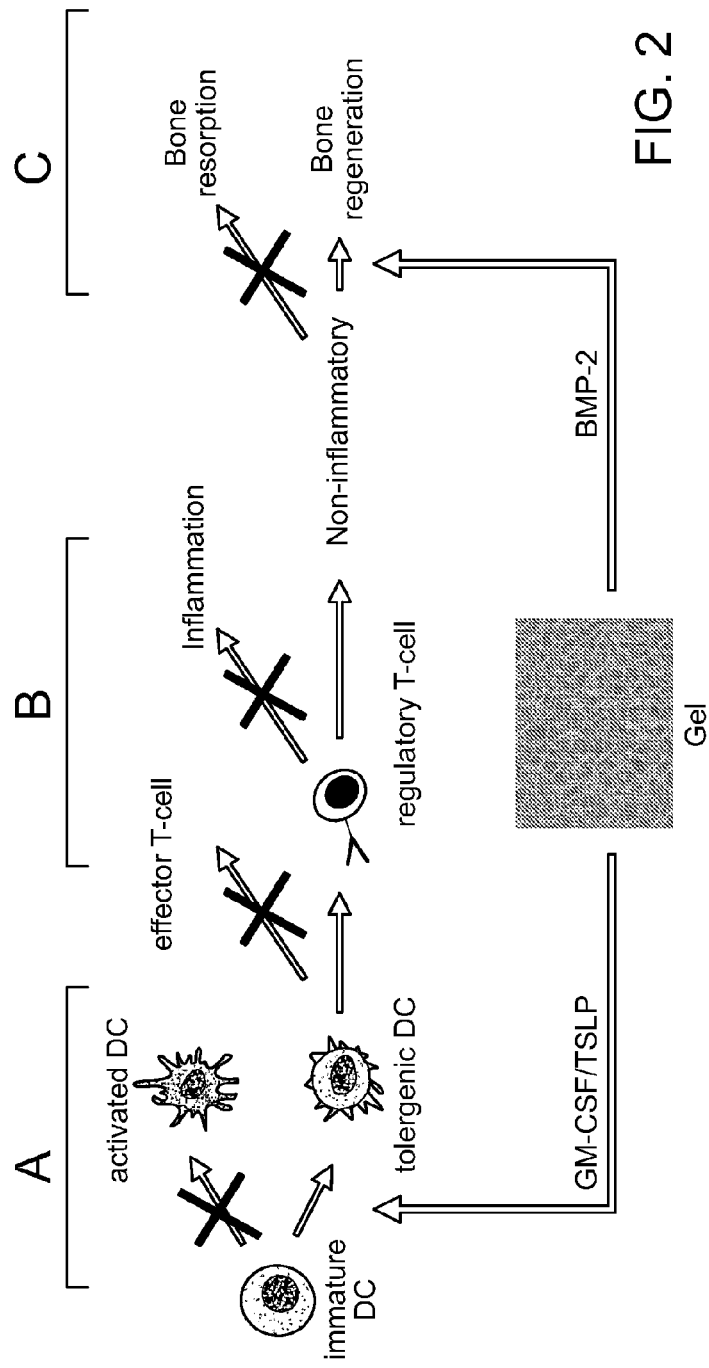
FIG. 2 is a schematic of an approach to ameliorate PD inflammation and promote bone regeneration in an embodiment of the present invention. The gel delivered into the site of inflammation first releases GM-CSF and TSLP, to promote formation of tolerant DCs (tDCs) from immature DCs, and block DC activation. The increased ratio of tolerant DCs/activated DCs promotes formation of regulatory T-cells (Tregs), and inhibit effector T-cells. This reduces process inflammation and accompanying bone resorption, and instead promotes resolution of inflammation. The gel releases pDNA encoding for BMP-2 as inflammation subsides, and local BMP-2 expression drives bone regeneration. Bracket A addresses the relation between gel-delivery of GM-CSF and TSLP and subsequent generation of tDCs. Bracket B shows the resultant impact on formation of Tregs and inflammation, and bracket C shows on-demand pDNA delivery from gels and the impact on bone regeneration following amelioration of inflammation.

Anti-inflammatory effects mediated by Tregs also result from the up-regulation of extracellular adenosine, as Tregs convert extracellular ATP to this anti-inflammatory mediator via the action of CD39 and CD73. ATP released from injured cells or activated neutrophils is implicated as a danger signal initiator or natural adjuvant, because extracellular ATP promotes inflammation. Among all lymphocyte linage cells, only Treg are reported to express both CD39 and CD73, and can also suppress adenosine scavengers. Adenosine has various immunoregulatory activities mediated through four receptors. T-lymphocytes mainly express the high affinity A2AR and the low affinity A2BR. Macrophages and neutrophils can express all four adenosine receptors depending on their activation state, and B-cells express A2AR. Engagement of A2AR inhibits IL-12 production, but increases IL-10 production by human monocytes and dendritic cells, and selectively decreases some cytotoxic functions mediated by neutrophils. The primary biological role of Treg appears to be suppression of adaptive immune responses that produce inflammatory factors. Therefore, the ability to manipulate the formation and function of Tregs provides novel therapeutic approaches to a number of inflammatory immune-associated diseases, including PD (FIG. 2). Compared to generic anti-inflammatory drugs, which require frequent dosing, it is anticipated that once Tregs are generated in sufficient numbers, they could suppress inflammation induced by PPAIR not only in the acute phase, but also over extended time periods due to the immune memory function.

Tregs are identified via their expression levels of the transcription factor FOXP3. Patients with a mutated FOXP3 gene exhibit autoimmune polyendocrinopathy (especially in type 1 diabetes mellitus and hypothyroidism) and enteropathy (characterized as 'immunodysregulation, polyendocrinopathy, enteropathy X-linked (IPEX) syndrome'). The similarity of the phenotypes between IPEX humans and Scurfy mice, which also show the FOXP3 gene mutation, suggests that FOXP3 mutation is a common cause for human IPEX and mouse Scurfy. FOXP3 gene variants (polymorphism) may also be linked to susceptibility to autoimmune diseases and other chronic infections. Importantly, FOXP3(+) cells are present in human gingival tissues, and, significantly, the expression level of FOXP3 appears to diminish in diseased gingival tissue compared to healthy gingival tissues. Even more importantly, FOXP3(+) T-cells do not express RANKL in the gingival tissues of patients who present with PD, indicating that FOXP3(+) T-cells are possibly engaged in the suppression of PPAIR. Furthermore, the Treg-associated anti-inflammatory cytokine, IL-10, is suppressed with the expression of sRANKL in human peripheral blood T cells stimulated in vitro by either bacterial antigen or TCR/CD28 ligation. Thus, FOXP3+ T-cells are implicated in the maintenance of periodontal health: (a) the diverse and exclusive expression patterns between RANKL and FOXP3 in the T-cells of human gingival tissue and (b) suppression of RANKL and other inflammatory cytokines produced by activated T-cells.

Treg cells limit the magnitude of adaptive immune response to chronic infection, preventing collateral tissue damage caused by vigorous antimicrobial immune responses. Because periodontal disease is a polymicrobial infection, it becomes relevant to elucidate how gingival tissue Tregs recognize such a huge and diverse variety of bacteria and, at the same time, regulate the adaptive effector T cells that also react to a vast number of bacteria. Several lines of evidence indicate that CD25(+)FOXP3(+)CD4(+) Treg cells are inducible from the CD25(−) CD4(+) adaptive T-cell population, especially in response to infection. These are often termed induced Treg cells (iTreg), and their induction, which is remarkably similar to the naturally-occurring Treg (nTreg) populations, is generated by peripheral activation, particularly in the presence of IL-10 or TGF-β. The diversity of T-cell receptors (TCRs) within the whole FOXP3(+) Treg population exceeds that of FOXP3(−)CD4 T cells. The presence of antigen-specific Treg has also been found in a variety of infectious diseases, including *Leishmania, Schistosoma*, and HIV. All these results are consistent with the mechanism that Treg recognize foreign antigens. Because periodontal disease is a polymicrobial infection, it becomes relevant to utilize Treg in suppressing the inflammation associated with the activated adaptive effector T-cells that also react to a vast number of bacteria.

The immune response (e.g., Treg induction) is orchestrated by a network of antigen-presenting-cells, and likely the most important of these cell types are DCs. Tissue-resident DCs routinely survey and capture antigen, and present antigen fragments to T-cells. The antigen presentation by DCs plays a key role in directing the immune response against the antigen to either immune activation or tolerance. In the healthy gingival tissue, immune tolerance against the oral commensal bacteria is induced, whereas immune activation is elicited to the periodontal pathogens in the context of PD, as demonstrated by elevated IgG antibody response to the periodontal pathogens, as described above. These two opposed outcomes, tolerance vs. activation, are controlled by the DCs present in the gingival tissue. Tolerance-inducing DCs (tDCs) are also called regulatory DCs. One method used by tDC to prevent immune activation is to generate iTreg cells during antigen presentation. The state of maturation and activation of DCs is critical to Treg development: DCs activated and maturing in response to inflammatory stimuli trigger immune responses, but immature or "semimature" DCs, in contrast, induce tolerance mediated by the generation of Tregs. The major phenotypic feature of tDC is their production of IL-10 and low or no production of IL-12 and other cytokines that prime effector T-cells. A number of signals and cytokines direct DC trafficking and activation. Multiple inflammatory cytokines mediate DC activation, including TNF, IL-1, IL-6, and PGE2, and are frequently used to mature DC ex vivo.

Granulocyte macrophage colony stimulating factor (GM-CSF) is a particularly potent stimulator of DC recruitment and proliferation during the generation of immune responses, and is useful to manipulate DC trafficking in vivo. A variety of exogenous factors including TGFβ, thymic stromal lymphopoietin (TSLP), vasoactive intestinal peptide (VIP), and retinoic acid (RA), used alone or in combination, orientate DC maturation induce tolerance, and Treg development.

Morphogens

A number of morphogens (e.g., bone morphogenetic proteins (BMPs), platelet derived growth factor (PDGF)) that actively promote bone formation by tissue resident cells are useful for prompting alveolar bone regeneration. The BMPs, members of the TGF-β superfamily, play a key role in that process. The BMPs are dimeric molecules that have a variety of physiologic roles. BMP-2 through BMP-8 are osteogenic proteins that play an important role in embryonic development and tissue repair. BMP-2 and BMP-7, the first BMPs to be available in a highly purified recombinant form, play a role in bone regeneration. BMP-2 acts primarily as a differentiation factor for bone and cartilage precursor cells towards a bone cell phenotype. BMP-2 has demonstrated the ability to induce bone formation and heal bony defects, in addition to improving the maturation and consolidation of regenerated bone. PDGF is a protein with multiple functions, including regulation of cell proliferation, matrix deposition, and chemotaxis, and has also been investigated for its potential to promote periodontal regeneration. PDGF delivery influences repair of periodontal ligament and bone, and ligament attachment to tooth surfaces. Recombinant proteins are used as the active agent in bone regeneration therapies. Alternatively local gene therapy strategies are used to deliver morphogen.

Sustained local production and secretion of growth factors via gene therapy overcomes certain limitations of protein delivery related to short half-life and susceptibility to the inflammatory environment, and also allows regulation of the timing of factor presence at a tissue defect site. Small-scale clinical trials and animal studies have documented success utilizing adenovirus gene delivery approaches, or transplantation of cell populations genetically modified in vitro prior to transplantation, to promote local expression of growth factors to drive bone regeneration. Delivery of plasmid DNA containing genes encoding for growth factors is preferred. Plasmid delivery requires large doses, and this results in expression of the transgene for about 7 days or fewer. Plasmid DNA delivery from polymer depots, increases transfection efficiency and duration of morphogen delivery.

Delivery Systems

Programming of DCs and host osteoprogenitors in situ to generate potent, and specific immune and osteogenic responses involves precisely controlling in time and space a variety of signals that act on these cells. One approach to provide localized and sustained delivery of molecules at the desired site of action is via their encapsulation and subsequent release from polymer systems. Using this approach, the molecule is slowly and controllably released from the polymer (e.g., via polymer degradation), with the dose and rate of delivery dependent on the amount of drug loaded, the process used for drug incorporation, and the polymer used to fabricate the vehicle. In addition, polymer systems permit externally regulated release of encapsulated bioactive molecules e.g., using ultrasound as the external trigger. A variety of different polymers, and varying physical forms of the polymers have been developed to allow for localized and sustained delivery of various bioactive macromolecules. Biodegradable polymers of lactide and glycolide (PLG), which are also used to fabricate GTR membranes, are used clinically for extended delivery of hormones (Lupron Depot® microspheres [Takeda Chemical], and Zoladex microcylindrical implants [Zeneca Pharmaceuticals]. PLG microspheres that sustain the release of Macrophage Inflammatory Protein (MIP-3β) are chemoattractive for murine dendritic cells in vitro. Polymer rods have also been used to locally codeliver MIP-3β with tumor lysates or antigen, and induced the recruitment of dendritic cells that were able to induce antigen-specific, cytotoxic T-lymphocyte activity that yielded anti-tumor immunity.

Intratumoral injection of GM-CSF and IL-12 loaded microspheres was shown to generate protective immunity. Alginate-derived polymer, a depot system suitable has been used as carrier for immune regulating cues and osteogenic stimuli. Alginate is a linear polysaccharide comprised of (1-4)-linked β-D-mannuronic acid and α-L-guluronic acid residues, and is hydrophilic. Alginate gels promote very little non-specific protein absorption, likely due to the carboxylic acid groups, and has an extensive history as a food additive, dental impression material, and in a variety of other medical and non-medical applications. In the pure form, it elicits very little macrophage activation or inflammatory response when implanted Sodium salts of alginate are soluble in water, but will gel following binding of calcium or other divalent cations to yield gels that may readily be introduced into the body in a minimally invasive manner. These material systems have the ability to quantitatively control DC trafficking in vivo, and to specifically regulate DC activation. Such material systems provide control of host immune and inflammatory responses, while simultaneously providing signals that actively promote periodontal tissue regeneration.

Chronic Inflammation in Periodontal Diseases (PD)

Chronic inflammation accompanying PD promotes bone resorption via involvement of immune cells (FIG. 1). Materials, hydrogels in particular, and therefore introduced into diseased tissue and first deliver signals to alter the balance of the immune response to ameliorate inflammation, and subsequently provide on-demand, localized delivery of pDNA encoding BMP-2. These compositions and methods lead to significant bone regeneration (FIG. 2). DCs are targeted as a central orchestrator of the immune system, are potent antigen-presenting cells. Other cell types may provide targets for immune modulation, and the strategies described herein are applicable to those cell types as well. This invention provides for material systems that program DCs in order to alter the balance between Tregs and effector T-cells to ameliorate chronic inflammation. The ability of Tregs to produce anti-inflammatory cytokines such as IL-10, and suppress adaptive immune responses makes them an attractive target to ameliorate chronic inflammatory processes. Material systems offer the opportunity to control more precisely the numbers, trafficking, and states of DCs and T-cells in the body, in combination with their ability to provide osteoinductive stimuli.

In another aspect of the invention, bone regeneration is promoted via an inductive approach that involves localized delivery of plasmid DNA encoding BMP-2. Local gene therapy is used to promote osteogenesis, and pDNA approaches in particular. The therapeutic system combines osteoinductive factor delivery with the active quenching of inflammation, and the externally-triggered release of the osteoinductive factor once inflammation is diminished. In particular embodiments, alginate hydrogels are used as the material platform. These gels are introduced into the body in a minimally invasive manner and have proven useful to deliver proteins, pDNA and other molecules, and regulate their distribution and duration in vivo. Alginate hydrogels are particularly useful for the ultrasound-mediated triggered release.

Further regarding the material system to recruit large numbers of host DCs and to effectively induce these DCs to a tolerant state (tDCs), GM-CSF are a cue to recruit DCs and TSLP pushes recruited DCs to the tDC phenotype. The GM-CSF is released into the surrounding tissue to recruit DCs, promote their proliferation, and generally increase the numbers of immature DCs, while appropriate TSLP exposure converts these cells to tDCs. The relation between local GM-CSF and TSLP delivery and tDCs, leads to generation of tDCs while minimizing the numbers of activated DCs.

One embodiment characterizes the action of GM-CSF and TSLP, and their delivery via alginate gels. GM-CSF is a potent signal for DC recruitment and proliferation, and the GM-CSF concentration is key to its ability to inhibit DC maturation and induce tolerance. TSLP generates tDCs due to its ability to initiate and maintain T-cell tolerance. A number of other factors have been identified that enhance formation of tDCs and Tregs, including vasoactive intestinal peptide, Vitamin D and retinoic acid, and these may be used alone or in combination with TSLP.

Materials containing the GM-CSF and TSLP with the appropriate spatiotemporal presentation to recruit and develop tDCs in situ were developed. The effects of continuous GM-CSF and TSLP exposure (10-500 ng/ml GM-CSF; 10-200 ng/ml TSLP) are described herein. FACS analysis and other analytic method used are to characterize DC population by deleting markers of maturation, e.g. MHCII, CD40, CD80 (B7-1), CD86 (B7-2), and CCR7, evaluating their secretion of cytokines (TNF-α, IL-6, IL-12, IFN-α, IL-10 tDC are identified by low levels of CD40, CD80, CD86, MHCII, and high level of IL-10). The effects of gradients of GM-CSF on cell recruitment is evaluated using a diffusion chamber.

Alginate gels with varying rheological/mechanical properties and degradation rates are created through control over the polymer composition, molecular weight distribution, and extent of oxidation. The alginate formulation used was binary alginate composed of 75% oxidized low molecular MVG alginate and 25% high molecular weight MVG alginate crosslinked with calcium. The scaffold compositions allows the localized delivery of GM-CSF and TSLP. The release rates of GM-CSF and TSLP depends on the gel cross-linking and degradation rate, e.g., the gels provide sustained release for a time-frame ~1-2 weeks. These molecules are incorporated directly into the gel during cross-linking, as documented previously for other growth factors and pDNA. If the release occurs too rapidly (e.g., gel depleted within 1-2 days), the release may be retarded by first encapsulating the factors in PLG microspheres, that are then incorporated into gels, alginate gels, during cross-linking. In this approach, release from the PLG particles regulates overall release, and this rate is tuned by altering the MW and composition of the PLG. The release rates of the GM-CSF and TSLP are analyzed in vitro using iodinated factors, following factor encapsulation. For example, GM-CSF is released over a period of 2 days to 3 weeks. The bioactivity of the released factors is confirmed using standard cell-based assays known in the art.

Gels are injected in the gingival tissue of mice at the site of alveolar bone loss (e.g., 1.5 µl).

The ability of GM-CSF and TSLP to recruit host DCs (FIG. 4) indicates that an appropriate GM-CSF dose ranges from 200 ng-10,000 ng. The following factors were used to evaluate.

| Mouse cytokine/chemokine panel-24-Plex | | |
|---|---|---|
| Cytokine | Chemokine | Chemokine receptor(s) |
| TNF-a | Eotaxin | CCR3 |
| G-CSF | IP-10 | CXCR3, CXCR3B |
| GM-CSF | KC | CXCR2 |
| M-CSF | MCP-1 | CCR2** |
| IFN-γ | MIG | CXCR3 |
| IL-1β | MIP-1a | CCR1, CCR5** |
| IL-2* | MIP-1β | CCR5** |
| IL-4* | MIP-2 | CXCR2 |
| IL-6 | RANTES | CCR1, CCR3, CCR5** |
| IL-7* | | |
| IL-9* | | |
| IL-10 | | |
| IL-12 (p70) | | |
| IL-15* | | |
| IL-17 | | |

*γc-receptor-dependent cytokines
**reported to be expressed on Treg

Presentation of GM-CSF yields large numbers of recruited DCs, and a correlation between GM-CSF concentrations and DC maturation obtained (e.g., DCs maturation be inhibited at high GM-CSF concentrations). In other words, by controlling the release kinetics and dose of GM-CSF, it can act not only as a recruiting factor, but a tolerogenic factor. For example, at high concentrations of GM-CSF dendritic cells can become tolerogenic. If insufficient numbers of DCs are recruited with GM-CSF, exogenous Flt3 ligand release from gels is optionally used. TSLP is critical to direct the activation of DCs, particularly in the presence of inflammatory signals (e.g., LPS). The dose of TSLP relative to GM-CSF contributes to this phenomena. For example, the range for each factor in a scaffold is 0.1 µg to 10 µg, e.g., scaffolds were made using 1 µg of each. TGF-beta, IL-10, rRetinoic acid, Vitamin D, and/ or vasoactive intestinal peptide can optionally be added or used in place of TSLP. Alginate or PLG are preferred polymers; however other polymers and methods of TSLP and GM-CSF immobilization within the gels are known in the art.

Modulating PD-related inflammation with materials presenting GM-CSF and TSLP induces the formation of Treg cells and ameliorates inflammation in mice with PD. Inflammatory bone resorption found in human patients with PD was shown to be elicited by activated adaptive immune T-cells (and B-cells) which produce bone destructive RANKL as well as collateral inflammatory damage caused by expression of proinflammatory cytokines (IL-1-β, IFN-γ) from T-cells and other accompanying inflammatory cells. Suppressing the activation of T cells resolves the chronic inflammation and bone resorption associated with periodontal disease. Locally inducing anti-inflammatory Treg cells (iTregs) using the GM-CSF/TSLP material gel system shows tDCs generated by GM-CSF and TSLP formation of iTregs and inhibit the inflammatory bone resorption induced by activation of adaptive immune responses. The level of inflammation is monitored by measurement of inflammatory chemical mediators present in gingival tissue ($PGE_2$, nitric oxide, ATP and adenosine) and presence of inflammatory cells.

Induction of tDCs in Periodontal Disease

The PD mouse model induces vertical periodontal bone loss following activation of immune responses to orally harbored bacteria, termed "Periodontal Pathogenic Adaptive Immune Response (PPAIR)". Vertical bone loss is most closely associated with the human form of periodontal disease, and this PD model permits evaluation of: (1) inflammatory response by measurement of proinflammatory cytokines in the tissue homogenates; (2) localization and number of FOXP3+ Treg cells using FOXP3-EGFP-KI mice; (3) phenotypes of inflammatory cells by triple-color confocal microscopy and flow cytometry; (4) presence of bone destructive osteoclasts (TRAP), bone-generating osteoblasts (Periostin/alkaline phosphatase [ALP]), and ligament fibroblasts (Periostin/ALP); and (5) the level of bone resorption. Instead of a membrane-based GTR system, the selection of a gel-based delivery system is useful as a minimally invasive (non-surgical) material system to remodel vertical bone loss. More specifically, one gingival injection of gel appropriately delivers GM-CSF/TSLP. The socket wall at the vertical bone resorption lesion provides the space to retain the material, without the aid of a scaffold. After the successful demonstration of the principles underlying this approach, these gels are used as a supplement to current membrane-based GTR systems, or GTR systems that similarly provide these cues could be developed.

It is striking that increased numbers of FOXP3+ Treg cells were observed along with IL-10+CD11c+DC cells in the mouse periodontal bone loss lesion where GM-CSF/TSLP-gel was injected (FIG. 9). These data indicate that tDCs enhance local enrichment of (or promote generation of) FOXP3+ Treg cells. The GM-CSF/TSLP-delivered gel to induce tDCs. These aspects shows the kinetics of iTreg induction by GM-CSF/TSLP delivery in alginate gels in periodontal bone loss lesions. The impact of the local formation of iTreg cells on the bone remodeling system (i.e., osteoclasts vs. osteoblasts and ligament fibroblasts) and continuation of bone resorption was observed.

Figure 3A:
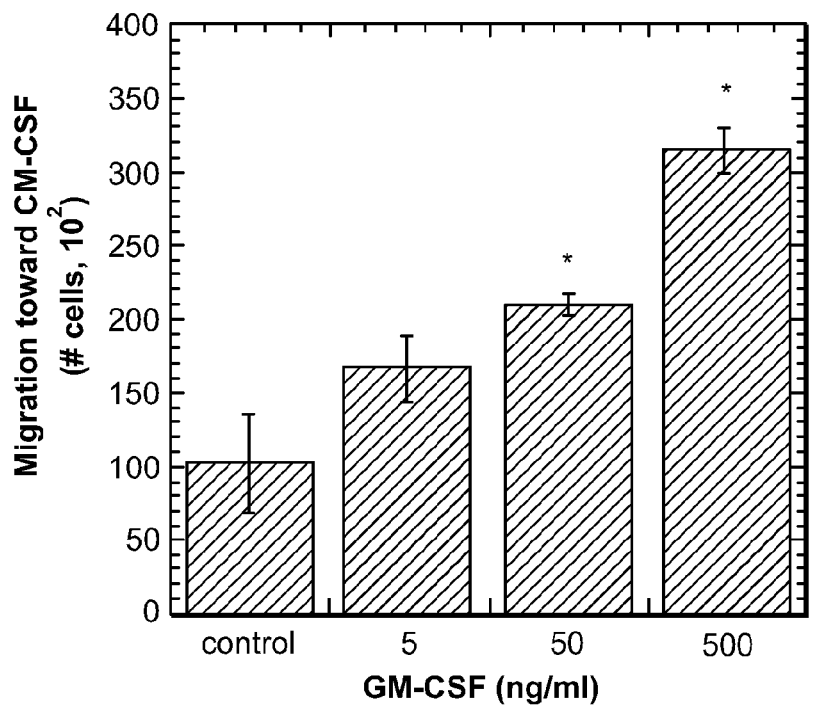
FIG. 3 shows data related to the concentration dependent effects of GM-CSF on DC proliferation, recruitment, activation and emigration in vitro. (3A) shows the in vitro recruitment of JAWSII DCs induced by the indicated concentrations of GM-CSF in transwell systems. Migration counts measured at 12 hours. (3B) is the effects of GM-CSF concentration on the proliferation of JAWSII DCs. 0 (white bar), 50 (grey bar), and 500 ng/ml (black bar) of GM-CSF. (3C) shows the effects of the indicated concentrations of GM-CSF on JAWS II DC emigration from the top wells of transwell systems toward media supplemented with 300 ng/ml CCL19. Migration counts taken at 6 hours. (3D) are representative photomicrographs of TNF-α and LPS stimulated JAWSII DCs cultured in 5-50 or 500 ng/ml GM-CSF and stained for the activation markers MHCII and CCR7. Scale bar in (3D) –20 µm. Values in (3A-3C) represent mean and standard deviation (n=4); * P<0.05; ** P<0.01
Figure 3B:
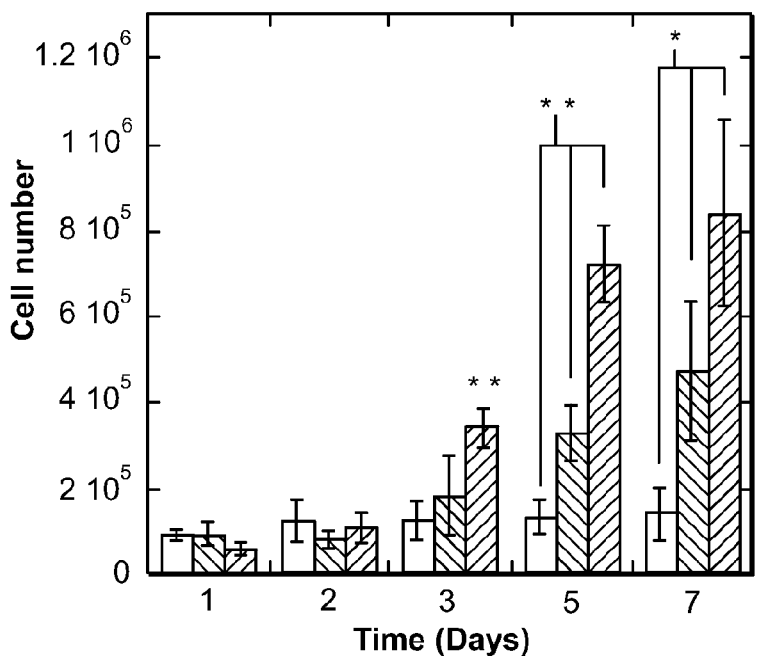
Figure 3C:
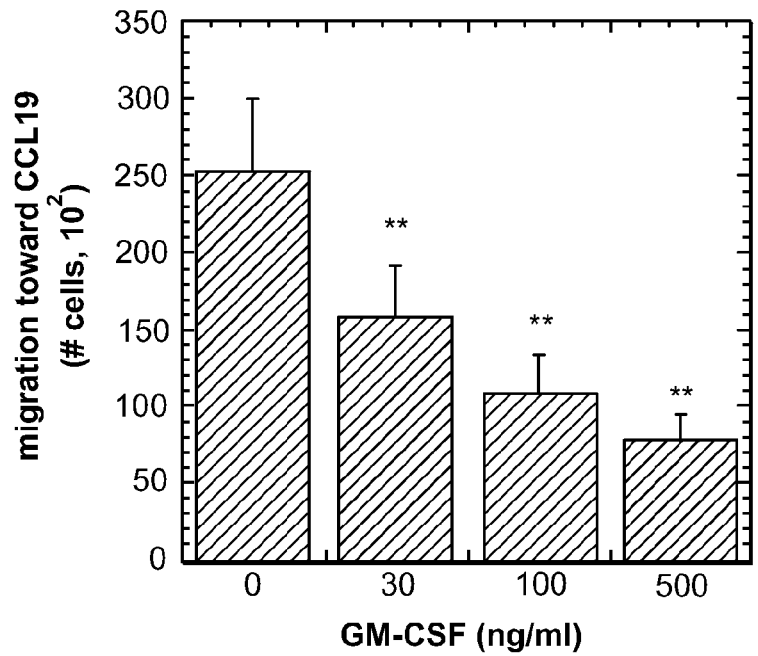
Figure 3D:
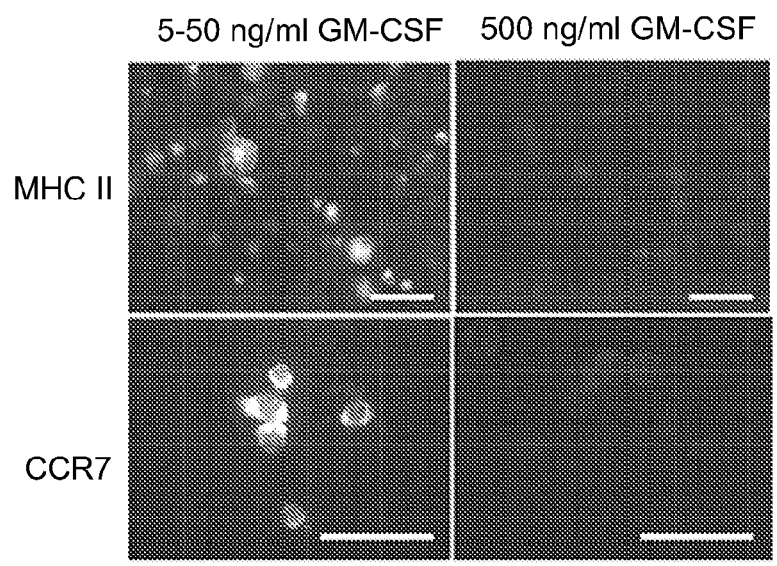

GM-CSF enhanced DC recruitment and proliferation in a dose-dependent manner (FIG. 3A-3B). High concentrations (>100 ng/ml) of GM-CSF, however, inhibited DC migration toward the LN-derived chemokine CCL19 (FIG. 3C). Immunohistochemical staining revealed that the high concentrations of GM-CSF also suppressed DC activation via TNF-α and LPS stimulation by down-regulating expression of MHCII and the CCL19 receptor CCR7 (FIG. 3D). These results indicate that local, high GM-CSF concentrations recruit large numbers of DCs and prevent their activation to a phenotype capable of generating a destructive immune response.

The GM-CSF/TSLP the recruitment of DCs and subsequent activation of iTregs, and provides local, material-based delivery of pDNA encoding osteogenic molecules in vitro leading to bone regeneration.

Figure 4A:
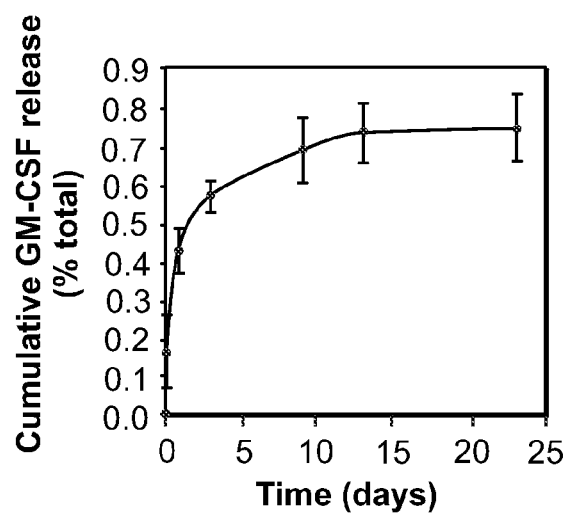
FIG. 4 presents data on the in vivo control of DC recruitment and programming (4A) is the release profile of GM-CSF from polymers that demonstrates a large initial burst, to create high early concentrations of GM-CSF in tissue. (4B) shows H&E staining of tissue sections following explanation from subcutaneous pockets in the backs of C57BL/6J mice after 14 days: Blank polymers, and GM-CSF (3000 ng) loaded polymers. (4C) shows FACS plots of cells isolated from explanted polymers after 28 days and stained for the DC markers, CD11c and CD86 implanted. Numbers in FACS plots indicate the percentage of the cell population positive for both markers. (4D) is the percentage of total cells that were positive for the DC markers CD11c and CD86, in blank (—○—) and GM-CSF (—●—) loaded polymers as a function of time post implantation. (4E) The total number of DCs isolated from blank (—○—) and GM-CSF (—●—) loaded polymers as a function of time post implantation. (4F) The fractional increase in CD11c(+)CD86(+) DCs isolated from polymers at day-14 after implantation in response to doses of 1000, 3000 and 7000 ng of GM-CSF as compared to the control. Scale bar –500 µm. Values in 4A, 4D, 4E, and 4F represent mean and standard deviation (n=4 or 5); * P<0.05; ** P<0.01.
Figure 4B:
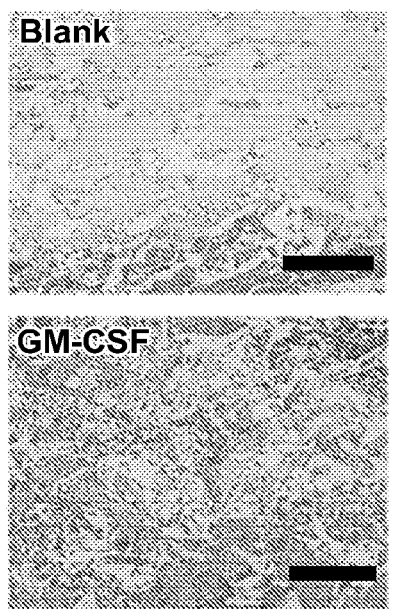
Figure 4C:
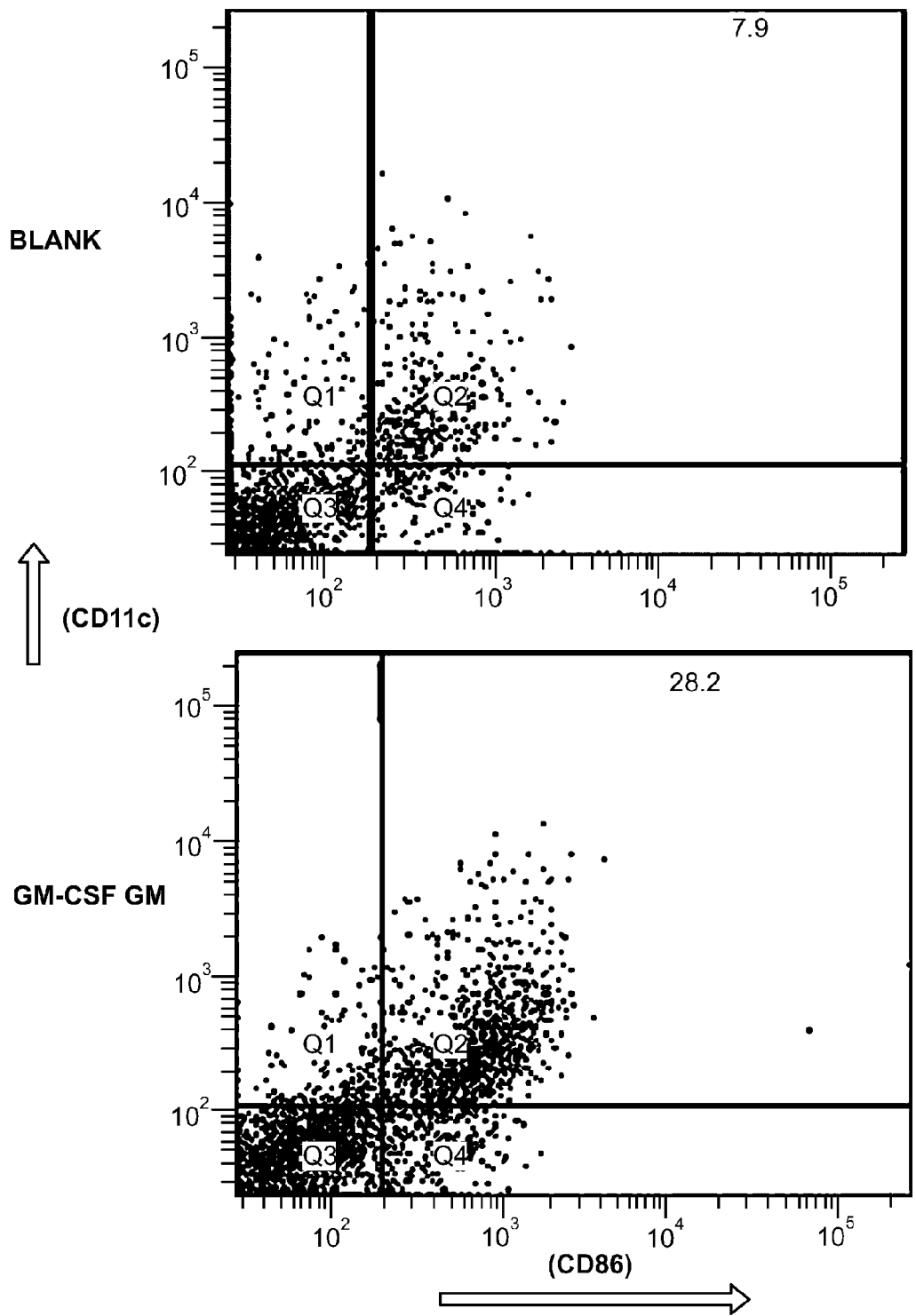

The polymer delivery vehicle presents GM-CSF in a defined spatiotemporal manner in vivo, following introduction into the tissue of interest. Exemplary vehicle quickly release approximately 60% of the bioactive GM-CSF load within the first 5 days, followed by slow and sustained release of bioactive GM-CSF over the next 10 days (FIG. 4A), to allow diffusion of the factor through the surrounding tissue and effectively recruit resident DCs. Polymers were loaded with 3 μg of GM-CSF and implanted into the dorsal subcutaneous site of C57BL/6J mice. Histological analysis at day-14 revealed that the total cellular infiltration at the site was significantly enhanced compared to control (no incorporated GM-CSF) (FIG. 4B). FACS analysis for CD11c(+)CD86(+) DCs showed that GM-CSF increased not just the total cell number, but also the percentage of infiltrating cells that were DCs (FIGS. 4C-4D). Enhanced DC numbers at the material-implanted site were sustained over time (FIG. 4E). As predicted by in vitro testing, the effects of GM-CSF on in vivo DC recruitment were dose-dependent (FIG. 4F).

Figure 5A:
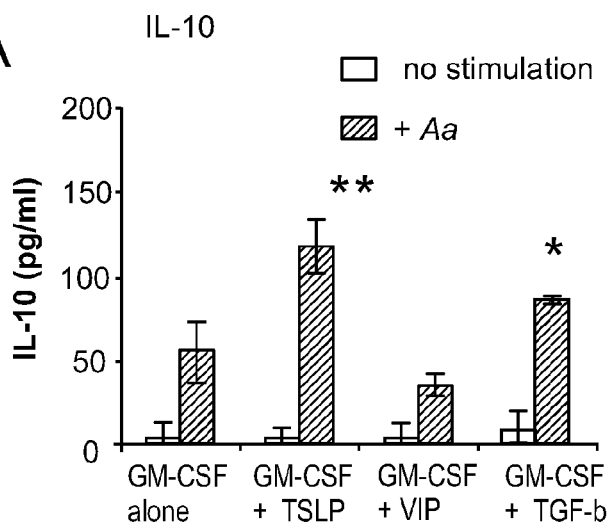
FIGS. 5A-5C shows cytokine production by CD11+ DC induced in vitro from bone marrow cells with GM-CSF in the presence or absence of TSLP, VIP, or TGF-β (7 day incubation). The in vitro incubation of mononuclear cells isolated from the bone marrow (BM) of C57BL/6 mice with GM-CSF and TSLP (100 ng/ml, respectively) for 7 days up-regulated the differentiation of tolerogenic DC that produced high IL-10 (5A) and low IL-6 (5B) and IL-12 (5C). While TGF-β (100 ng/ml) also showed a similar trend to TSLP in the induction of tolerogenic DC, VIP did not up-regulate the ability of DCs to produce IL-10. The surface phenotypes of CD11c+DC in the BM culture were monitored by flow cytometry and the proportionality of each phenotype is expressed as a percent (%) of the total mononuclear cells (MNC) (FIG. 5, Table 1). The double-color confocal microscopy showed that the gingival injection of gel (1.5 µl) with GM-SCF (1 µg) and TSLP (1 µg) increased CD11c+ cells which produce IL-10 in the mouse periodontal bone loss lesion (5E; 7 days after injection), compared to the control bone loss lesion which did not received injection (5D).
Figure 5B:
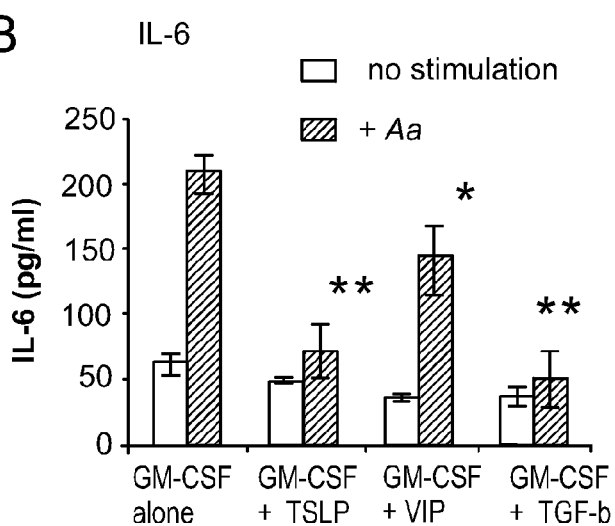
Figure 5C:
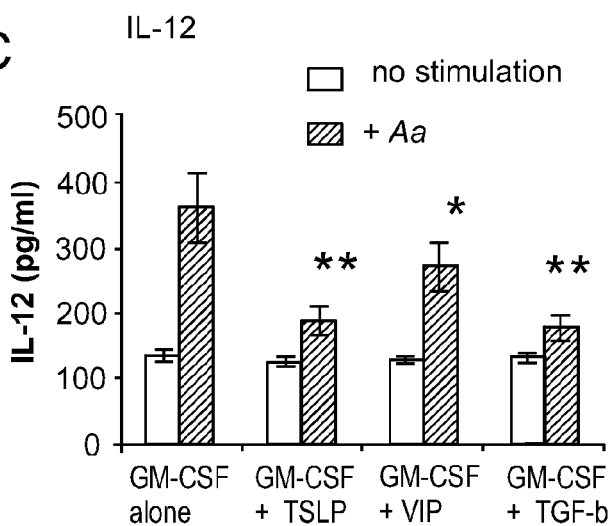
Figures 5, 5D, 5E:
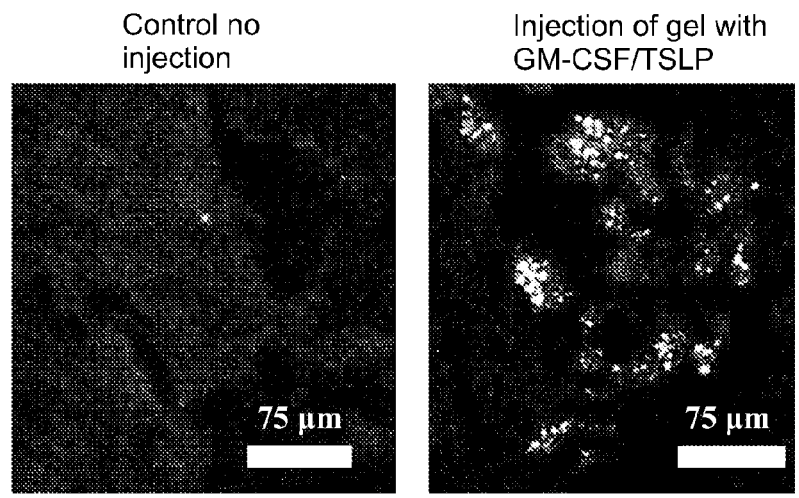
FIG. 5 reflects the potency of a material system that delivers TSLP and GM-CSF to PD lesion in induction of tolerogenic DC.

The present invention provides for a material-based local application of GM-CSF with appropriate DC influencing factors that leads to tolerogenic DCs (tDCs), and subsequent enrichment of iTreg cells. Candidate biofactors include thymic stromal lymphopoietin (TSLP), vasoactive intestinal peptide (VIP), and transforming growth factor-beta (TGF-β). Screening is based on the induced DC's anti-inflammatory properties. The in vitro incubation of mononuclear cells isolated from the bone marrow (BM) of C57BL/6 mice with GM-CSF in the presence of TSLP, VIP, or TGF-β led to diminished expression of the proinflammatory cytokines IL-6 and IL-12, in response to bacterial stimulation, as compared to the DC induced by GM-CSF alone (FIG. 5). In response to bacterial challenge, however, GM-CSF/TSLP-induced DC produced the highest levels of the anti-inflammatory cytokine, IL-10, as compared to the other combinations. Interestingly, the addition of TSLP did not alter the yield of GM-CSF-mediated differentiation of DC(CD11c+/CD86+ in total BM cells; GM-CSF alone, 14.7% vs. GM-CSF+TSLP, 14.6%) from the BM cells compared to the low yield of CD11c+/CD86+DC with TGF-b (10.5%) (FIG. 5, Table 1). Overall, these observations that the combination of GM-CSF with TSLP efficiently induces DC with an anti-inflammatory phenotype.

To demonstrate that material-based delivery of GM-CSF/TSLP induces tolerogenic DC locally in vivo, polymer vehicles containing a mixture of GM-CSF (1 μg) and TSLP (1 μg), as well as GM-CSF alone (1 μg), were injected into the periodontal bone resorption socket of FOXP3-EGFP-KI mice (C57BL6 background), and were evaluated to determine their effects on the local DC cells. Seven days later, a remarkable increase in the proportion of CD11c+IL-10+DC was observed in the periodontal socket of mice receiving polymers containing GM-CSF/TSLP, as compared to the injection of control empty polymer (FIG. 6). These findings indicate that the local delivery of TSLP and GM-CSF by the polymer can positively skew the GM-CSF-mediated differentiation of DC with anti-inflammatory activity, represented by high IL-10 expression, in the previously developed periodontal bone resorption lesion.

Figure 6A:
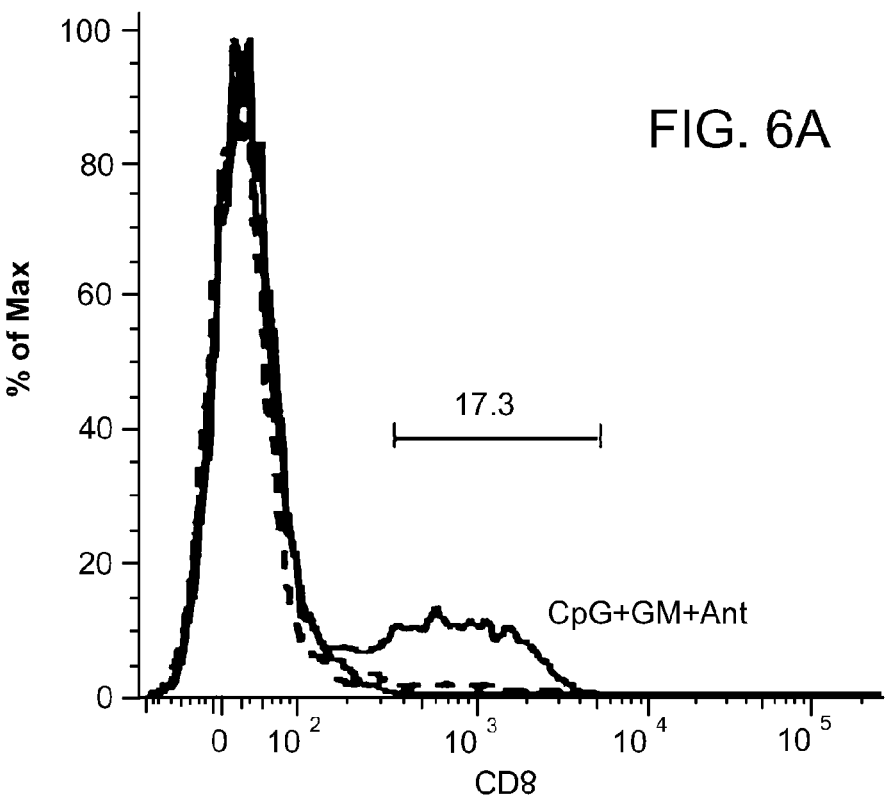
FIG. 6 demonstrates control over local T-cell numbers, and antigen-specific CD8 T-cells. (6A) FACS histograms of CD8 (+) cell tissue infiltration with blank vehicle (gray line), vehicle loaded with 3000 ng GM-CSF and 100 µg CpG-ODN alone (dashed line), and vehicle loaded with GM-CSF and antigens (black line). (6B) Characterization of TRP2-specific CD8 T-cells. Splenocytes from naïve mice (naïve) and mice receiving vehicles containing antigen+GM-CSF+CpG at day 30 (vaccinated) were stained with anti-CD8-FITC Ab, anti-TCR-APC Ab, and Kb/TRP2 pentamers. The ellipitical gates in the upper right quadrant represent the TRP2-specific, CD8 (+) T cells and numbers provide percentage of positive cells. Values represent the mean.
Figure 6B:
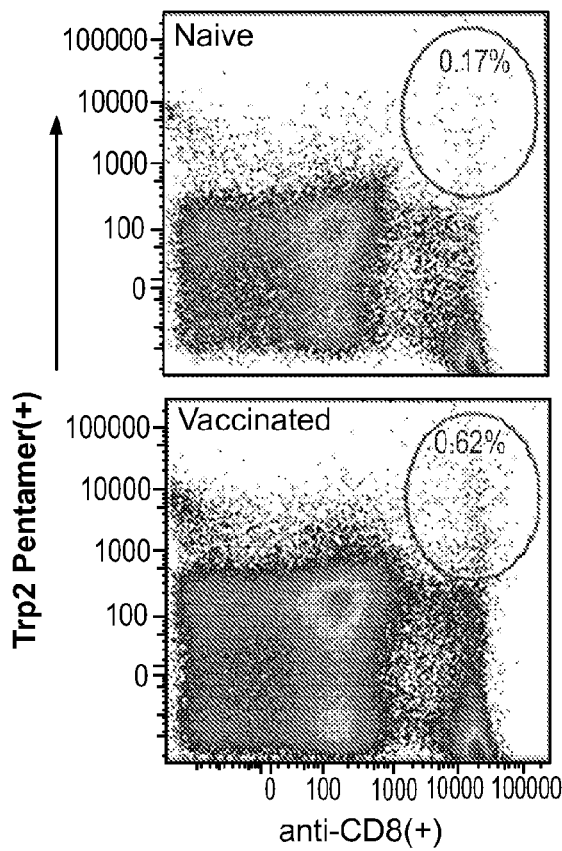

The ability of the material systems of the present invention not only to recruit DCs, but also to regulate T-cell generation, was also examined. These studies were performed to elicit an anti-tumor immune response against melanoma via inclusion in the material of "DC activators" (cytosine and guanosine-rich oligonucleotides; CpG-ODN; TLR9 ligand that elicits danger signal in DC, and melanoma-specific antigen, along with the GM-CSF. Nevertheless, although such approach "to activate immune response" contradicts to the approach "to suppress inflammatory-immune response," the results demonstrate the ability to generate specific and quantitative immune responses with the material systems. Specifically, over 17% of the total cells at the site were CD8(+) compared to the control non-treated site (<1% CD8) (FIG. 6A). This result indicates that the number of T-cells infiltrating tissue adjacent to the polymeric delivery vehicle was enriched with delivery of GM-CSF, antigen and CpG-ODGN. The generation of a specific memory immune response was shown by staining isolated splenocytes with MHC class I/tyrosinase-related protein (TRP2). This analysis revealed a significant expansion of TRP2-specific CD8 T-cells in mice vaccinated with GM-CSF, antigen and CpG-ODN (0.55% splenocytes, $1.57 \times 10^5 + 5.5 \times 10^4$ cells) in comparison to matrices presenting lower CpG doses, either 0 μg or 50 μg (0.17% and 0.25% of splenocytes) (FIG. 6B). As indicated above and in the next section (FIG. 10), the findings that the materials delivering GM-CSF and CpG oligonucletides activate anti-tumor CD8 T-cells by activation of DC expressing IL-12, and in contrast when delivering GM-CSF and TSLP activate Treg cells by activation and differentiation of tolerogenic DC that produce IL-10, confirm the power of this approach to regulate immune responses.

The mouse model of PD was also used to study the efficacy of minimally invasive material systems that can suppress PPAIR, as well as induce regeneration in the bone loss lesion of PD, which meets the immuno-pathological fundamentals found in humans. This model develops RANKL-dependent periodontal bone loss upon induction of adaptive immune responses to the mouse orally colonized bacteria. By using the 16S rRNA sequence method, it was discovered herein that in-house bred BALB/c mice harbor the oral commensal bacterium *Pasteurella pneumotropica* (Pp). Pp is facultative anaerobic Gram(−) bacterium, and, similar to Aa, Pp is resistant to Bacitracin and Vancomycin, but susceptible to Gentamycin. Aa and Pp, as well as *Haemophilus*, belong to the same phylogenic family of Pasteurellaceae. Pp outer membrane protein OmpA is a homologue of Aa Omp29. Natural oral colonization of BALB/c mice with Pp per se is latent and has not shown any pathogenic features because immunological tolerance is induced to this oral commensal Pp. Supporting this, *Pasteurella* was also reported to be commensal in the gingival crevice of ferrets. Thirty days after either (1) adoptive transfer of the Aa-reactive Th1 line; or (2) peripheral immunization (dorsal s.c. injection) with fixed whole Aa to the Pp-harboring mice, periodontal bone loss (horizontal) was demonstrated, along with elevated IgG antibody response to Aa Omp29, and increased production of TNF-α and RANKL in the gingival tissue. The T-cells infiltrating in the gingival tissue expressed RANKL in the group of PD-induced mice, but not in the control group. Furthermore, systemic administration of OPG-Fc inhibited the periodontal bone loss induced in this mouse PD model, indicating that the induced periodontal bone loss is RANKL-dependent. The Aa immunization to the "Pp-free" BALB/c mice did not show periodontal bone loss, indicating that orally colonized commensal Pp bacteria that deliver the T-cell antigen to mouse gingival tissues is required for bone loss induction. Serum IgG of Aa-immunized Pp+ mice reacted to both Aa and Pp, but not other oral bacteria or *E. coli* examined. This very distinct cross-reactivity between Aa Omp29 and Pp OmpA allows the induction of PPAIR that results in periodontal bone loss by immunization of Pp+ mice with Aa antigen. Indeed, Omp29 is one of the most prominent antigens recognized by serum IgG antibody in LAP patients infected with Aa.

Although mouse models of *P. gingivalis* oral infection have been most frequently investigated, these *P. gingivalis* infection models appear to display mechanisms different from PPAIR. This occurs because induction of adaptive immune responses displayed by elevated IgG antibody to P. gingivalis antigen ameliorates, instead of augments, the P. gingivalis-infection-mediated periodontal bone loss, which is not necessarily representative of human periodontal bone resorption. Another shortcoming of the P. gingivalis-induced mouse PD model derives from the induction of only "horizontal periodontal bone loss," while human PD is characterized by both "horizontal" and "vertical" periodontal bone loss. Although a number of etiological causes are proposed, horizontal bone loss is said to occur when chronic periodontal disease progresses moderately, while vertical bone loss is indicated when severe recurrent periodontitis or severe acute periodontitis progresses. The difference is important in the context of the proposed study because, while "horizontal" periodontal bone loss can be maintained by non-surgical periodontal treatment, "vertical bone loss" is, in fact, the clinical case where GTR surgery is required (FIG. 8).

Vertical periodontal bone loss with inflammatory connective tissue in mouse PD model, using the C57BL/6 strain mice, which followed the same protocol as published for BALB/c strain, demonstrated massive irreversible "vertical" periodontal bone loss (FIG. 7). This mirrors the periodontal bone loss found in most human patients with severe PD because, once having developed, vertical bone loss remains, even after the resolution of severe inflammation. For example, bone decay at the tooth extraction socket of mice is completely filled with new bone within 15 days. In contrast, vertical bone loss induced by PPAIR remains, indicating a significant difference in bone regeneration processes between bone loss caused by tooth extraction and by PD. It is noteworthy that few of the previously published animal models of PD develop vertical periodontal bone loss, and most of the periodontal bone loss induced in these animal models seems to develop horizontally and to be reversible after the resolution of inflammation. Therefore, this newly established mouse model, provides the ideal platform with which to evaluate minimally invasive material systems that downregulate inflammation as well as induce regeneration of lost bone. As illustrated in FIG. 7 (7g: control; 7h: PD lesion), the PD mice develop vertical bone loss filled with inflammatory connective tissue accompanied by TRAP+ osteoclast cells. Thus, minimally invasive material systems, such as the GM-CSF/TSLP delivery polymer described herein, can be administered to the inflammatory bone loss lesion such that both inflammatory response and bone regeneration in the bone loss lesion can be evaluated.

Figure 8A:
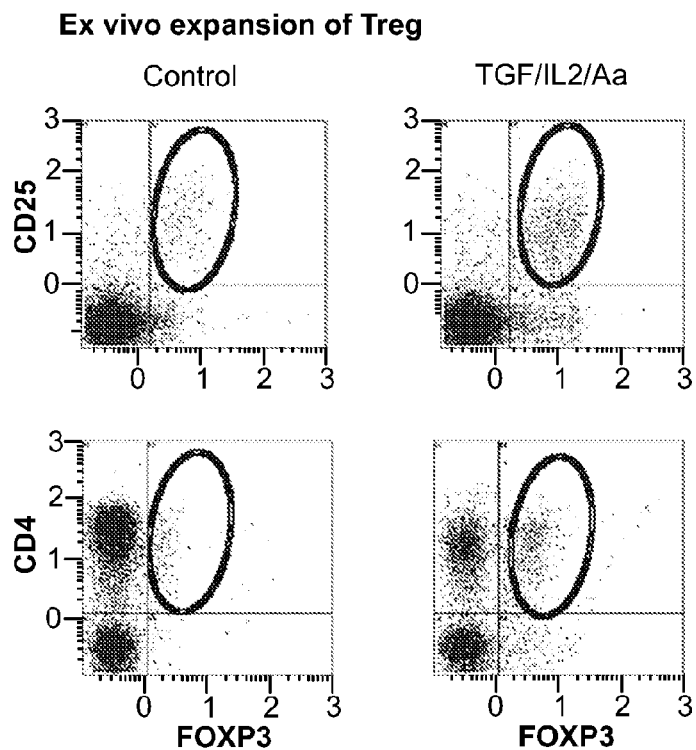
FIG. 8 demonstrates adoptive transfer of ex vivo-expanded Treg to Pp-harboring mice abrogated periodontal bone resorption induced by PPAIR. Following the protocol reported by Zheng et al., these result show ex vivo expansion of FOXP3+ CD25+ T cells by culture of spleen cells isolated from Aa-immunized mice (i.p. injection of Aa $10^{10}$/mouse) in the presence of recombinant human TGFb1 (Peprotech), mouse IL-2 (Peprotech), and fixed Aa, as antigens. After ex vivo stimulation for 3 days, the percentage of FOXP3+ CD25+ Treg cells in the total lymphocytes increased from 5.5% on day-0 to 15.0% on day-3 (upper 2 figures). Similarly, the percentage of FOXP3+CD4+ Treg cells also increased in the culture (lower 2 figures). After 6 days of ex vivo stimulation, the percentage of FOXP3+CD25+ cells reached 23.3% of the total lymphocytes and 79.8% of the total CD4 T cells. The CD4+ cells were isolated by the magnet beads-based negative selection technique (TGF/IL-2/Aa/CD4+ T cells). TGF/IL-2/Aa/CD4+Treg cells were labeled with CFSE (5 µM, in PBS, 8 min, MolecularProbe) and adoptively transferred ($10^6$/mouse). The localization of CFSE-labeled cells was confirmed by flow cytometry in gingival tissue and cervical lymph nodes (not shown). The TGF/IL-2/Aa/CD4+Treg cells ($2 \times 10^4$/well) were treated with Mitomycin C (MMC) and co-cultured with Aa-specific Th1 effector cells ($2 \times 10^4$/well) in the presence of MMC-treated spleen APC ($2 \times 10^5$/well) and Aa antigens. CD25+ cells in original spleen CD4+ T cells were depleted by cytotoxic anti-CD25 monoclonal antibody (PC61, rat IgG2a, Pharmingen) in the presence of mouse complement sera (Sigma). Such CD25-depleted spleen CD4+ T cells were also included after adjusting the cell number. Proliferation of Th1 effector cells was monitored by 3H-thymidine assay (4 days), and sRANKL concentration in the culture supernatant was measured by ELISA (8B). The TGF/IL-2/Aa/CD4+ cells were also adoptively transferred into Pp-harboring mice, and bone resorption (8C), concentration of IFN-g (8D), sRANKL (8E) and IL-10 (8F) in the gingival tissue homogenates were all measured on Day-30. *, Significantly different from control by Student's t test (P<0.05). **, Significantly different from the Aa (s.c.) injection alone (*) by Student's t test (P<0.05).
Figure 8B:
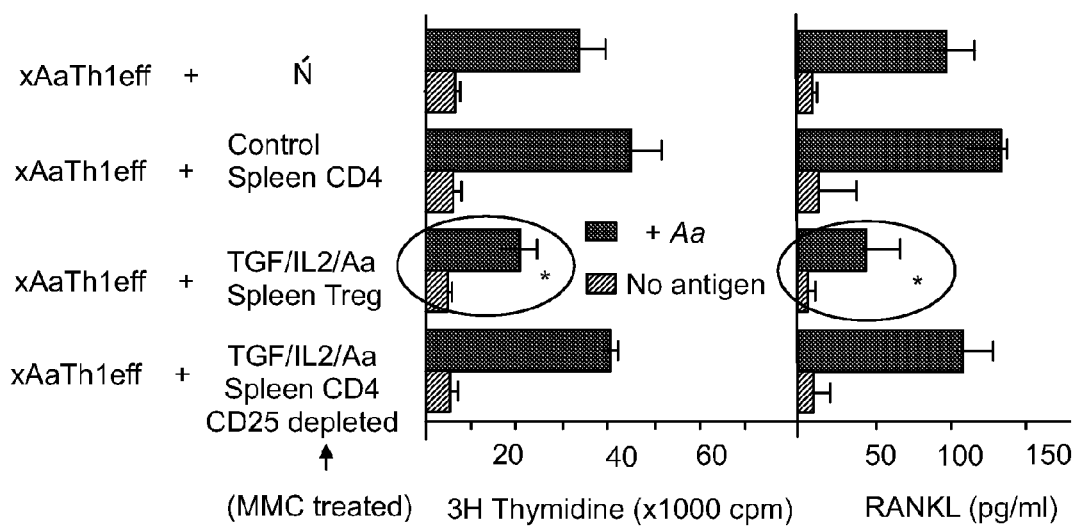
Figure 8C:
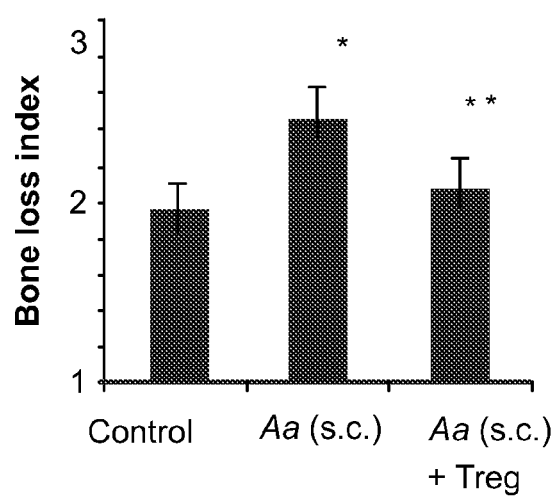
Figure 8D:
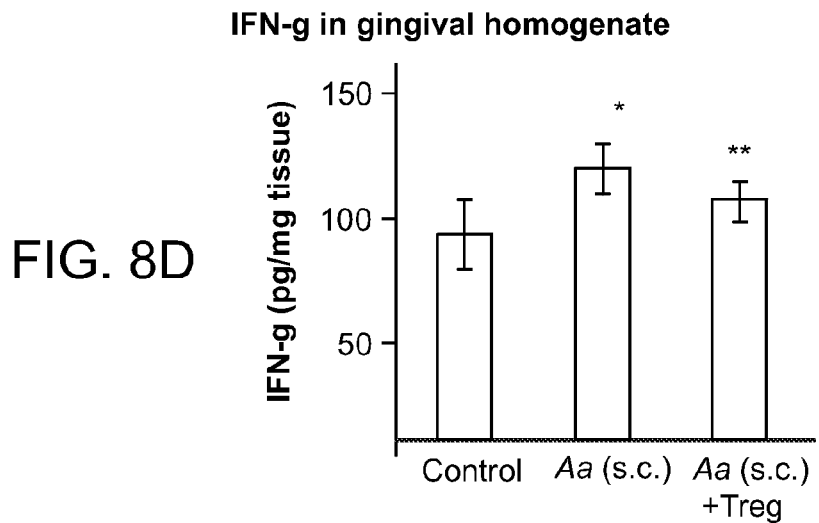
Figure 8E:
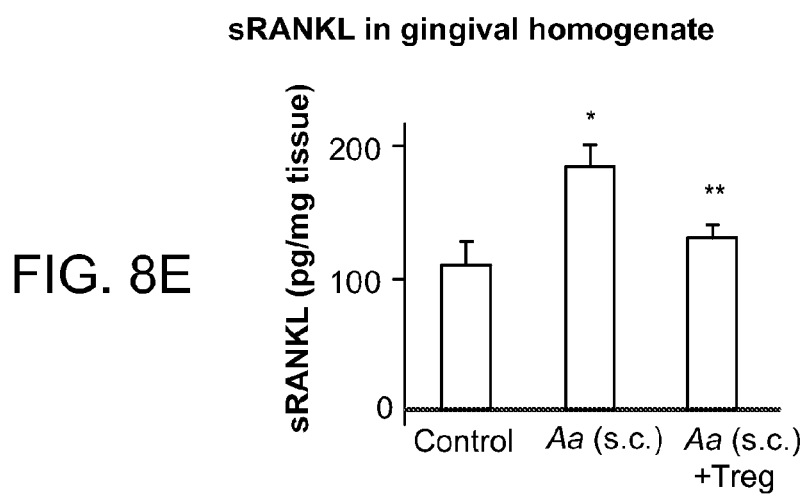
Figure 8F:
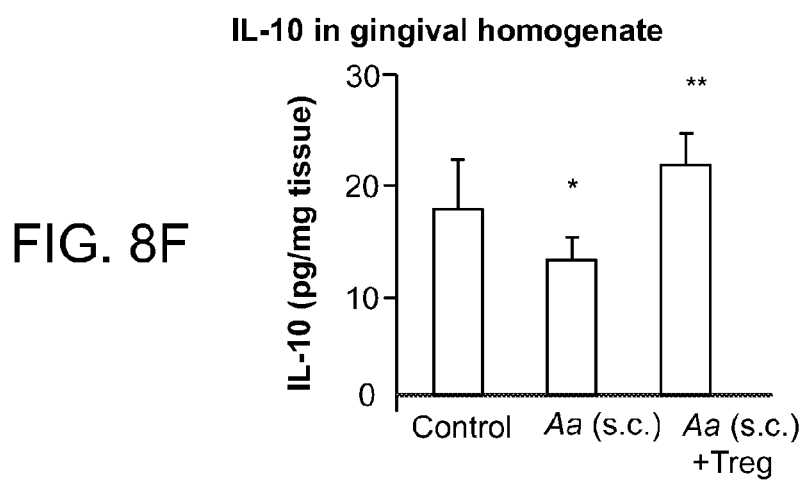

Adoptive transfer of FOXP3+ CD4 T cells inhibits in vivo mouse bone resorption induced by PPAIR. In order to investigate if an increase of FOXP3+ Treg cells can suppress PPAIR-caused periodontal bone resorption, CD25+FOXP3+ CD4+ iTreg cells were isolated from spleen T cells stimulated with TGF-b, IL-2 and Aa-antigen (FOXP3+CD25+ cells were 79.8% of the total CD4 T-cells) and were adoptively transferred to Pp+BALB/c mice that were immunized with fixed Aa (dorsal s.c.) on Day-0, -2 and -4. In an in vitro assay, CD25+FOXP3+CD4+ iTreg cells suppressed the proliferation and production of RANKL by antigen/APC-stimulated Aa-specific Th1 effector cells (FIG. 8B). For control, non-immunized mice and Aa-immunized mice, without adoptive transfer, were prepared. Thirty days after Aa immunization, PPAIR was observed in the Aa-immunized mice, as determined by the elevated IgG1 responses to Omp29, elevation of IFN-γ and sRANKL in the local gingival tissue (FIGS. 8D and 8E), and periodontal bone resorption (FIG. 8C). The transfer of CD25+FOXP3+CD4+iTreg cells to mice that received Aa systemic immunization significantly inhibited the following PPAIR features as compared to positive control animal groups: (1) increased IgG1 responses to Omp29; (2) IFN-g and sRANKL concentration in the gingival tissue (FIGS. 8D and 8E); and (3) local periodontal bone resorption (FIG. 8C). The amount of anti-inflammatory cytokine IL-10 in the gingival tissue was significantly increased by the transfer of iTreg cells (FIG. 8F). These results strongly suggest that local expansion of CD25+FOXP3+CD4+ iTreg cells can, in fact, inhibit periodontal inflammatory bone resorption induced by PPAIR by the mechanism of suppression of sRANKL and IFN-γ while activating IL-10 production in the local gingival tissues. This finding may be important in the context of the present invention because the efficacy of a material system in suppressing periodontal inflammation may be generated not by adoptive transfer, but by increasing host iTreg cells via activation of tolerogenic DC.

Local injection of polymer delivering GM-CSF/TSLP increases FOXP3+ T-cells in mouse gingival tissue and local lymph nodes (LN). The injection of polymeric delivery vehicles into the periodontal bone resorption socket of PD-induced FOXP3-EGFP-KI mice (C57BL6 background) was evaluated for the effects of the polymer on the resultant proportionality of Treg cells in the periodontal bone resorption lesion as well as local (cervical) lymph nodes. Seven days after the injection of polymer containing a mixture of GM-CSF (1 μg) and TSLP (1 μg) into the periodontal bone resorption socket (bone loss lesion developed 30 days after PPAIR induction by fixed Aa injection), an increase was observed in the proportion of FOXP3+EGFP+ Treg cells in cervical lymph nodes of mice that received GM-CSF/TSLP delivery polymer, whereas injection of polymer with GM-CSF (1 μg) alone did not show such increase of FOXP3+EGFP+Treg cells in the local lymph nodes compared to the control empty polymer injection (FIG. 9). Interestingly, in the connective tissue of PD lesion, remarkable infiltration of FOXP3+ cells was observed in the mice receiving GM-CSF/TSLP-polymer, as well as GM-CSF-polymer, while few FOXP3+ cells were detected in the bone loss lesion of mice that did not receive any injection. Of interest, the FOXP3+ cells were found in foci that are composed of a number of inflammatory cell infiltrates, suggesting that the injected polymer may provide a scaffold for Treg cells to react with tolerogenic DC. To support this premise, the co-localization of FOXP3+ cells and tolerogenic DC was observed in the legion that received GM-CSF/TSLP-polymer (FIG. 9C). Therefore, the GM-CSF/TSLP polymer material delivery system demonstrably expanded the anti-inflammatory FOXP3+ Treg cells in periodontal bone resorption lesion as well as local lymph nodes.

Materials for localized pDNA delivery and tissue regeneration, and polymer systems for sustained pDNA release were developed to allow for the localized delivery and sustained expression of pDNA with kinetics dependent on the rate of polymer degradation. Macroporous scaffolds of PLG may be used for the encapsulation of pDNA, with its subsequent release regulated by the degradation rate of the particular PLG used for encapsulation; allowing for sustained release of plasmid DNA for times ranging from 10-30 days. To enhance the uptake of pDNA, and to localize the plasmid to the region encompassed by the polymer, pDNA was condensed with PEI prior to incorporation into the polymeric vehicles. Implantation of scaffolds containing either an uncondensed or PEI-condensed marker gene (luciferase) resulted in the short-term expression of the uncondensed DNA, but a very high and extended duration of expression for the PEI-condensed DNA. Further, implantation of polymers delivery PEI condensed pDNA encoding for BMP-2 or BMP-4 led to long-term BMP-4 expression by host cells (FIG. 10A), and significantly more bone regeneration than the polymer alone, delivery of non-condensed pDNA, or no treatment (FIG. 10B-10D).

Figure 11A:
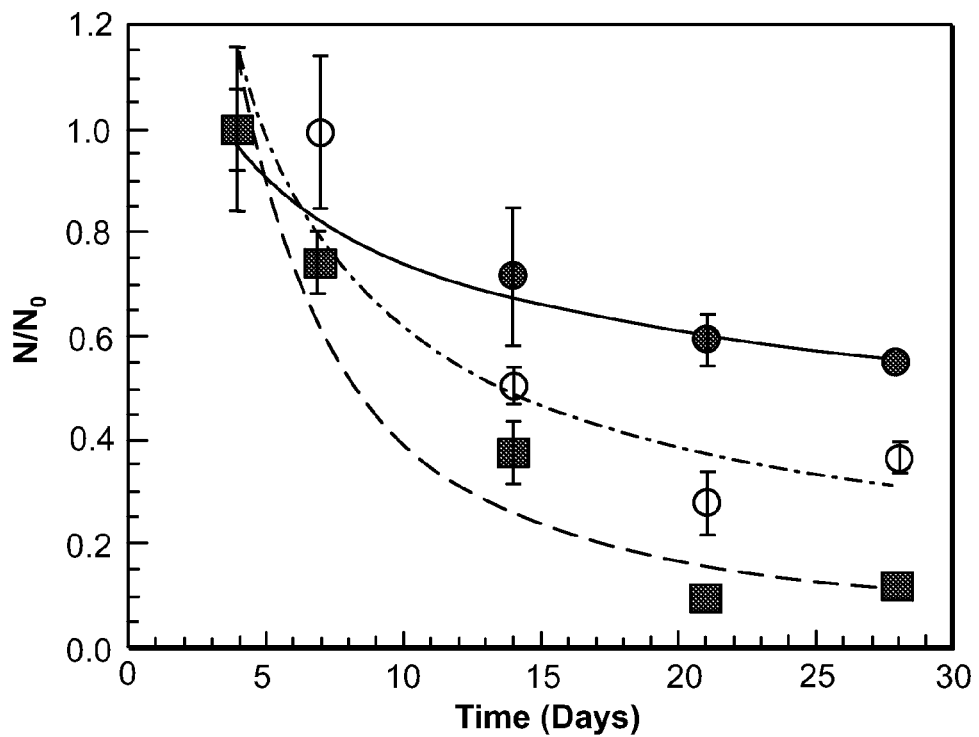
FIGS. 11A-B are line graphs demonstrating precise control over the timing of pDNA release from alginate gels with ultrasound. Alginate gels encapsulating pDNA were incubated in tissue culture medium, and an ultrasound transducer was placed in the medium. Irradition (1W) was applied to gels for 15 min daily; the release rate of pDNA was analyzed by collecting medium and quantifying pDNA in the solution. The base release rate of pDNA was minimal from the high molecular weight, slowly degrading gels used in these studies.
Figure 11B:
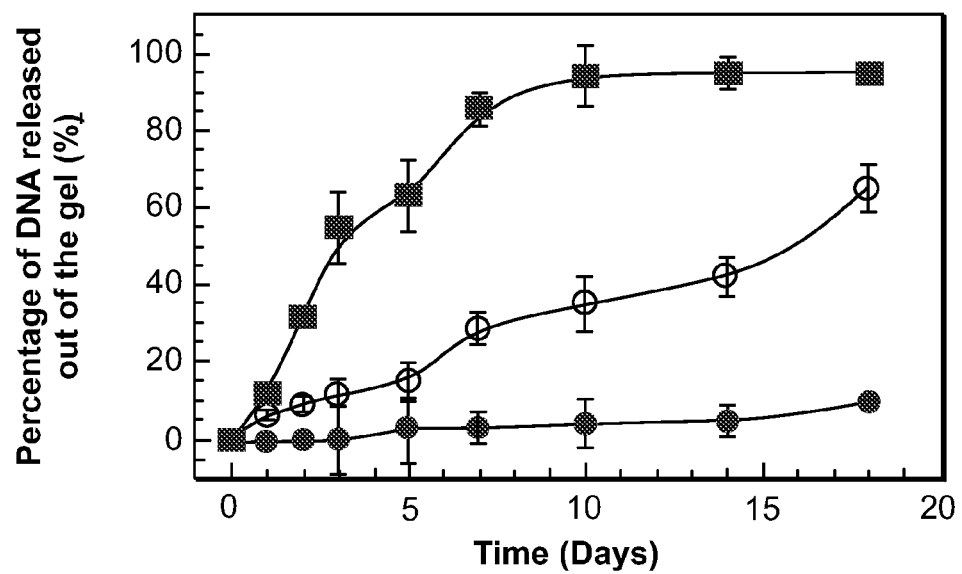

This approach can be extended to injectible alginate gels. The degradation rate of alginate gels is altered by controlling the molecular weight distribution of the polymer chains comprising the gels. The rate of gel degradation (FIG. 11A) strongly correlated with the timing of release of PEI condensed pDNA encapsulated in the gels (FIG. 11B). The timing of pDNA expression in vitro and in vivo was regulated by the gel degradation rate, and this approach to pDNA delivery led to physiologically relevant expression in vivo of an encoded morphogen, and significant effects on local tissue regeneration.

Figure 12:
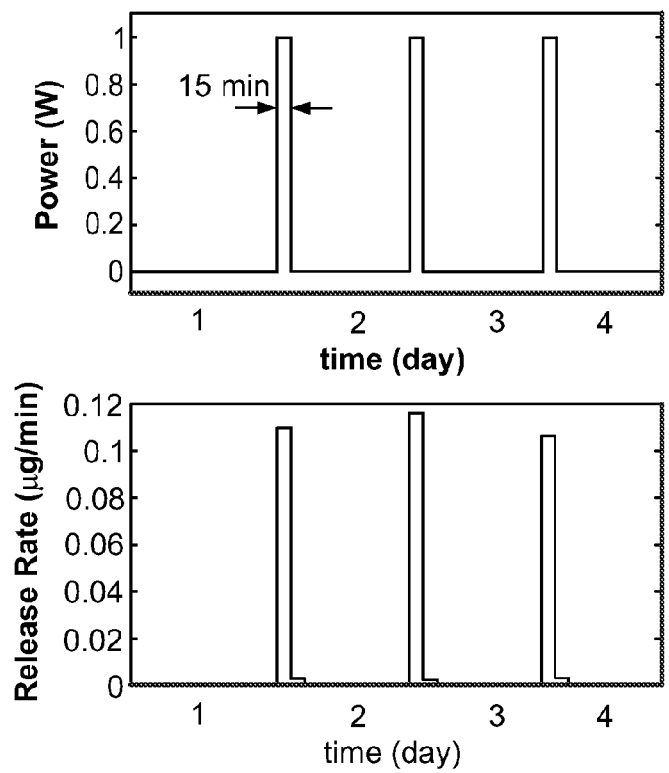
FIG. 12 is a line graph showing pDNA release rate.

The present invention provides for the delivery of pDNA encoding an osteogenic factor subsequent to amelioration of chronic inflammation, using regulated pDNA release from the delivery vehicle. Ultrasound irradiation may be used to trigger the release of pDNA from alginate hydrogels, as ultrasound may provide an external trigger to control release of drugs from materials placed in periodontal tissue. Ultrasound has been pursued widely in past studies of drug delivery from the perspective of permeabilizing skin to enhance drug transport, but in present invention exploits the transient disruption of the gel structure during ultrasound application to enhance release of pDNA encapsulated in the gels. Use of a high molecular weight, non-oxidized alginate to form the gel (unary gel in FIG. 12A) led to minimal background release of pDNA, due to the slow degradation of this gel (FIG. 12). Application of appropriate ultrasound irradiation led to a 1000-fold increase in the pDNA release rate; the rate rapidly returned to baseline levels following cessation of irradition (FIG. 12). The increase in pDNA release with ultrasound application correlated with large-scale perturbations of gel structure, as noted in past studies for biological samples. The subsequent rapid return of pDNA release rate to base-line levels correlated with a reversal of the gel structure to the original state. The ability of the alginate gels to "heal" following ultrasound likely is due to their reversible cross-linking with calcium ions in their environment. The present invention thus provides for precise control the timing of release of pDNA encoding osteogenic stimuli from the biomaterials matrix, at a time-point sufficient to first allow for conversion of the immune response to a non-inflammatory state.

Analysis of Kinetics of Gingival Treg Cell Induction in the Mouse PD Model

Experiments were carried out to determine how long it takes for the induction of Treg cells and alterations in the local inflammatory environment with GM-CSF/TSLP delivery by alginate gel. Knowing the optimal time when inflammation is sufficiently and efficiently quenched by GM-CSF/TSLP-gel injection indicates the optimal timing for the release of pDNA-encoding BMP2 from the material system.

FOXP3-EGFP-KI mice (8 wk old, 12 males/group) that harbor Pp in the oral cavity receive immunization of fixed Aa ($10^9$ bacteria/site/day dorsal s.c. injection on Day 0, 2 and 4). At Day-30, the development of periodontal bone loss is confirmed by probing of gingival pockets of maxillary molars. Serum IgG responses to Pp and Aa, along with the cross-reactive immunogenic antigens, including Pp OmpA (a homologue of Aa Omp29), are measured by ELISA because elevated IgG response to Pp antigens at Day-30 confirms that PPAIR successfully induces the development of vertical bone loss. Assuming that the levels of bone loss between left and right sides at Day 30 are symmetrical in each animal, the effects of GM-CSF/TSLP and the role of induced Treg cells are evaluated by palatal maxillary injection of gel with and without CD25+FOXP3+ Treg depletion by anti-CD25 MAb:

Group A: an injection of (1) mock empty gel to left, and 2) GM-CSF/TSLP to right, palatal maxillary gingivae;

Group B: same gingival injections as Group A, but the mice receive anti-CD25 MAb (500 µg/mouse, i.v. rat MAb hybridoma clone PC61 from ATCC) 3 days prior to gel injection;

Group C: same gingival injections as Group A, but the mice receive control purified rat IgG (500 µg/mouse, i.v.) 3 days prior to the gel injection;

Group D: an injection of mock empty gel to left, but no injection to the right, palatal maxillary gingivae.

The alginate gels were injected into the bone loss legion (1.5 µl/site). Animals are sacrificed on Day-33, -37, -44, and -58 (=3, 7, 14 and 28 days after injection of gels, respectively). Control, non-treated C57BL/6 mice sacrificed on Day-30 provide base-line information about inflammatory response and level of bone loss before the treatment with GM-CSF/TSLP-gel. The depletion of CD25+FOXP3+ Treg cells in Group B is confirmed by detection of CD25+FOXP3+ cells in the peripheral blood isolated from Group B and Group C using flow cytometry at Day-30. The dose and timing of TSLP/GM-CSF presentation from gels is determined, and 2-3 different doses are tested. Analysis included of: (1) Fluorescent immunohistochemistry for the detection of FOXP3+EGFP+Treg cells and other inflammatory cell types (e.g., macrophages, neutrophils), gingival tissue cytokine measurement, detection of inflammatory chemical mediators in gingival tissue, and measurement of FOXP3+EGFP+Treg cells and other lymphocyte phenotypes in cervical lymph nodes by flow cytometry; (2) analyses of TRAP+ osteoclasts, Periostin+/ALP+ osteoblasts and Periostin+/ALP+ ligament fibroblasts in decalcified periodontal tissues; and (3) extent of bone resorption using micro-CT, and quantitative histomorphometry.

Evaluation of Effects of GM-CSF/TSLP-Gels on the Immune Memory of iTreg Response The efficacy of gel delivery of GM-CSF/TSLP in eliciting immune memory, as challenged by recurrent activations of PPAIR, was explored. The aspect of immune memory is significant because once immune memory of iTreg response can be induced, it should be capable of preventing recurrent episodes of pathogenic periodontal bone loss at the same site, and the development of future periodontal bone loss at different sites.

PD was induced as described above. At Day-30, Groups A and B receive identical gingival injections: (1) an injection of mock empty gel to left, and (2) an injection of GM-CSF/TSLP to right, palatal maxillary gingivae. At Day 44, however, Group A receives adoptive transfer of Aa/Pp cross-reactive Th1 cell transfer in saline (i.v.), as this has been shown to cause periodontal bone loss. Such Th1 cell transfer constitutes a secondary (recurrent) activation of PPAIR. Group B mice receive control saline (i.v.) injections. Animals are sacrificed on Day-51 (=21 days after injection of gels and 7 days after Th1 cell transfer). Control, non-treated C57BL/6 mice sacrificed on Day-30 provide the base-line information about inflammatory response and level of bone loss without treatment with GM-CSF/TSLP-gel. The analysis involves: (1) Fluorescent immunohistochemistry for the detection of FOXP3+EGFP+Treg cells and other inflammatory cell types, measurement of gingival tissue cytokines and chemical mediators, and measurement of FOXP3+EGFP+Treg cells and other lymphocyte phenotypes in cervical lymph nodes by flow cytometry; (2) Analyses of TRAP+ osteoclasts, Periostin+/ALP+ osteoblasts and Periostin+/ALP+ ligament fibroblasts in decalcified periodontal tissues; and (3) periodontal bone loss measurement.

Relation Between tDCs and iTregs.

A series of studies addressed the relationship between GM-CSF/TSLP-induced tolerogenic DC (tDCs) and local development of Treg cells. The functional roles of chemokines and common γchain (γc)-receptor-dependent cytokines produced by GM-CSF/TSLP-induced tDCs on the extra-thymic development of Treg cells. Treg cells migrate to fungus-infected lesions in a CCR5 dependent manner in a mouse model of pulmonary mycosis, and Treg cells migrate to the infectious lesion in response to the CCR5-ligands, such as MIP-1α, which are also known to be expressed by GM-CSF-stimulated DC CD25+CD4+ Treg cells can be developed by ex vivo stimulation with TGFα and IL-2 from whole spleen cells. Results (FIG. 8) demonstrated that ex vivo stimulation of mouse whole spleen cells with TGF-β and IL-2 up-regulated the development of FOXP3+ T-cells, indicating that FOXP3+ Treg cells are expandable ex vivo in response to appropriate stimulation. Common γchain (γc)-receptor-dependent cytokines are required for Treg cell expansion, which is demonstrated by the lack of Treg cells in γc-gene knockout mice. Several γc-receptor-dependent cytokines, e.g. IL-2, IL-7 and IL-15, up-regulate Treg development. Because TSLP, which also uses the γc-receptor, does not induce development of Treg cells TSLP released from the gels does not directly induce Treg development. However, DCs do not produce the major γc-receptor-dependent cytokine IL-2. Therefore, IL-15 that is produced by DC following stimulation with GM-CSF (Ge et all, 2002), facilitates Treg growth as a γc-receptor-dependent cytokine. If tDCs do not induce local development of FOXP3+ Treg cells from nTreg, then non-Treg cells, i.e., FOXP3(−)CD4(+) T cells, may migrate to the PD lesion and differentiate to FOXP3(+) iTreg cells by communication with the tDCs. Thus, these experiments examined in vitro chemokines and common γchain (γc)-receptor-dependent cytokines produced by GM-CSF/TSLP-induced tDCs and their functional roles in the chemo-attraction and development of FOXP3+ Treg cells.

Measurement of cytokines and chemokines produced by GM-CSF/TSLP-induced tDCs CD11+ DC are induced in vitro by the incubation of bone marrow cells with GM-CSF (10 ng/ml) in the presence or absence of TSLP (10 ng/ml). After 7 days of incubation, CD11c+DC are isolated from the bone marrow cell culture, using anti-CD11c MAb-conjugated MACS beads (DC isolation kit, Miltenyi Biotech). CD11c+DC are be separated from mononuclear cells (MNC) freshly isolated from the dorsal s.c. tissue of mice where GM-CSF-gel, GM-CSF/TSLP-gel or control empty gel (GM-CSF and TSLP, 1 ug and 1 ug, respectively; 1.5 ul-gel/site) is injected 7 days prior to the MNC isolation, using anti-CD11c MAb-conjugated MACS beads. Doses and concentrations are adjusted as necessary. These DC are incubated in vitro in the presence or absence of bacterial stimulation (fixed Aa, fixed P. gingivalis, Aa-LPS or Pg-LPS) or proinflammatory factor (IL1-α), and their expression level of chemokines and cytokines is measured quantitatively by Mouse Cytokine/Chemokine Panel-24-Plex (Millipore; see Table 1) using a Luminex multiplex system. The production of inflammatory chemical mediators ($PGE_2$, NO, ATP, and adenosine) are also monitored, although detection of ATP and adenosine from DCs.

In vitro assays examined the Treg cell chemo-attractant factors secreted from DC. The culture supernatants of Aa- or IL-1α-stimulated CD11c+DC, are placed in the bottom compartment of a transmigration system, while FOXP3(+)EGFP (+) Treg cells, or control FOXP3(−) CD4 T-cells, are freshly isolated from FOXP3-EGFP-KI mice by cell-sorting and applied to a cell-culture insert (5 μm pore size, Millipore). The kinetics and number of migrating FOXP3(+) Treg cells, or control FOXP3(−) CD4 T-cells, to the bottom compartment are monitored. In order to evaluate the functional role of Treg attracting factors, neutralizing mAb to the chemokines is applied to the bottom compartment with the supernatant of DC culture. MIP-1α is a Treg chemo-attractant secreted from tDCs. Recombinant chemokines serve as positive control chemo-attractant factors in this Treg cell migration assay. The expression of CCR2, CCR5 and other chemokine receptors expressed on the migrating FOXP3(+) Treg cells or control FOXP3(−) CD4 T-cells is monitored using flow cytometry.

Figure 13:
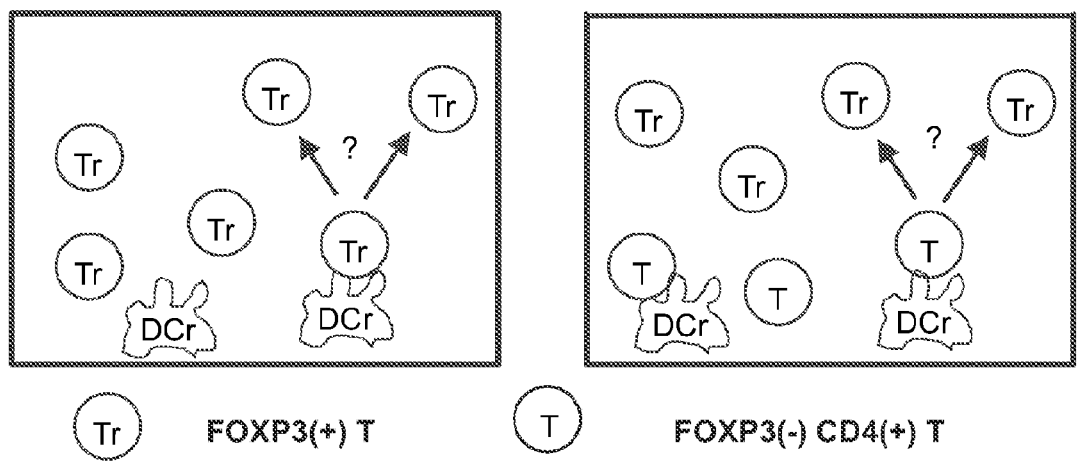
FIG. 13 is a schematic of an in vitro Treg development assay.

In vitro assays examined the FOXP3+ Treg development factors secreted from DCs. The CD11c+DC were co-cultured with FOXP3(+)Treg cells and FOXP3(−) CD4 T-cells isolated from the spleens of FOXP3-EGFP-KI mice in the presence or absence of Aa-antigen. After 3, 7 and 14 days of incubation, the proportion of FOXP3(+)Treg cells are analyzed using flow cytometry. As can be observed from the scheme of possible results shown in FIG. 13, the advantage of using FOXP3-EGFP-KI mice with this assay system derives whether DC-mediated Treg development occurs from FOXP3(+)Treg cells or FOXP3(−) CD4 T-cells because: (1) live FOXP3(+)Treg cells can be isolated from FOXP3-EGFP-KI mice; and (2) development of mature Treg cells from their precursors, which do not express the FOXP3 gene, can be monitored by the detection of EGFP expression. In order to evaluate the functional role of Treg growth cytokines, neutralizing mAb to the cytokines are applied to the co-culture between DC and T-cells. IL-15 may be the major Treg growth cytokine secreted from tDCs.

Inflammation is suppressed in the PD lesion by 7 days (Day-37) after the injection of GM-CSF/TSLP-gel and that suppression effects lasts until Day-58, the latest examination day.

Combining Anti-Inflammatory and Osteoinductive Signaling for Bone Regeneration

The utility of the immune programming system developed and studied is evaluated for its ability to enhance bone regeneration via co-delivery of osteoinductive cues. This approach both stops inflammation and actively promotes bone regeneration via delivery of pDNA encoding for BMP-2, using the same gel that releases GM-CSF/TSLP. The utility of the gel system is enhanced by its ability to release the pDNA on demand with an external signal (ultrasound irradiation). Ultrasound provides a number of advantages for this application, including its non-invasive nature, deep tissue penetration, and ability to be focused and controlled. The delivery system is used to first quench inflammation, and subsequently release pDNA to promote alveolar bone regeneration.

The first studies characterize ultrasound-triggered pDNA release from alginate gels, and subsequent studies examine bone regeneration using pDNA release from the gels in the PD model. Ultrasound can be used to trigger the release of pDNA from alginate gels after multiple days of incubation. Both PEI-condensed pDNA and uncondensed pDNA are encapsulated into alginate gels, and the passive pDNA release quantified. PEI-condensed pDNA is examined, as condensation dramatically upregulates pDNA uptake and expression, and the impact of ultrasound on release may be distinct for the two pDNA forms due to their different sizes and charges. Gels that vary in degradation times from 2-3 weeks to over 6 months are used for pDNA encapsulation, and little to no passive pDNA release occurs in the absence of gel degradation. The influence of varying regimes of low-frequency ultrasound irradiation (frequency of 20-50 kHz, intensity of 0.1-10 watt, duration 1-15 min) on pDNA release is examined after gels have incubated for times ranging from 1-3 weeks (to mimic the intended application in which GM-CSF/TSLP release occurs early and only following amelioration of inflammation will release of pDNA encoding BMP be triggered). The concentration of DNA in the release medium is assayed using Hoechst 33258 dye and a fluorometer (Hoefer DyNA Quant 200, Pharmacia Biotech, Uppsala, Sweden). The structural integrity of the released plasmid is examined using gel electrophoresis. Little effect of ultrasound on the GM-CSF and TSLP release is anticipated, as ultrasound is not initiated until after the majority of GM-CSF and TSLP have been released, but GM-CSF and TSLP release is be monitored during irradiation to determine if ultrasound impacts the release of any residual GM-CSF/TSLP remaining in the gels.

The ability of on-demand pDNA release from gels to enable in vivo transfection is examined to confirm both that ultrasound can regulate pDNA in vivo in a similar fashion as noted in vitro, and to determine the appropriate pDNA dose for bone regeneration studies. Gels containing pDNA encoding GFP are injected into palatal maxillary gingivae of normal mice (no periodontal disease), and subjected to ultrasound at times ranging from 7-21 days after introduction. The in vitro studies are used as a guide for the relevant frequency, intensity, and duration of irradiation. An exemplary ultrasound schedule comprises application once per day, for time-frames ranging from 1-7 days. One day following the end of each irradiation period, animals are sacrificed, and tissue sections obtained for both histology and biochemical quantification of overall GFP expression in the tissue. Uncondensed and PEI-condensed pDNA are compared in these studies, and the doses of encapsulated pDNA varied from 1 µg-100 µg. Tissue sections are immunostained for GFP to qualitatively study pDNA expression, and GFP levels also quantified in tissue lysates to quantify expression.

Another embodiment of this invention provides for the impact of the gel system to first ameliorate inflammation, and then actively promote regeneration in the PD mouse model. PD is characterized by chronic inflammation that leads to tissue destruction and bone resorption around the teeth. After induction of PD, gels containing GM-CSF, TSLP, and pDNA encoding BMP-2 are injected at Day-30. After sufficient time has elapsed to allow inflammation to reside, ultrasound irradiation is initiated to release pDNA encoding BMP-2. At 2, 4 and 8 weeks following gel placement, the soft and hard tissue is retrieved and analyzed. The level of inflammation is monitored by measurement of inflammatory chemical mediators present in the gingival tissue, and BMP-2 levels is also quantified with ELISA to examine gene expression. Bone regeneration is quantified using micro-CT and histologic analysis is also performed to allow quantitative histomorphometry of bone quantity. Controls include no treatment, gels containing pDNA only (no GM-CSF/TSLP), and blank gels. A sample size of 6/time point/condition is anticipated to be necessary studies of bone regeneration.

Reducing inflammation dramatically increases bone regeneration resulting from osteoinductive factor delivery, as compared to osteoinductive factor alone. Ultrasound provides a useful trigger to control the release of pDNA from alginate gels, both in vitro and in vivo, allowing a single gel to deliver the GM-CSF/TSLP and the plasmid with appropriate release kinetics. In some cases, there is an interplay between the gel degradation rate and ultrasound-triggered release due to the changes in gel structure resulting from degradation. Two gel injections—the first delivering GM-CSF/TLSP to ameliorate inflammation, and the second to delivery pDNA encoding BMP-2 after inflammation has been reduced, may be used.

High, local levels of BMP-2 significantly enhance bone regeneration. The major effect of ultrasound on regeneration is triggered release of pDNA from gels, but ultrasound also enhances cellular uptake of pDNA and thus directly enhances expression of locally delivered pDNA in addition or without effects on pDNA release.

The following materials and methods were used in periodontal studies described herein. In vitro DC assays Migration assays are performed with 6.5 mm transwell dishes (Costar, Cambridge, Mass.) with a pore size of 5 µm. The effects of GM-CSF and TSLP, (Invivogen, San Diego, Calif.) on the migration of DCs are assessed by placing recombinant murine GM-CSF and TSLP in the bottom wells and $5\times10^5$ DCs in the top wells. To assess the effects of GM-CSF and TSLP on DC activation, cells are cultured with bacterial stimulation (fixed Aa, fixed *P. gingivalis*, Aa-LPS or Pg-LPS along) with various concentrations of TSLP and GM-CSF for 24 hours and then the cells are washed and fixed in 10% formalin. The cells are prepared for fluorescence immunohistochemistry as per below, and examined using fluorescent microscopy (Olympus, Center Valley, Pa.). Cells are also analyzed by FACS, and gated according to positive stains using isotype controls, and the percentage of cells staining positive for each surface antigen will be recorded. The expression of cytokines upregulated as a result of DC maturation is quantified as described below.

Gel Fabrication

Gels are created from alginates varying in mannuronic to guluronic acid residues, molecular weight distributions, and extent of oxidation to regulate their rheological, physical and degradation properties. Hydrogels are prepared by mixing alginate solutions containing the factors as previously described for proteins and plasmid DNA formulations with a calcium sulfate slurry. If necessary, factors are first encapsulated into PLG microspheres using a standard double emulsion technique.

Quantification of GM-CSF, TSLP, and pDNA in Vitro Release Studies, and in Vivo Concentrations To determine the efficiency of GM-CSF, TSLP, and pDNA incorporation and the kinetics of release, $^{125}$I-labeled factors (Perkin Elmer) are utilized as a tracer, and gels and placed in Phosphate Buffer Solution (PBS) (37° C.). At various time points, the PBS release media is collected and amount of $^{125}$I-factor released from the scaffolds is determined at each time point using a gamma counter and normalizing to the total $^{125}$I-factor incorporated into the gels. To asses the retention of GM-CSF bioactivity, loaded gels are placed in the top wells of 6.5 mm transwell dishes (Costar, Cambridge, Mass.) with a pore size of 3 µm and the proliferation of JAWS II cells (DC cell line) cultured in the bottom wells is evaluated at various time points using cell counts from a hemacytometer. To determine GM-CSF and TSLP concentrations in vivo, tissue surrounding gels is excised and digested with tissue protein extraction reagent (Pierce). After centrifugation, the concentration of GM-CSF and TSLP in the supernatant is then analyzed with ELISA (R&D systems), according to the manufacturers instructions.

In Vivo DC Migration and Activation Assays

Gels with various combinations of factors are injected into gingival of mice. For histological examination gels and surrounding tissue are excised and fixed in Z-fix solution, embedded in paraffin, and stained with hematoxylin and eosin. To analyze DC recruitment, gels and surrounding tissue are excised at various time-points and the tissue digested into single cell suspensions using a collagenase solution (Worthington, 250 U/ml) that was agitated at 37° C. for 45 min. The cell suspensions are then poured through a 40 mm cell strainer to isolate cells from gel particles and the cells are pelleted and washed with cold PBS and counted using a Z2 coulter counter (Beckman Coulter). The resultant cell populations are then stained with primary antibodies conjugated to fluorescent markers to allow for analysis by flow cytometry. Cells are gated according to positive labels using isotype controls, and the percentage of cells staining positive for each surface antigen is recorded.

Fluorescent Immunohistochemistry

To evaluate the tissue localization pattern of specific cells in gingival tissues and cervical LN, confocal microscopic analysis is employed. Using the 3-color staining procedure, key subsets, tDCs (cells positive for CD11c and CD86 and IL-10), mature DCs (positive for CCR7, B7-2, MHCII), FOXP3+ T cells (EGFP, IL-10 and TGF-b), FOXP3+CD25+ T cells (EGFP, CD25, IL-10), RANKL+CD3+ T cells (RANKL, CD3 and TNF-a) and RANKL+CD19+ B cells are stained. Expression of CD26, CD39 and CD73 on FOXP3+ T cells as well as on RANKL+CD3+ T cells, DC(CD11c+), B cells (CD19+), macrophages (F4/80+) and neutrophils (CD64+) are also monitored. Detection of RANKL is conducted by a combination of biotin-conjugated-OPG-Fc/TR-avidin. Other molecules are stained using a conventional method with primary specific-monoclonal antibody followed by secondary antibody conjugated with fluorescent dye: 1st color, FITC (emission/excitation, 488/515 nm); 2nd color, Texas Red (595/615); and 3rd color, APC/Cy5.5 (595/690).

Flow Cytometry

The prevalence of various cells in gingival tissue and local cervical lymph nodes is analyzed by flow cytometry. Nonspecific antibody binding to the Fc receptor is blocked by pre-incubating the cells with rat MAb 2.4G2 (reactive to CD16/CD32). Three-color staining method is employed for the detection of tDCs, mature DC, EGFP+FOXP3+ T cells and RANKL+CD3+ T cells.

Detection of Cytokines from Culture Medium and Gingival Tissue Homogenates

Standard methods were used to detect cytokines and other markers such as IL-10, RANKL, OPG, Osteocalcin, TNF-a, IFN-g, TGF-b1, IL-1b, IL-2, IL-4, IL-6, IL-12 and IL-17 in the culture medium or mouse gingival tissue homogenates.

Detection of Inflammatory Chemical Mediators Present in Gingival Tissue

Both pro-inflammatory ($PGE_2$, nitric oxide [NO] and ATP) and anti-inflammatory chemical mediators (adenosine) are measured. $PGE_2$ is measured using a Luminex-based $PGE_2$ detection kit (Cayman Chemical). Nitric oxide present in tissue homogenate is measured by Nitrate/Nitrite Colorimetric Assay Kit (Cayman Chemical). The concentration of ATP and adenosine will be measured using Sarissaprobe®-ATP and Sarissaprobe®-ADO sensors (Sarissa Biomedical, Coventry, UK).

Trap Staining for Osteoclasts and Periostin/ALP Staining for Osteoblasts and Periodontal Ligament Fibroblasts in Periodontal Bone The maxillary jaws of animals sacrificed on Day-33, -37, -44, and -58 are decalcified, and osteoclast cells determined by TRAP staining on the tissue sections. The tissue sections are also stained for Periostin and alkaline phosphatase to determine the localization of osteoblasts and periodontal ligament fibroblasts.

pDNA Studies

Plasmid DNA containing the CMV promoter and encoding for green fluorescent protein (GFP) (Aldevron, Fargo N. Dak.) or bone morphogenetic protein 2 (BMP-2) (Aldevron) are used. Branched polyethylenimine (PEI, MW=25000, Sigma-Aldrich) is used to condense plasmid DNA for more efficient transfection.

Application of Ultrasound

An Omnisound 3000 will be to mediate pDNA release from gels. The structure of gels subject to sonication in vitro are examined via analysis of rheological properties at varying times post-treatment to determine permanent changes in gel structure, and recovery time post-treatment. pDNA release, structure, and gene expression are evaluated using standard methods. For in vivo studies, a 1-$cm^2$ transducer head is used with aquasonic coupling gel on the tissue surface; a thermocouple is inserted into the tissue site to measure local temperature.

Monitoring Extent of Bone Regeneration

Tissues are analyzed initially by microCT and then histologically to determine the extent of bone formation. Digital µCT images are taken and reconstructed into a 3-dimensional image with a mesh size of 25 µm×25 µm×25 µm. Scanning may be performed on a GE-EVS high resolution MicroCT System available at the Brigham and Woman core facility, on a per fee basis. Bone volume measures, and calibrated bone mineral density are determined. Quantitative histomorphometric analysis is carried out using standard methods, from plastic embedded sections stained with Goldner's Trichrome stain for osteoid or von Kossa stain for mineralized tissue.

Statistical Design and Analysis

Sample numbers for all experiments are calculated using InStat Software (Agoura Hills, Calif.), using standard deviations determined in preliminary studies, in order to enable the statistical significance of differences between experimental conditions of greater than 50% to be established. Statistical analysis will be performed using Students t-test (two-tail comparisons), and analyzed using InStat 2.01 software. Differences between conditions are considered significant if $p<0.05$.

All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of reducing the severity of an autoimmune disorder, comprising identifying a subject suffering from an autoimmune disorder and administering to said subject a scaffold composition comprising an antigen, a recruitment composition, and a tolerogen, wherein said antigen is derived from a cell to which a pathologic autoimmune response associated with said disorder is directed, and wherein said tolerogen induces immune tolerance or a reduction in an immune response, wherein said scaffold composition comprises an alginate gel, granulocyte macrophage colony-stimulating factor (GM-CSF), and thymic stromal lymphopoietin.

2. The method of claim 1, wherein said scaffold composition further comprises dexamethasone.

3. The method of claim 2, wherein said dexamethasone is loaded into the alginate gel, and wherein the dexamethasone is encapsulated in poly(lactide-co-glycolide) (PLGA) microspheres prior to loading into the alginate gel.

\* \* \* \* \*

UNITED STATES PATENT AND TRADEMARK OFFICE
CERTIFICATE OF CORRECTION

PATENT NO. : 8,728,456 B2
APPLICATION NO. : 13/386950
DATED : May 20, 2014
INVENTOR(S) : Sands et al.

Page 1 of 1

It is certified that error appears in the above-identified patent and that said Letters Patent is hereby corrected as shown below:

On the Title Page

At Item (75):
Please replace "EDUARDO ALEXANDRA BARROS E SILVA" with --EDUARDO ALEXANDRE BARROS E SILVA--

In the Specification

Column 1, Lines 15-18:
Please replace "This invention was funded in part by the U.S. Government under grant number 5R01DE019917-02 awarded by the National Institutes of Health. The Government has certain rights in the invention." with --This invention was funded in part by the U.S. Government under grant number DE019917 awarded by the National Institutes of Health. The Government has certain rights in the invention.--

Signed and Sealed this
Seventh Day of May, 2019

Andrei Iancu
*Director of the United States Patent and Trademark Office*

UNITED STATES PATENT AND TRADEMARK OFFICE
CERTIFICATE OF CORRECTION

PATENT NO. : 8,728,456 B2
APPLICATION NO. : 13/386950
DATED : May 20, 2014
INVENTOR(S) : Sands et al.

It is certified that error appears in the above-identified patent and that said Letters Patent is hereby corrected as shown below:

In the Specification

At Column 1, Lines 15-18, please replace "This invention was funded in part by the U.S. Government under grant number DE019917 awarded by the National Institutes of Health. The Government has certain rights in the invention." with --This invention was made with government support under DE019917 awarded by the National Institutes of Health. The government has certain rights in the invention.--

This certificate supersedes the Certificate of Correction issued May 7, 2019.

Signed and Sealed this
Thirteenth Day of May, 2025

Coke Morgan Stewart
*Acting Director of the United States Patent and Trademark Office*